United States Patent
Davis

(10) Patent No.: US 7,572,604 B2
(45) Date of Patent: Aug. 11, 2009

(54) MODIFIED CARBOHYDRATE PROCESSING ENZYME

(75) Inventor: Benjamin G. Davis, Oxford (GB)

(73) Assignee: Isis Innovation Limited, Oxford (GB)

( * ) Notice: Subject to any disclaimer, the term of this patent is extended or adjusted under 35 U.S.C. 154(b) by 413 days.

(21) Appl. No.: 10/679,692

(22) Filed: Oct. 7, 2003

(65) Prior Publication Data
US 2009/0181444 A1 Jul. 16, 2009

Related U.S. Application Data

(60) Provisional application No. 60/416,263, filed on Oct. 7, 2002.

(51) Int. Cl.
*C12N 9/24* (2006.01)
*C12P 19/00* (2006.01)
*C12P 19/14* (2006.01)

(52) U.S. Cl. .............................. 435/99; 435/200; 435/72

(58) Field of Classification Search .................. 435/200, 435/195, 193, 6, 69.1, 320.1; 536/23.2
See application file for complete search history.

(56) References Cited

U.S. PATENT DOCUMENTS

2003/0138880 A1* 7/2003 Withers et al. ............. 435/68.1

FOREIGN PATENT DOCUMENTS

WO WO 02/080980 10/2002

OTHER PUBLICATIONS

DeSantis et al. Site-directed mutagenesis combined with chemical modification as a strategy for altering the specificity of the S1 and S1' pockets of subtilisin Bacillus lentus. Biochemistry. Apr. 28, 1998;37(17):5968-73.*
Aguilar et al. "Crystal structure of the β-glycosidase from the hyperthermophilic archeon *sulfolobus solfataricus*: Resilience as a key factor in thermostability" J. Mol. Biol. 271:789-802 (1997).
Andrews et al. Substrate specificity in glycoside hydrolase family J. Biol. Chem. 275:23027-23033 (2000).
Babcock et al. "Facile preparation of unsymmetric cabodiimides via in situ Tin(II)-mediated heterocumulene metathesis" J. Am. Chem. Soc. 120:5585-5586 (1998).
Banner et al. "Structure of chicken muscle triose phosphate isomerase determined crystallographically at 2.5Å resolution", Nature 255:609-614 (1975).
Barton et al. "Structure, mechanism and engineering of a nucleotidylytransferase as a first step toward glycorandomization" Nature Struct. Biol. 8:545-551 (2001).
Breidt et al. "Nucleotide and deduced amino acid sequences of the *staphylococcus aureus* phospho-βgalactosidase gene" Appl. Environ.Microbiol. 53:969-973 (1987).
Cairns et al. "Primary structure of the dalcochinin-8'-O-beta-glucoside beta-glucosidase from the thai Rosewood Dalbergia cochinchinensis pierre"TREMBL:Q9SPK3.

Corbett et al. "Tailoring the substrate specificity of the β-glycosidase from the thermophilic archaeon *sulfolobus solfataricus*" FEBS Lett. 509:355-360 (2001).
Crout et al. "Glycosidases and glycosyl transferases in glycoside and oligosaccharide synthesis" Curr. Opin. Chem. Biol. 2:98-111 (1998).
Cubellis et al. "Isolation and sequencing of a new β-galactosidase-encoding archaebacterial gene" Gene 94:89-94 (1990),
Davis "Recent developments in oligosaccharide synthesis" J. Chem. Soc., Perkin Trans. 1:2137-2160 (2000).
Fort et al. "Highly efficient synthesis of β(1→4)-oligo and polysaccharides using a mutant cellulase" J. Am. Chem. Soc. 122:5429-5437 (2000).
Henrissat "A classification of glycosyl hydrolases based on amino acid sequence similarities" Biochem. J. 280:309-316 (1991).
Inoue et al. "Molecular cloning and bacterial expression of cDNA encoding furostanol glycoside 26-O-β-glucosidase *Costus speciosus*" FEBS Lett. 389:273-277 (1996).
Kaper et al. "Comparative structural analysis and substrate specificity engineering of the hyperthermostable β-glucosidase CelB from *Pyrococcus furiosus*" Biochem. 39:4963-4970 (2000).
Koeller et al. "Emerging themes in medicinal glycoscience" Nature Biotechnol. 18:835-841 (2000).
Kren et al. "Glycosylation employing bio-systems: From enzymes to whole cell" Chem Soc. Rev. 26:463-473 (1997).
Krstenansky et al. "Biocatalytic combinatorial synthesis" Bioorganic & Medicinal Chemistry 7:2157-2162 (1999).
Mackenzie et al. "Glycosynthases: Mutant glycosidases for oligosaccharide synthesis" J. Am. Chem. Soc. 120:5583-5584 (1998).
Malet et al. "From β-glucanase to β-glucansynthase: Glycosyl transfer to α-glycosyl fluorides catalyzed by a mutant endoglucanase lacking its catalytic nucleophile" FEBS Lett. 440:208-212 (1998).
Mantei et al. "Complete primary structure of human and rabbit lactase-phlorizin hydrolase: Implications for biosynthesis, membrane anchoring and evolution of the enzyme" EMBO J. 7:2705-2713 (1988).
Mayer et al. "The E358S mutant of *Agrobacterium* sp. β-glucosidase is a greatly improved glycosynthase" FEBS Lett. 466:40-44 (2000).
Moracci et al. "Identification of two glutamic acid residues essential for catalysis in the β—glycosidase from the thermoacidophilic archaeon *Sulfolobus solfataricus*" Protein Engineering 9:1191-1195 (1996).
Morcci et al. "Expression and extensive characterization of a β-glycosidase from the extreme thermoacidophilic archaeon *Sulfolobus solfataricus in Escherichia coli*. Authenticity fo the recombinant enzyme" Enzyme and Microbial Technology 17:992-997 (1995).

(Continued)

*Primary Examiner*—Nashaat T Nashed
*Assistant Examiner*—Iqbal H Chowdhury
(74) *Attorney, Agent, or Firm*—Nixon & Vanderhye P.C.

(57) ABSTRACT

A modified polypeptide having carbohydrate processing enzymatic activity is provided, said polypeptide comprising an amino acid sequence selected from: (a) the amino acid sequence of SEQ ID NO:2 comprising a mutation in at least one of W433, E432 and M439; (b) the amino acid sequence of an enzyme of glycosyl hydrolase family 1, comprising at least one mutation at an amino acid residue equivalent to W433, E432 or M439 of SEQ ID NO:2; and (c) a variant of (a) or (b) having carbohydrate processing enzymatic activity and comprising at least one amino acid mutation at a position equivalent to W433, E432 or M439 of SEQ ID NO:2.

29 Claims, 2 Drawing Sheets

OTHER PUBLICATIONS

Moracci et al. "Restoration of the activity of active-site mutants of the hyperthermophilic β-glycosidase from *Sulfolobus solfataricus*: Dependence of the mechanism on the action of external nucleophiles" Biochem. 37:17262-17270 (1998).

Michels et al. "Combinatorial biocatalysis: A natural appraoch to drug discovery" Trends Biotechnol. 16:210-215 (1998).

Nashiru et al. "β-mannosynthase: Synthesis of β-mannosides with a mutant β-mannosidase" Angew. Chem. Int. Ed. 40:417-421 (2001).

Nucci et al. "Exo-glucosidase activity and substrate specificity of the β-glycosidase isolated from the extreme thermophile *Sulfolobus solfataricus*" Biotechnol. Appl. Biochem. 17:239-250 (1993).

Palcic "Biocatalytic synthesis of oligosaccharides" Curr. Opin. Biotechnol. 10:616-624 (1999).

Pisani et al. "Thermostable β-galactosidase from the archaebacterium *Sulfolobus solfataricus*" Eur. J. Biochem. 187:321-328 (1990).

Prade et al. "Enzymatic synthesis of disaccharides using *Agrobacterium* sp. β-glucosidase" Carbohydrate Res. 305:371-381 (1998).

Rantwijk et al. "Glycosidase-catalysed synthesis of alkyl glycosides" J. Mol. Catal. B: Enzym. 6:511-532 (1999).

Rye et al. "Glycosidase mechamisms" Curr. Opin. Chem. Biol. 4:573-580 (2000).

Scigelova et al. "Glycosidases—a great synthetic tool" J. Mol. Catal. B: Enzym. 6:483-494 (1999).

Trincone et al. "A novel thermophilic glycosynthase that effects branching glycosylation" Bioorganic & Medicinal Chem. Lett. 10:365-368 (2000).

Voorhorst et al. "Characterization of the *celB* gene coding for β-glucosidase from the hyperthermophilic archaeon *Pyrococcus furious* and its expression and site-directed mutation in *Escherichia coli*" J. Bacteriol. 177:7105-7111 (1995).

Watt et al. "Enzyme-catalyzed formation of glycosidic linkages" Curr. Opin. Struct. Biol. 7:652-660 (1997).

Wymer et al. "Enzyme-catalyzed synthesis of carbohydrates" Curr. Opin. Chem. Biol. 4:110-119 (2000).

Xue et al. "The glucosinolate-degrading enzyme myrosinase in *Brassicaceae* is encoded by a gene family" Plant Mol. Biol. 18:387-398 (1992).

Zhang et al. "Directed evolution of a fucosidase from a galactosidase by DNA shuffling and screening" Proc. Natl. Acad. Sci. USA 94:4504-4509 (1997).

Lesk, *Bioinformatics*, New York: Oxford University Press, pp. 184-187 (2002).

Henrissat et al. "Carbohydrate-active enzymes in completely sequenced genomes" in *Carbohydrate Bioengineering: Interdisciplinary Approaches*, Teeri et al. (eds.), Cambridge: RSC Publishing, pp. 172-177 (2002).

Orengo et al. "Sequence comparison methods" in *Bioinformatics: Genes, Proteins & Computers*, Orengo et al. (eds.), New York: Garland Science/BIOS Scientific Publishers, Chapter 3, pp. 29-46 (2003).

\* cited by examiner

FIG. 1

```
                                                      ↓↓       ↓
(a)  BGAL_SULSO(SSβG)              425  WSLADNYEWASGFSMRFGLLKVDYN 450
     BGAL_SULSH                         WSLADNYEWASGFSMRFGLLKVDYN
     BGAL_SULAC                         WSLADNYEWSSGFSMRFGLLKVDYL
     BGAL_THEVO                         WSLADNYEWASGFSMRFGLLKVDYN
     β-Gal Pyrococcus furiosus          WSLTDNYEWAQGFRMRFGLVYVDFE
     β-Gly Agrobacterium tumefaciens    WSLMDNFEWAEGYRMRFGLVHVDYD
     BGLA_BACCI                         WSLMDNFEWAEGYGMRFGLVHVDYD
     BGLS_AGRSP                         WSLMDNFEWAEGYRMRFGLVHVDYQ
     β-Glc Rhizobium meliloti           WSLMDNFEWAEGYRMRFGIVHVDYE
     β-Glc Bacillus halodurans          WSLLDNFEWAEGYSMRFGIVHVNYR
     BGLA_PAEPO (BPβG)                  WSLLDNFEWAEGYNMRFGMIHVDFR
     β-Gal Pyrococcus woesei            WSLADNYEWASGFSMRFGLLKVDYN
(b)  β-Glc Dalbergia cochinchinensis    WSLLDNFEWAEGYTSRFGLYFVNYT
     Furostanol β-Glc Costus speciosus  WALTDNFEWDKGYTERFGLIYIDYD
(c)  LPH_HUMAN                          RSLIDGFEGPSGYSQRFGLHHVNFS
     MYR3_SINAL                         WALGDNYEFCKGFTVRFGLSYVNWD
(d)  LACG_STAAU(6-PBG)                  WSLMDVFSWSNGYEKRYGLFYVDFE
                                        *** ***↑↑  ** ↑****  :*::
```

MODIFIED CARBOHYDRATE PROCESSING ENZYME

This application claims the benefit of provisional Appln. No. 60/416,263 filed Oct. 7, 2002.

FIELD OF INVENTION

The invention relates to modified carbohydrate processing enzymes and their use in the hydrolysis of glycoside substrates and the synthesis of glycosides.

BACKGROUND TO THE INVENTION

Recent advances in the development of carbohydrate based therapeutics (Koeller and Wong, *Nat. Biotechnol.*, 18 (2000) 835-841), and the limitations of present chemical synthetic methods for producing oligosaccharides, has led to more novel approaches to the synthesis of carbohydrates and their conjugates (Davis, *J. Chem. Soc. Perkin Trans.*, 1 (2000) 2137). One approach to this problem is to carry out such syntheses using carbohydrate processing enzymes such as glycosyltransferases or glycosidases, as a valuable source of catalytic activity for the manipulation of unprotected carbohydrates (Crout and Vic, *Curr. Opin. Chem. Biol.*, 2 (1998) 98-11); Wymer and Toone, *Curr. Opin. Chem. Biol.*, 4 (2000) 110-119; Watt et al., *Curr. Opin. Chem. Biol.*, 7 (1997) 652-660; Kren and Thiem, *Chem. Soc. Rev.*, 26 (1997) 463-473; and Palcic, *Curr. Opin. Biotechnol.*, 10 (1999) 616-624). Glycosidases are simple, robust, soluble enzymes, and in general have been preferred for such glycosynthesis (Scigelova et al., *J. Mol. Catal. B Enzym.*, 6 (1999) 483-494 and Van Rantwijk et al., *J. Mol. Catal. B Enzym.*, 6 (1999) 511-532). Although catalysis of the hydrolysis of glycoside bonds is normally observed, glycosidases may be successfully used to synthesise glycosides through reverse hydrolysis (thermodynamic control) or transglycosylation (kinetic control with activated donors) strategies.

Thus far, improvements in glycosidase synthetic utility have largely focused upon developing new strategies for increasing low product yields (Mackenzie et al., *J. Am. Chem. Soc.*, 120 (1998) 5583-5584), improving regioselectivity of transfer (Prade et al., *Carbohydr. Res.*, 305 (1998) 371-381) or characterising available glycosidases for novel activities (Scigelova et al., supra). For example, a major advance in improving yields has been the development of the glycosynthase by Withers and co-workers (Mackenzie et al., supra; Mayer et al., *FEBS Lett.*, 466 (2000) 40-44, Malet and Planas, *FEBS Lett.*, 440 (1998) 208-212; Moracci et al., *Biochemistry* 37 (1998) 17262-17270, Trincone and Perugino, *Bioorg. Med. Chem. Lett.*, 10 (2000) 365-368; Fort et al., *J. Am. Chem. Soc.*, 122 (2000) 5429-5437; and Nashiru et al., *Chem. Int. Ed.*, 40 (2001) 417-420). These nucleophile-less glycosidase mutants are capable of glycosyl transfer in yields of up to 90% using glycosyl fluoride donors, but do not hydrolyse glycoside products and they illustrate well the benefits of glycosidase engineering for creating more synthetically useful catalysts.

An area of glycosidase engineering which has thus far been largely neglected is the engineering of new substrate specificities (Zhang et al., *Proc. Natl. Acad. Sci. USA.*, 94 (1997) 4504-4509; Andrews et al., *J. Biol. Chem.*, 275 (2000) 23027-23033; Kaper et al., *Biochemistry* 39 (2000) 4963-4970; and Rye and Withers, *Curr. Opin. Chem. Biol.*, 4 (2000) 573-580). Since the nature of the parent carbohydrate to be coupled to a given acceptor may be determined in synthesis simply through appropriate choice of donor, it is largely the stereoselectivity of a given glycosidase that we wish to exploit. An area of growing interest is that of combinatorial biocatalysis: the use of enzyme catalysts in parallel reactions to provide arrays of related molecules (Michels et al., *Trends Biotechnol.*, 16 (1998) 210-215; and Krstenansky and Khmelnitsky, *Bioorg. Med. Chem.*, 7 (1999) 2157-2162). In particular, the importance of gaining access to diverse arrays of glycoconjugates has recently been highlighted (Barton et al., *Nat. Struct. Biol.*, 8 (2001) 545-551). However, although combinatorial chemistry has revolutionized the approach to traditional chemical synthesis, the development of combinatorial biocatalysis has been hampered by the often stringent substrate specificities of synthetically useful enzymes.

SUMMARY OF THE INVENTION

The present invention provides a polypeptide having carbohydrate processing enzymatic activity, said polypeptide comprising an amino acid sequence selected from:

(a) the amino acid sequence of SEQ ID NO:2 comprising a mutation in at least one of W433, E432 or M439;

(b) the amino acid sequence of a family 1 glycosyl hydrolase, comprising at least one mutation at an amino acid residue equivalent to W433, E432 or M439 of SEQ ID NO: 2, and (c) a variant of (a) or (b) having carbohydrate processing enzymatic activity and comprising at least one amino acid mutation at a position equivalent to W433, E432 or M439 of SEQ ID NO: 2.

The present invention also provides for the use of a polypeptide of the invention in a method for:

(a) hydrolysis of one or more β-glycosides;

(b) glycoside synthesis of one or more β-glycosides; and/or (c) transglycosylation of a molecule.

The mutation is preferably a substitution of one of the above-identified amino acid residues with a cysteine (C) residue. The cysteine may be chemically modified so as to alter the electrostatic or steric environment within the active site and thereby alter the enzyme specificity.

The present invention further provides: a polynucleotide encoding a polypeptide of the invention; a vector comprising a polynucleotide of the invention; and a host cell transformed with a polynucleotide or vector of the invention.

BRIEF DESCRIPTION OF THE FIGURES

FIG. 1: Partial sequence alignment of the −1 binding pocket motif of *Sulfolobus solfataricus* β-glycosidase (SSβG) (Cubellis et al., supra) with high sequence similarity (left hand column gives SWISSPROT or TrEMBL annotation, numbering is that of SSβG); glycosidases with similar substrate specificity (a) to SSβG and glycosidases with different and/or broadened specificities in which E432 (d), W433 (c) and M439 (b, c, d) differ (marked with arrow and highlighted) (*Dalbergia cochinchinensis* β-glucosidase—Cairns et al., TREMBL Accession No. Q9SPK3; *Costus speciosus* furostanol-β-glycoside hydrolase—Inoue et al., *FEBS Lett.* 389 (1996) 273-277; LPH_HUMAN, human lactase phlorizin hydrolase—Mantei et al., *EMBO J.*, 7 (1988) 2705-2713; MY3_SINAL, myrosinase from Sinapsis alba—Xue et al., *Plant Mol. Biol.*, 18 (1992) 387-398; LACG_STAAU (6-PBG), *S. aureus* 6-phosphogalactosidase—Breidt and Stewart, *Appl. Environ. Microbiol.*, 53 (1987) 969-973). The amino acid sequences are presented as amino acids 425 to 450 of SEQ ID NO: 2 and SEQ ID NOS: 3 to 18.

BRIEF DESCRIPTION OF THE SEQUENCES

Figure 2:
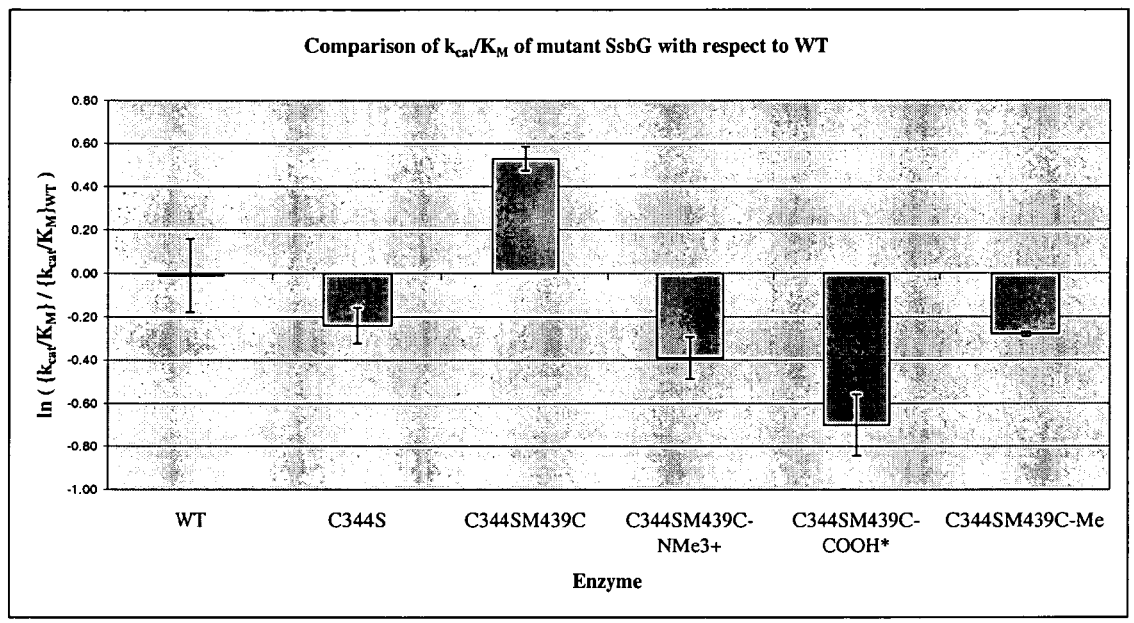
FIG. 2: Overall activity of chemically modified mutant enzymes (CMMs) with pNPGal relative to wild-type (WT) (average over 3 runs, except * average over 2 runs) with standard deviation error bars.

SEQ ID No 1 provides the amino acid sequence of the β-galactosidase of *Sulfolobus solfataricus* as well as the encoding polynucleotide sequence.

SEQ ID No 2 provides the amino acid sequence of the β-galactosidase of *Sulfolobus solfataricus*.

SEQ ID No 3 provides the amino acid sequence of the −1 binding pocket motif of the β-galactosidase of *Sulfolobus shibatae*.

SEQ ID No 4 provides the amino acid sequence of the −1 binding pocket motif of the β-galactosidase of *Sulfolobus acidocaldarius*.

SEQ ID No 5 provides the amino acid sequence of the −1 binding pocket motif of the β-galactosidase of *Thermoplasma volcanium*.

SEQ ID No 6 provides the amino acid sequence of the −1 binding pocket motif of the β-galactosidase of *Pyrococcus furiosus*.

SEQ ID No 7 provides the amino acid sequence of the −1 binding pocket motif of the β-glycosidase of *Agrobacterium tumefaciens*.

SEQ ID No 8 provides the amino acid sequence of the −1 binding pocket motif of the β-D-glucoside glucohydrolase of *Bacillus circulans*.

SEQ ID No 9 provides the amino acid sequence of the −1 binding pocket motif of the β-D-glucoside glucohydrolase of *Agrobacterium* sp.

SEQ ID No 10 provides the amino acid sequence of the −1 binding pocket motif of the β-glucoside of *Rhizobium meliloti*.

SEQ ID No 11 provides the amino acid sequence of the −1 binding pocket motif of the β-glucoside of *Bacillus halodurans*.

SEQ ID No 12 provides the amino acid sequence of the −1 binding pocket motif of the β-D-glucoside glucohydrolase of *Paenibacillus polymyxa*.

SEQ ID No 13 provides the amino acid sequence of the −1 binding pocket motif of the p-galactosidase glucohydrolase of *Pyrococcus woesi*.

SEQ ID No 14 provides the amino acid sequence of the −1 binding pocket motif of the β-glucoside of *Dalbergia cochinchinensis*.

SEQ ID No 15 provides the amino acid sequence of the −1 binding pocket motif of the Furostanol β-glucoside of *Costus specious*.

SEQ ID No 16 provides the amino acid sequence of the −1 binding pocket motif of the Lactase phlorizin hydrolase of *Homo sapiens*.

SEQ ID) No 17 provides the amino acid sequence of the −1 binding pocket motif of the Myrosinase of *Sinapis alba*.

SEQ ID No 18 provides the amino acid sequence of the −1 binding pocket motif of the 6-phospho-beta-galactosidase of *Staphylcoccus aureus*.

SEQ ID Nos 19 to 23 provide the nucleotide sequence of various oligonucleotide primers.

DETAILED DESCRIPTION OF THE INVENTION

The present invention provides a modified carbohydrate processing enzyme which shows an altered substrate specificity compared to the unmodified enzyme. Preferably, the alteration in substrate specificity leads to the enzyme accepting a broader range of substrates than the unmodified form.

The modified carbohydrate processing enzymes of the invention are typically produced by modifying a family 1 glycosyl hydrolase. In a preferred embodiment, the family 1 glycosyl hydrolase may be one isolated or originating from a thermophilic organism. For example, the enzyme may be from the thermophilic microbe *Sulfolobus solfataricus* and in particular may be a β-glycosidase from *Sulfolobus solfataricus*. Alternatively, the enzyme to be modified may be another member of the glycosyl hydrolase family 1 such as *Pyrococcus furiosus* β-glucosidase, *Dalbergia cochinchinensis* β-glucoside, *Costus speciosus* β-glycoside hydrolase, human lactase phlorizin hydrolase, myrosinase from *Sinapis alba* or *Staphylococcus aureus* phosphogalactosidase.

The amino acid sequence of β-glycosidase from *Sulfolobus solfataricus* is set out in SEQ ID NO:2. Variants in the sequence of SEQ ID NO: 2 may be present in β-glycosidase obtained from other isolates or strains of *Sulfolobus solfataricus* or other cell types expressing β-glycosidases or enzymes classified as being part of the glycosyl hydrolase family 1. Such variants may be modified in accordance with the invention. Carbohydrate processing enzymes, including family 1 glycosyl hydrolases and in particular P-glycosidases from other *Sulfolobus solfataricus* strains or other cell types expressing such enzymes can be isolated following standing cloning techniques, for example, using the polynucleotide sequence of SEQ ID NO: 1 or a fragment thereof as a probe. The isolated enzymes may then be modified.

Preferably, a polypeptide suitable for modification is one which has carbohydrate processing enzymatic activity prior to modification, although such activity may be restricted to specific substrates prior to modification. Typically, the modified carbohydrate processing enzyme of the invention will have glycosyl hydrolase, glycosyl synthase and/or transglycosylase activity. The enzyme may possess all three of these activities, any two of them or only one of them. In particular, the enzyme may have glycoside synthase activity or may hydrolyse glycoside substrates. The conditions the enzyme is being used under or the particular concentrations of substrates/products or their ratio may dictate which particular activity an enzyme of the invention displays or which activity predominates at a particular time. In particular, an activated substrate may be used to ensure synthase activity. Alternatively, or additionally, low water activity or sequence modifications may reduce or eliminate hydrolytic activity and allow glycosyl synthase and/or transglycosylase activity to predominate. The conditions and/or concentrations of substrate/products the enzyme of the invention is employed under may be manipulated to ensure that a particular desired activity or activities predominate.

An enzyme in accordance with the present invention is modified such that its activity is modified or increased in comparison to the unmodified form of the enzyme. In particular, the activity of the enzyme is altered to broaden the substrate specificity of the modified enzyme compared to its unmodified counterpart. In particular a modified enzyme of the invention may accept β-mannosides as a substrate, or other substrates not generally considered to be a natural substrate for the unmodified polypeptide.

The unmodified enzyme may accept a number of different substrates. However, the rate of reaction with different substrates may differ significantly. The unmodified enzyme may have higher affinity for a particular substrate, or subgroup of substrates, within the array of possible substrates that it can act on. The unmodified enzyme will therefore preferentially act on the high affinity substrate(s) even if low affinity substrates are also present at equivalent or higher concentrations. A modification in accordance with the invention may reduce the affinity of the enzyme for one or more of the higher affinity substrates, whilst having no, or little, effect on the affinity of the enzyme for its other substrates. The modifications therefore typically lead to a comparative increase in the activity for other substrates so that the rates of reaction with the variety of different substrates are more closely related and thus the enzyme has in effect a broader substrate specificity. The modified enzyme no longer acts preferentially on particular high affinity substrates but on a wider range of substrates.

The change in substrate specificity may relate to any or all of the activities of the enzyme. For example, it may relate to the hydrolase, synthase and/or transglycosylase activities of the enzyme and in particular to the hydrolase or synthase activities of the enzyme.

The $K_M$ for a particular substrate may be, for example, increased due to the introduction of the modification(s) of the invention by a factor of from 1.1 to 50 fold, preferably by a factor of from 3 to 40 fold, more preferably by a factor of from 5 to 25 fold and even more preferably by a factor of from 10 to 15 fold. This may be accompanied by reduction in $K_{CAT}$ by a factor of from 1.1 to 50 fold, preferably by a factor of from 3 to 40 fold, more preferably by a factor of from 5 to 25 fold and even more preferably by a factor of from 10 to 15 fold for the same substrate. The value of $K_{CAT}$ may be increased, for example, by a factor of from 1.1 to 250, preferably by a factor of from 2 to 200, more preferably by a factor of from 5 to 150, even more preferably by a factor of from 10 to 100 and still more preferably by a factor of from 20 to 75. These changes will typically be seen for a natural substrate of the enzyme and in particular for any of glucoside (Glc), galactoside (Gal), fucoside (Fuc), xyloside (Xyl) mannoside (Man) and/or glucuronide (GlcA) substrates. In particular, the changes will be seen with glucoside, galactoside, fucoside and/or mannoside substrates and preferably with glucoside and/or galactoside substrates. These changes may occur for any of the modifications of the invention, in particular for a modification at position 432 and/or 433 of SEQ ID No 2 or the equivalent residues. Preferably, these changes will occur for the modifications E432C and/or W433C or for the equivalent substitutions in other glycosyl hydrolases.

The substrate specificity of an enzyme in accordance with the invention can be monitored in vitro or in vivo, for example in accordance with the methods described in more detail below. In particular, assays can be carried out to monitor activity of the enzyme on particular substrates and in particular glycosidase substrates. Suitable substrates include glucosides, galactosides, fucosides, β-mannosides and β-glucuronides.

The assay may measure glycoside synthesis, hydrolysis and/or transglycosylation. Activity may be assayed using a chromophore such as, for example, paranitrophenol (PNP). The chromophore may be conjugated to a sugar as the carbohydrate donor molecule in glycoside synthesis or transglycosylation or as a substrate for hydrolysis. The release of the chromophore may be monitored to follow the course of the reaction and hence determine the activity of the enzyme. The release of leaving groups such as the fluoride ion, when a glycosyl fluoride is employed as a carbohydrate donor, may also be monitored to determine enzyme activity. The release of the fluoride ions may be measured using a fluoride electrode. Enzyme activity may also be monitored by using mass spectroscopy to monitor the formation of the product ion or decrease in the amount of the substrate ion.

In one aspect, an enzyme according to the present invention incorporates a mutation in at least one of the amino acid residues of 432 (glutamine), 433 (tryptophan) or 439 (methionine) of SEQ ID NO: 2. Alternatively the enzyme of the invention may be a family 1 glycosyl hydrolase comprising at least one mutation at an amino acid residue equivalent to W433, E432 or M439 of SEQ ID NO:2. The invention also encompasses variants of these sequences.

The mutation will typically be an amino acid substitution of W433, E432 or M439 or of the equivalent residues in other family 1 glycosyl hydrolases. Alternatively, the mutation may be a deletion comprising one or more of these residues or an insertion or duplication affecting these residues. Preferred modifications include mutation of the glutamine, tryptophan or methionine residues or their equivalents to cysteine. Replacement with other amino acids is also contemplated. For example, the residues may be replaced by alanine or valine. In cases where more than one amino acid substitution is made the amino acids introduced may be the same or different at some or all of the sites substituted. For example, the amino acids at positions 432, 433 and 439 may all be replaced with cysteine or with any combination of cysteine, alanine and/or valine.

The invention also relates to a variant of SEQ ID NO: 2 having an equivalent modification to those described above. A variant of SEQ ID NO: 2 may be a naturally occurring variant such as one selected from the family 1 of glycosyl hydrolases. A variant may also be a non-naturally occurring variant as described in more detail below. The equivalent amino acid to the residues at positions 432, 433 and 439 of SEQ ID NO: 2 can be identified by aligning a variant peptide with the sequence of SEQ ID NO: 2. The alignment is selected to provide the best possible match to SEQ ID NO: 2. The equivalent amino acid of any such variant to positions 432, 433 or 439 may then be identified and modified. FIG. 1 shows an alignment of the amino sequence of several family 1 glycosidases with the three residues equivalent to positions 432, 433 and 439 of SEQ ID No 2 highlighted. By performing similar alignments the equivalent residues can be identified in other family 1 glycosidases and variants and modified. Any of the programs discussed herein may be used to perform the alignment and in particular Clustal W based on BLOSUM 42.

The equivalent amino acid residues to residues 432, 433 and 439 of SEQ ID No 2 will generally be glutamine, tryptophan and methionine respectively. The equivalent amino acids may also be identified by molecular modelling to identify residues playing the equivalent roles to residues 432, 433 and 439 of SEQ ID NO: 2. Typically, such residues will interact with hydroxyl groups of the substrate. A modified polypeptide in accordance with the present invention may comprise one or more of the modifications described herein. Any combination of the modifications described herein may be present.

The carbohydrate processing enzymes of the invention may be further modified to eliminate their hydrolase activity. By replacing the active site catalytic nucleophile of a retaining glycosyl hydrolase it is possible to generate an enzyme which lacks hydrolytic activity, but which is still capable of glycoside synthesis using activated glycosyl donors such as α-glycosyl fluoride. Such mutated enzymes are known as glycosynthases. Existing glycosynthases may be modified in accordance with the invention to give an enzyme with altered substrate specificity. Alternatively, the nucleophilic residue of the active site of a family 1 glycosidase may be mutated at the same time that the other modifications of the invention are introduced.

Any amino acid may be substituted for the nucleophilic amino acid of the active site to generate a glycosynthase. Typically, the nucleophilic amino acid will be replaced by a non-nucleophilic residue. In particular, the nucleophilic residue may be substituted with a glycine, alanine or serine residue and preferably with a serine residue. The mutations Glu387Gly, Glu387Ala, Glu387Ser may be introduced into the sequence of SEQ ID No 2 to generate a glycosynthase or the equivalent mutation may be introduced in other family 1 hydrolases. The equivalent amino acid can be identified by the same means outlined here for identifying the equivalent residues to amino acids 432, 433 and 439 of SEQ ID No 2. Modelling and active site trapping, as well as sequence alignment, may also be used to identify the active site nucleophile which may then be mutated to eliminate the hydrolase activity of the enzyme.

As described above, a variant polypeptide having an amino acid sequence which varies from that of SEQ ID NO: 2 may be modified in accordance with the present invention. A variant for use in accordance with the invention is one having carbohydrate processing enzymatic activity. The variant may be, or be derived from, any family 1 glycosyl hydrolase A modified variant in accordance with the invention is one which preferably demonstrates a broader substrate base compared to a variant sequence not so modified.

In some cases the enzyme may recognise and act on the same substrates as the unmodified enzyme, but to all intents and purposes effectively have a broader substrate range. This is because the modification may make the affinities for various substrates more equivalent. Prior to modification the enzyme may have particularly high affinity for a small group of substrates out of the possible substrates it can act on. It will therefore preferentially act on that small group of substrates if present. However, post-modification the affinity for those substrates will be reduced and more equivalent to that of other potential substrates. The enzyme will therefore work on a wider range of substrates with equivalent activity.

A variant of SEQ ID NO: 2 may be a naturally occurring variant which is expressed by another strain of *Sulfolobus solfataricus* or other cell type. Such variants may be identified by looking for carbohydrate processing enzymatic activity in those cells which have a sequence which is highly conserved compared to SEQ ID NO: 2. Such proteins may be identified by analysis of the polynucleotide encoding such a protein isolated from an alternative strain, for example, by carrying out the polymerase chain reaction using primers derived from portions of SEQ ID NO: 2 or degenerate primes based on evolutionary conserved regions of SEQ ID NO: 2.

Variants of SEQ ID NO: 2 include sequences which vary from SEQ ID NO: 2 but are not necessarily naturally occurring carbohydrate processing enzymes. Over the entire length of the amino acid sequence of SEQ ID NO: 2, a variant will preferably be at least 30% homologous to that sequence based on amino acid identity. The variant may, for example, be at least 40% homologous, more preferably be at least 50% homologous and still mote preferably be more than 65% homologous to the amino acid sequence of SEQ ID NO: 2. In some embodiments the polypeptide will be at least 75% homologous, preferably at least 80% homologous and even more preferably the polypeptide is at least 85% homologous to SEQ ID NO: 2. The polypeptide may be at least 90% homologous and still more preferably be at least 95%, 97% or 99% homologous to the amino acid sequence of SEQ ID NO: 2. A variant may be a variant of any family 1 glycosyl hydrolase with one of the percentages of sequence homology specified above. In particular, a variant may be a variant of any of those proteins shown in FIG. 1 with any of the percentages of sequence homology specified herein to that sequence.

These percentages of homology may, for example, be over at least 30 amino acids, preferably over at least 40 amino acids and even more preferably over 50 amino acids. The percentages of homology may be over at least 75 amino acids, preferably at least 100, more preferably over 150 amino acids and in some cases will be over the entire length of the variant. In some cases they may be over all but 10, preferably all but 20, more preferably all but 30 and even more preferably all but 50 contiguous amino acids of the variant. There may be at least 80%, for example at least 85%, 90% or 95%, amino acid identity over a stretch of 40 or more, for example 60, 100 or 120 or more, contiguous amino acids ("hard homology").

In a preferred embodiment of the invention the variant will comprise a region which has one of the levels of amino acid sequence homology specified herein to amino acids 425 to 450 of SEQ ID No. 2. Alternatively, the variant may comprise a region which has such a degree of sequence homology to the equivalent region to amino acids 425 to 450 of SEQ ID No 2 from a different family 1 glycosyl hydrolase and in particular to one of such regions as depicted in FIG. 1.

Preferably sequence alignment and the determination of homology may be performed using ClustalW based on a BLOSUM42 matrix.

The variant may be one with any of the values of percentage homology mentioned herein to any of the proteins listed in FIG. 1 (either to the entire protein sequence of the protein or to the partial sequences shown in FIG. 1). The variant may be one of any family 1 hydrolase as long as one or more of the residues equivalent to 432, 433 or 439 has been modified.

Amino acid substitutions may be made to the amino acid sequence of SEQ ID NO: 2, for example from 1, 2 or 3 to 10, 20 or 30 substitutions. Such modifications may be introduced into any family 1 glycosyl hydrolase. Conservative substitutions may be made, for example, according to the following table. Amino acids in the same block in the second column and preferably in the same line in the third column may be substituted for each other:

| ALIPHATIC | Non-polar | G A P |
| | | I L V |
| | Polar - uncharged | S T M |
| | | N Q |
| | Polar - charged | D E |
| | | K R |
| AROMATIC | | H F W Y |

One or more amino acid residues of the amino acid sequence of SEQ ID NO: 2 may alternatively or additionally be deleted. From 1, 2 or 3 to 10, 20 or 30 residues may be deleted, or more. Polypeptides of the invention also include fragments (c) of the above-mentioned sequences. Such fragments retain carbohydrate processing enzymatic activity. Fragments may be at least from 10, 12, 15 or 20 to 60, preferably 100 or 200, 300 or more amino acids in length.

Such fragments may be used to produce chimeric enzymes using portions of enzyme derived from other carbohydrate processing enzymes such as, for example, glycosidases.

One or more amino acids may be alternatively or additionally added to the polypeptides described above. An extension may be provided at the N-terminus or C-terminus of the amino acid sequence of SEQ ID NO: 2 or polypeptide variant or fragment thereof. The, or each, extension may be quite short, for example from 1 to 10 amino acids in length. Alternatively, the extension may be longer. A carrier protein may be fused to an amino acid sequence according to the invention. A fusion protein incorporating the polypeptides described above can thus be provided.

Polypeptides of the invention may be in a substantially isolated form. It will be understood that the polypeptide may be mixed with carriers or diluents which will not interfere with the intended purpose of the polypeptide and still be regarded as substantially isolated. A polypeptide of the invention may also be in a substantially purified form, in which case it will generally comprise the polypeptide in a preparation in which more than 90%, e.g. 95%, 98% or 99%, by weight of the polypeptide in the preparation is a polypeptide of the invention.

Polypeptides of the invention may be modified for example by the addition of histidine residues to assist their identification or purification or by the addition of a signal sequence to promote their secretion from a cell where the polypeptide does not naturally contain such a sequence. It may be desirable to provide the polypeptides in a form suitable for attachment to a solid support. For example the polypeptides of the invention may be modified by the addition of a cysteine residue.

A polypeptide of the invention above may be labelled with a revealing label. The revealing label may be any suitable label which allows the polypeptide to be detected. Suitable labels include radioisotopes, e.g. $^{125}$I, $^{35}$s, enzymes, antibodies, polynucleotides and linkers such as biotin. Labelled polypeptides of the invention may be used in diagnostic procedures such as immunoassays in order to determine the amount of a polypeptide of the invention in a sample.

The proteins and peptides of the invention may be made synthetically or by recombinant means. The amino acid sequence of proteins and polypeptides of the invention may be modified to include non-naturally occurring amino acids or to increase the stability of the compound. When the proteins or peptides are produced by synthetic means, such amino acids may be introduced during production. The proteins or peptides may also be modified following either synthetic or recombinant production.

The proteins or peptides of the invention may also be produced using D-amino acids. In such cases the amino acids will be linked in reverse sequence in the C to N orientation. This is conventional in the art for producing such proteins or peptides.

A number of side chain modifications are known in the art and may be made to the side chains of the proteins or peptides of the present invention. Such modifications include, for example, modifications of amino acids by reductive alkylation by reaction with an aldehyde followed by reduction with NaBH$_4$, amidination with methylacetimidate or acylation with acetic anhydride.

The polypeptides of the invention may be introduced into a cell by in situ expression of the polypeptide from a recombinant expression vector. The vector may be stably integrated into the genome of the cell. The expression vector optionally carries an inducible promoter to control the expression of the polypeptide.

Such cell culture systems in which polypeptides of the invention are expressed may be used in assay systems.

A polypeptide of the invention can be produced in large scale following purification by high pressure liquid chromatography (HPLC) or other techniques after recombinant expression as described below.

The enzymes of the present invention are modified. By this it is meant that one or more amino acid sequence changes have been introduced into the enzyme in comparison to the unmodified sequence of the protein. Thus, typically a wild type enzyme will have had amino acid sequence changes introduced to produce the modified enzyme. The amino acid sequence changes introduced will affect amino acid positions 432, 433 and/or 439 of SEQ ID NO: 2 or the equivalent residues of other family 1 glycosyl hydrolases. The unmodified form of the enzyme will typically be the naturally occurring form of the enzyme. However, the amino acid substitutions of the invention may also be introduced into mutant and variant forms of family 1 glycosyl hydrolases.

In a preferred embodiment of the invention the enzyme is a modified form of β-galactosidase of *Sulfolobus solfataricus*, β-galactosidase of *Sulfolobus shibatae*, β-galactosidase of *Sulfolobus acidocaldarius*, β-galactosidase of *Thermoplasma volcanium*, β-galactosidase of *Pyrococcus furiosus*, β-glycosidase of *Agrobacterium tumefaciens*, β-D-glucoside glucohydrolase of *Bacillus circulans*, β-D-glucoside glucohydrolase of *Agrobacterium* sp., β-glucoside of *Rhizobium meliloti*, β-D-glucoside of *Bacillus halodurans*, β-D-glucoside glucohydrolase of *Paenibacillus polymyxa*, β-galactosidase glucohydrolase of *Pyrococcus* woesi, β-glucoside of *Dalbergia cochinchinensis*, Furostanol β-glucoside of *Costus specious*, Lactase phlorizin hydrolase of *Homo sapiens*, Myrosinase of *Sinapis alba*, or 6-phospho-beta-galactosidase of *Staphylcoccus aureus* which comprises one or more of the modifications of the invention. The −1 binding pocket for each of these enzymes is depicted in FIG. 1. The sequences are aligned to residues 425 to 450 of the β-galactosidase of *Sulfolobus solfataricus*. A modified polypeptide of the invention may comprise any of the sequences depicted in FIG. 1 into which one or more of the modifications of the invention have been introduced. A modified polypeptide of the invention may comprise a variant of such sequences.

The invention also relates to polynucleotides encoding the modified carbohydrate processing enzymes. A polynucleotide of the invention typically is a contiguous sequence of nucleotides which is capable of hybridising selectively with the coding sequence of SEQ ID NO: 1 or to the sequence complementary to that coding sequence. Polynucleotides of the invention include variants of the coding sequence of SEQ ID NO: 1 which encode the amino acid sequence of SEQ ID NO: 2. Such polynucleotides additionally incorporate one or more modification to encode a modified polypeptide as described in more detail above.

A polynucleotide for use in the invention and the coding sequence of SEQ ID NO: 1 can typically hybridize at a level significantly above background or alternatively the complement of such a sequence can. Background hybridization may occur, for example, because of other cDNAs present in a cDNA library. The signal level generated by the interaction between a polynucleotide of the invention and the coding sequence of SEQ ID NO: 1 is typically at least 10 fold, preferably at least 100 fold, as intense as interactions between other polynucleotides and the coding sequence of SEQ ID NO: 1. The intensity of interaction may be measured, for example, by radiolabelling the probe, e.g. with $^{32}$P. Selective hybridization is typically achieved using conditions of medium to high stringency (for example 0.03M sodium chloride and 0.003M sodium citrate at from about 50° C. to about 60° C.).

A nucleotide sequence capable of selectively hybridizing to the DNA coding sequence of SEQ ID NO: 1 or to the sequence complementary to that coding sequence will be generally be at least 30%, preferably at least 40% and even more preferably at least 50% homology to the coding sequence of SEQ ID No. 1. Sequence homology corresponds to sequence identity. In some embodiments it will be at least 60%, preferably at least 70% and more preferably at least 80%, homologous to the coding sequence of SEQ ID NO: 1 or its complement over a region of at least 20, preferably at least 30, for instance at least 40, 60 or 100 or more contiguous nucleotides or, indeed, over the full length of the coding sequence. Thus there may be at least 85%, at least 90% or at least 95% nucleotide identity over such regions.

Any combination of the above mentioned degrees of homology and minimum size may be used to define polynucleotides of the invention, with the more stringent combinations (i.e. higher homology over longer lengths) being preferred. Thus for example a polynucleotide which is at least 85% homologous over 25, preferably over 30, nucleotides forms one aspect of the invention, as does a polynucleotide which is at least 90% homologous over 40 nucleotides.

Nucleotide homology may be determined using various BLAST programs and in particular PSI-BLAST. Polynucleotide variants for use in the invention may be identified by performing PSI-BLAST searches of SWISSPROT and TREMBL to a family 1 glycosyl hydrolase, including any of those mentioned herein, and in particular to the amino acid sequence of SEQ ID No. 1.

Alternatively, the UWGCG Package provides the BEST-FIT program which can be used to calculate homology (for example used on its default settings) (Devereux et al (1984) Nucleic Acids Research 12, p 387-395). The PILEUP and BLAST algorithms can be used to calculate homology or line up sequences (such as identifying equivalent or corresponding sequences (typically on their default settings), for example as described in Altschul S. F. (1993) J Mol Evol 36:290-300; Altschul, S, F et al (1990) J Mol Biol 215:403-10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold (Altschul et al., supra). These initial neighborhood word hits act as seeds for initiating searches to find HSP's containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90: 5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

Polynucleotides of the invention may comprise DNA or RNA. They may also be polynucleotides which include within them synthetic or modified nucleotides. A number of different types of modification to polynucleotides are known in the art. These include methylphosphate and phosphorothioate backbones, addition of acridine or polylysine chains at the 3' and/or 5' ends of the molecule. For the purposes of the present invention, it is to be understood that the polynucleotides described herein may be modified by any method available in the art. The invention also includes protein nucleic acid (PNA) molecules comprising the sequences of the invention.

Polynucleotides of the invention may be used to produce a primer, e.g a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein. The invention also provides a microarray comprising such polynucleotides.

Polynucleotides such as a DNA polynucleotide and primers according to the invention may be produced recombinantly, synthetically, or by any means available to those of skill in the art. They may also be cloned by standard techniques. The polynucleotides are typically provided in isolated and/or purified form.

In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using PCR (polymerase chain reaction) cloning techniques. This will involve making a pair of primers (e.g. of about 15-30 nucleotides) to a region of the gene which it is desired to clone, bringing the primers into contact with DNA obtained from a suitable cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Although in general the techniques mentioned herein are well known in the art, reference may be made in particular to Sambrook et al., 1989.

Polynucleotides or primers of the invention may carry a revealing label. Suitable labels include radioisotopes such as $^{32}P$ or $^{35}S$, enzyme labels, or other protein labels such as biotin. Such labels may be added to polynucleotides or primers of the invention and may be detected using techniques known per se.

Polynucleotides of the invention can be incorporated into a recombinant replicable vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells are described below in connection with expression vectors.

Preferably, a polynucleotide of the invention in a vector is operably linked to a control sequence which is capable of providing for the expression of the coding sequence by the host cell, i.e. the vector is an expression vector. Such expression vectors can be used to express the polypeptide of the invention.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Multiple copies of the same or different modified carbohydrate processing enzyme genes may be introduced into the vector.

Such vectors may be transformed into a suitable host cell to provide for expression of a polypeptide of the invention. Thus, a polypeptide according to the invention can be obtained by cultivating a host cell transformed or transfected with an expression vector as described above under conditions to provide for expression of the polypeptide, and recovering the expressed polypeptide.

The vectors may be for example, plasmid, virus or phage vectors provided with an origin of replication, optionally a promoter for the expression of the said polynucleotide and optionally a regulator of the promoter. The vector may be an artificial chromosome such as a human or yeast artificial chromosome. The vectors may contain one or more selectable marker genes, for example a tetracycline resistance gene. Promoters and other expression regulation signals may be selected to be compatible with the host cell for which the expression vector is designed. Multiple copies of the same or different modified glycosidase gene in a single expression vector, or more than one expression vector each including a modified glycosidase gene which may be the same or different may be transformed into the host cell.

Host cells transformed (or transfected) with the polynucleotides or vectors for the replication and expression of polynucleotides of the invention will be chosen to be compatible with the said vector. In one embodiment of the invention lyophilized host cells are produced and used directly as biocatalysts.

The present invention also provides non-human animals comprising a polynucleotide encoding a modified enzyme of the invention. The non-human transgenic animal may, for example, be a rodent, such as a mouse or rat, or an animal such as a pig, sheep or cow. The invention also provides a plant comprising a polynucleotide encoding a modified polypeptide of the invention.

Where the amino acid at position 433, 432 or 439 is substituted by cysteine, the cysteine may be chemically modified so as to change the substrate specificity of the enzyme. The cysteine may be modified so as to comprise a positively-charged group, a negatively-charged group or an uncharged group. The positively charged group may be of formula —$(CH_2)n\text{-}N^+R_3$, wherein n is a positive integer from 1 to 4 and each R, which may be the same or different, is H or a $C_1$-$C_4$ alkyl group (preferably a methyl group). A preferred positively charged group is —$CH_2CH_2NMe_3^+$. The negatively-charged group may be of formula —$(CH_2)_n$—$SO_3^-$ or —$(CH_2)n\text{-}COO^-$, wherein n is a positive integer from 1 to 4. Preferably, the negatively-charged group is —$CH_2CH_2$—$SO_3^-$. The uncharged group may be a $C_1$-$C_4$ alkyl group and preferably is methyl.

An enzyme in accordance with the invention can be used in vitro, for example, bound to an immobile substrate. The enzyme can be immobilised through the addition of a binding sequence such as a His-tag or maltose binding site or by using a general immobiliser. The immobilised enzyme can then be used in the ring expansions and conversions described above.

The activity of a modified enzyme in accordance with the invention may be monitored by carrying out assays in vitro or in vivo, that is within a host cell, to monitor for carbohydrate processing activity of the enzyme. Such assays may include monitoring for the production of glycosides.

The modified enzymes in accordance with the present invention can be used in any methods involving glycosyl synthase, transglycosylase and/or hydrolase activity using glycoside substrates. They can be used wherever it is desired to a form β glycoside bond. In a particularly preferred aspect of the present invention, the enzymes are used in methods in which one or more glycoside substrates, such as one or more glucoside, galactoside, fucoside, mannoside or glucuronide substrates are incubated together with the modified enzyme. Preferably, the glycoside is β-mannoside. Preferably, in accordance with present invention more than one substrate is provided in the same reaction vessel to yield a library of different glycosides. Such substrates may include a natural substrate of the unmodified polypeptide and one or more non-natural substrates, that is substrates that are not usually accepted by the unmodified polypeptide. Thus methods may take advantage of the broadened substrate specificity of the enzymes of the invention to produce a variety of products in a single reaction vessel. Alternatively, reactions may be run in parallel using the enzyme of the invention where the only change between reactions is that a different substrate is employed and hence a different glycoside produced. Such reactions may be run in multiwell plates to allow for the individual screening of each glycoside produced in a high throughput assay.

The enzymes of the invention may be used in glycoside synthesis and in transglycosylation, they may also be employed in glycoside hydrolysis. Using the enzymes practically any β glycoside linkage may be synthesised or alternatively hydrolysed. In embodiments of the invention where the aim is glycoside synthesis the enzyme may be modified so that it is a glycosynthase i.e. the active site nucleophile will have been eliminated and replaced with an alternative amino acid. In such cases, typically the carbohydrate donor will be an activated donor such as a fluoryl or PNP linked carbohydrate donor. The enzyme catalyses the transfer of the glycoside, onto a chosen alcohol acceptor such as, for example another saccharide or polypeptide. In a preferred example, the glycosyl donor used is be a β-D-mannoside and it is used to form Man β(1,4) Glc NAc.

The enzymes of the invention may be used to generate an array of molecules conjugated to carbohydrates. They may be used to generate glycoproteins and in particular O-linked glycosylations, where typically the sugar group is conjugated to a serine or a threonine residue. The enzymes may be used to help produce recombinant proteins which have the same or similar glycosylations to naturally occurring versions of the proteins. The enzymes may be used to generate antibiotics and in particular macrolide antibiotics. They may be used in the food industry, for example to achieve depulping. They may also be used in detergents.

The enzymes may be used in therapy both as therapeutic molecules themselves and in the generation of therapeutic molecules. Thus the enzymes may be used in the treatment of a human or animal subject. The enzymes may be used in methods of treatment of the human or animal body by surgery or therapy.

The enzymes may be used to develop glycoconjugates for use in LEAP (lectin enzyme activated prodrug system). Lectins are found on the surface of cells. There are a variety of different lectins with certain ones only being found on a specific cell type or on specific groups of cell types. In LEAP glycoconjugates comprising a carbohydrate group capable of binding a specific lectin and an enzyme capable of activating a prodrug are generated and administered to a subject to which the prodrug is also given. The lectin binding group of the conjugate targets it to the specific cell type or types expressing the target lectin and hence the prodrug is only activated at the surface of the specific cell types. Thus LEAP allows drugs to be targeted to a specific class of cells through the lectins that they express and this can be used for a variety of functions including eliminating undesired cells. LEAP is described in WO 02/080980 which is incorporated herein by reference in its entirety. The enzymes of the invention can be employed in the production of any of the glycoconjugates described in WO 02/080980.

In glycoside synthesis using the enzyme of the invention the molecule glycosylated may be a saccharide or a different molecule such as a polypeptide. Multiple glycosylations of the same molecule may occur and, for example, di-, tri-, tetra or oligosaccharides may be generated. These may be generated, for example, by multiple step-wise glycosyl additions or by addition of an oligosaccharide to the target molecule. Branched oliosaccharides may also be added to a target molecule using the enzyme of the invention.

EXAMPLE 1

The binding domain of the thermophilic, retaining, exo-α-glycosidase, from *Sulfolobus solfataricus* (SSβG, EC 3.2.1.23) was probed using site directed mutagenesis. The gene encoding this enzyme, was originally isolated and sequenced from the *Sulfolobus solfataricus* strain MT4 (Cubellis et al., *Gene* (1990) 94, 89-94) and is classified as a member of the glycosyl hydrolase family 1 (Henrissat, (1991) *Biochem J.*, 280, 309-316). This robust, thermophilic enzyme is ideal (Pisani et al., *Eur. J. Biochem.* 187 (1990) 321-328, Moracci et al., *Protein Eng.*, 9 (1996) 1191-1195; and Nucci et al. *Biotechnol. Appl. Biochem.*, 17 (1993) 239-250). It can be routinely expressed in *Escherichia coli* (Moracci et al., *Enzym. Microb. Technol.*, 17 (1995) 992-997). Its 3D structure has a classic $(\alpha/\beta)_8$ TIM barrel (Banner et al., *Nature* 255 (1975) 609-614) containing a radial active site channel in a kink of the 5th α/β repeat (Aguilar et al., *J. Mol. Biol.*, 271 (1997) 789-802). Substrate specificity in this enzyme is associated with two residues in the binding site, glutamate 432 and methionine 439 which are largely conserved across family 1 glycosyl hydrolases (FIG. 1). Importantly, those family 1 hydrolases in which these residues differ also show altered substrate specificities (vide infra). In the examples below we have analyzed the structure of SSβG and created point mutants in which key residues implicated in specificity determination have been tailored. This results in robust mutant enzymes with altered substrate specificities and enhanced synthetic utility.

Materials and methods

Reagents, Enzymes and Bacterial Strains

The wild type sequence, lac S, encoding the β-glycosidase from *Sulfolobus solfataricus* (SsβG), was amplified by PCR from *Sulfolobus* genomic DNA, using the following primers:

5': CCATGGGACACCACCACCACCACCACCACTCAT-TAC (SEQ ID No.19)

3': CTCGAGTTAGTGCCTTTATGGCTTTACTGGAGG-TAC (SEQ ID No.20)

The 5' primer introduced an N-terminal Nco I site and a 6 x His tag immediately following the ATG initiation codon. The 3' primer introduced a Xho I site after the stop codon. The PCR product was cloned into pCR2.1 (Invitrogen) and individual clones were sequenced to verify that no errors had been introduced.

Electrocompetent *Escherichia coli* strain BL21(DE3) and His-bind Nickel resin were obtained from Novagen. 4-Methylumbelliferyl-β-D-glycoside substrates were purchased from Sigma. Pfu-turbo DNA polymerase was obtained from Stratagene and Nco I, Xho I restriction endonucleases, T4 DNA ligase from Promega, UK. Oligonucletoide primers were obtained from MWG BioTech GmBH and Cruachem Ltd. DNA sequencing was carried out by the DNA Sequencing Service, Dept. Biological Sciences, Durham, using standard protocols on Applied Biosystems DNA Sequencers.

Construction Selection and Screening of the Single Point Mutants

Mutations were introduced into the lac S gene coding sequence (in pCR2.1) according to the Stratagene Quick-Change mutagenesis system, using the suppliers' protocols. Oligonucleotide primers used for the generation of the point mutations were:

for Glu-432→Cys;

5'TCTAGCTGATAATTACTGTTGGGCTTCAGGATTCT-3' (SEQ ID NO: 21);

for Trp-433→Cys;

5'-CTAGCTGATAATTACGAATGTGCTTCAGGAT TCTC-3' (SEQ ID NO: 22);

for Met-439→Cys;

5'-GCTTCAGGATTCTCTTGTAGGTTTGGTCTG-3'(SEQ ID NO: 23)

along with the corresponding complementary primers. Individual point mutations were verified by DNA sequence analysis. Wild type and mutated coding sequences were cloned into the Nco I/Xho I sites of expression vector pET-24-d(+) (Novagen) and transformed into *E. coli* BL21(DE3). Putative transformants were identified by colony PCR using the SSβG coding sequence primers. Selected clones were checked by DNA sequencing to confirm the mutation, and the absence of unintended PCR-introduced base changes.

Overexpression and Purification of the $His_6$ Tagged Mutant Enzymes

Selected clones were grown in LB medium containing kanamycin (50 µg/ml), at 37° C. to an O.D. of 0.6 at 600 nm, and the target were proteins induced by the addition of 0.1M IPTG. Cells were harvested by centrifugation, resuspended in $\frac{1}{10}^{th}$ volume of column loading buffer (5 mM imidazole, 20 mM Tris, 0.5M NaCl, pH 7.8), and lysed using a Soniprep 150 Sonicator. The suspension was recentrifuged to pellet cell debris (10000 rpm, 30 min), and the $His_6$-tagged recombinant proteins were purified from the supernatant using Ni-chelation chromatography (wash buffer, 60 mM imidazole, 20 mM Tris, 0.5M NaCl, pH 7.8, elution buffer 300 mM imidazole, 20 mM Tris, 0.5M NaCl, pH 7.8). The eluted protein peak was dialysed against 50 mM sodium phosphate buffer, (pH 6.5), and stored at 4° C. Protein concentration was quantified by the method of Bradford 1976 *Anar Biochem.*, 151, 196-204 (reagents from Biorad, Netherlands). Purified proteins were analysed by SDS-polyacrylamide gel electrophoresis, gel fitration chromatography and ESMS (Micromass LCT, ±8Da).

Characterisation of the Kinetic Properties of Enzymes

Parameters were determined by the method of initial rates. Activity was measured in time course assays of the hydrolysis of 4-methylumbelliferyl-β-D-glycosides (β-D-gluco, β-D-galacto, β-D-fuco, β-D-manno, β-D-xylo, β-D-glucurono) at 5-15 concentrations (0.001-1.5 mM) incubated at 80° C. in 50 mM sodium phosphate buffer, pH 6.5. Reactions were terminated at 2, 5, 10, 15 min by the addition of 100 µl of ice cold 1M $NazCO_3$, pH 10 and analyzed (Labsystems Fluoroscan Ascent plate reader, excitation 460 mm, emission 355 nm). $K_M$ and $k_{cat}$ were derived by fitting the initial rates to hyperbolic Michaelis-Menten curves using GraFit 4 (Erithacus Software Ltd, Staines, UK).

Sequence Analysis

Sequence alignment was performed using ClustalW based on a BLOSUM42 matrix. Enzymes of interest were determined by their sequence similarity using PSI-BLAST searches of SWISSPROT and TREMBL to BGAL_SULSO (SSβG), *Sulfolobus solfataricus* β-glycosidase (SSβG) (Cubellis et al., supra) including, *Pyrococcus furiosus* β-glucosidase (CelB) (PFβG) (Voorhurst et al., *J. Bacteriol* (1995) 177, 7105-7111) used for molecular mechanics analysis. In this way several glycosidases were also identified with both altered substrate specificity and differences in the residues occupying positions 432, 433 and 439 (SSβG numbering): *Dalbergia cochinchinensis* Dalcochinin-8'-O-β-glucoside β-glucosidase (Cairns et al., supra, TREMBL accession No. Q95PK3); *Costus speciosus* furostanol-26-O-p-glycoside hydrolase (Inoue et al FEBS letters 1996 389, 273-277; LPH_HUMAN, human lactase phlorizin hydrolase (Mantei et al., Supra); MY3_SINAL, myrosinase from Sinapis alba (Xue et al., supra); LACG_STAAU (6-PBG), *S. aureus* 6-phosphogalactosidase (Breidt and Steward, supra).

Molecular Mechanics and Docking Analysis

The X-ray structure of SS G (CSB-PDB entry 1 gow) was used as the starting point for calculations. The enzyme setup was performed with Insight II, version 2.3.0 (Accelerys Inc. San Diego, Calif., USA). To create initial coordinates for the minimization, hydrogens were added at the pH used for kinetic measurements (6.5). The model system was solvated with a 5 Å layer of water molecules. Energy simulations were performed with the DISCOVER module within Cerius2, Version 3.8 on a Silicon Graphics Indigo computer, using the consistent valence force field (CVFF) function. A non-bonded cutoff distance of 18 Å with a switching distance of 2 Å was employed. The non-bonded pair list was updated every 20 cycles and a dielectric constant of 1 was used in all calculations. Docked structures were generated using the Builder module, and aligned within the active site using appropriate bump, hydrogen bonding and docking interaction monitors. The enzyme was then minimized in stages, with initially only the water molecules being allowed to move, followed by water molecules and the amino acid side chains, and then finally the entire enzyme. The β-D-Glcp was free to move throughout all stages of the minimization. Each stage of energy minimization was conducted by means of the method of steepest descents without Morse or cross terms until the derivative of energy with respect to structural perturbation was less than 5.0 kcal/Å; then the method of conjugate gradients, without Morse or cross terms until the derivative of energy with respect to structural perturbation was less than 1.0 kcal/Å; and finally the method of conjugate gradients, with Morse and cross terms until the final derivative of energy with respect to structural perturbation was less than 0.1 kcal/Å.

Glycoside Synthesis

Enzyme (WT, W443C or E432C, 1 mg) was added to a mixed solution (1 mL) of para-nitrophenyl (pNP) β-D-manno-, galacto-, gluco- and xylo- pyranosides (0.03 mmol of each) in 1:9 MeOH:phosphate buffer (pH 6.5) and incubated at 50° C. for 45 min (WT), 4 h (WT), 8 h (W433C, E432C). After this time the solutions were extracted with EtOAc to remove para-nitrophenol and passed through short Sephadex and Celite:Graphite (1:1) columns to remove protein, pNP-glycoside and remaining para-nitrophenol. Solvent was removed and product mixtures were analysed by $^1$H NMR and ESMS. Yields based on donor were calculated from integration of anomeric proton resonances in $^1$H NMR ($D_2O$, 500 MHz): α-Gal (δ 5.12, d, 14.0 Hz), α-Glc (δ 5.08, d, 3.8 Hz), α-Xyl (δ 5.04, d, J=3.4 Hz), α-Man (δ 5.03, d, J=1.8 Hz), β-Man (δ 4.75, s), β-Glc (δ 4.49, d, J=8.0 Hz), P-Gal (δ 4.45, d, 7.9 Hz), Me-β-Man (δ 4.44, s), β-Xyl (δ 4.42, d, J=7.8 Hz), Me-β-Glc (δ 4.23, d, J 8.1 Hz), Me-β-Xyl (δ 4.18, d, J=7.8 Hz), Me-β-Gal (δ 4.17, d, J=8.0 Hz).

Results

Analysis of the Binding Site of SSβG

In an attempt to dissect the specificity determining interactions of SSβG with its substrates we examined the 3D structures of SSβG (RCSB-PDB 1gow) and the close structural homologue B. *polymyxa* β-glycosidase (BPβG). Valuably, 3D structures of BPβG containing D-gluconate bound as a substrate mimic (1bgg) and a 2-deoxy-2-fluoro-α-D-glucosyl-enzyme intermediate have recently been reported. This allowed homology modelling and docking analysis of SSβG to create a minimum energy structure through molecular mechanics containing β-D-glucopyranose as a substrate mimic. Both the structures of BPβG and SSβG showed that the conserved residues E432 and W433 (SSβG numbering) (FIG. 1) create vital hydrogen bonds to the OH-4 and 3, respectively, of their substrates. Furthermore, M439 sits at the base of the small side pocket that lies in close proximity to OH-6. Gratifyingly, sequence analysis (FIG. 1) supports the identification of the potential of these residues in specificity determination: e.g., S432 (SSβG numbering) rather than E432 in the phosphogalactosidase (E.C. 3.2.1.85) from *S. aureus* (Breidt and Stewart, supra), and G433 rather than W433 in the broad specificity glycosidase/cerebrosidase human lactase phlorizin hydrolase (E.C. 3.2.1.62) (Mantei et al., supra).

We therefore selected E432, W433 and M439 for mutagenesis as potentially critical active site residues for determining substrate specificity. Cysteine was chosen as the target residue for mutations, as a single flexible residue that could play a variety of roles C behaves in proteins similarly to W and M, is structurally close to S but would alter some of the key interactions identified (e.g., abolish hydrogen bonding) in a conservative, informative manner.

Construction and Kinetic Characterisation of WT and Mutant Enzymes

SSβG-WT, -E432C, -W433C and -M439C enzymes were expressed in *E. coli* as recombinant proteins containing an N-terminal His$_6$-tag to avoid interfering with the critical multimer-forming interactions of the C-terminus of the protein. Yields of recombinant protein were of the order of 15 mg per liter of culture. The purified, recombinant WT and mutated SSβG proteins gave single bands on SDS-PAGE at an indicated approx mol. wt. of 57,000, and gave a single peak on analysis by gel filtration under non-denaturing conditions, of an indicated molecular weight consistent with the formation of dimeric molecules (data not presented). Exact masses were confirmed by ESMS (±8 Da). Both WT and mutant recombinant SSβGs were >95% pure by these analyses.

Determination of the Michaelis-Menten parameters for the WT and mutant enzymes was performed at pH 6.5 at 80° C. for a broad range of representative, fluorophore-containing 4-methylumbelliferyl glycoside substrates, which allowed activities to be determined with a high degree of sensitivity (Table). Under these optimized assay conditions, the glucoside (Glc), galactoside (Gal) and fucoside (Fuc) substrates were hydrolysed well by SSβG-WT, but the xyloside (Xyl) substrate was hydrolysed relatively poorly (approx. 3% of turnover as determined by $k_{cat}$ compared with β-D-glucoside). Interestingly, low levels of previously undetected β-D-mannoside (Man) and β-D-glucuronide (GlcA) activities (approx. 1% and 0.5% of turnover towards β-D-glucoside) were observed. In all cases the absolute D-stereospecificity and β-stereoselectivity of SSβG was maintained and no activity was detected towards L- or α-glycoside substrates.

| Substrate | Enzyme, SSβG- | $K_m$, mM | $k_{cat}$, $s^{-1}$ | $k_{cat}/K_m$, $s^{-1}mM^{-1}$ |
|---|---|---|---|---|
| 4-MUGlc | WT | 0.046 ± 0.017 | 140 ± 20 | 2900 |
| | E432C | 0.34 ± 0.07 | 5.1 ± 0.5 | 15 |
| | W433C | 1.61 ± 0.35 | 33 ± 5 | 20 |
| | M439C | 0.068 ± 0.028 | 190 ± 40 | 2900 |
| 4-MUGal | WT | 0.066 ± 0.017 | 98 ± 7 | 1490 |
| | E432C | 0.47 ± 0.14 | 5.4 ± 0.8 | 11 |
| | W433C | 2.2 ± 1.2 | 14 ± 6 | 6.3 |
| | M439C | 0.083 ± 0.016 | 94 ± 11 | 1130 |
| 4-MUFuc | WT | 0.011 ± 0.002 | 80 ± 2 | 7300 |
| | E432C | 0.34 ± 0.04 | 18 ± 1 | 53 |
| | W433C | 0.41 ± 0.09 | 31 ± 3 | 76 |
| | M439C | 0.023 ± 0.005 | 91 ± 8 | 4000 |
| 4-MUMan | WT | 0.036 ± 0.009 | 1.8 ± 0.2 | 50 |
| | E432C | 0.90 ± 0.26 | 2.8 ± 0.7 | 3.2 |
| | W433C | 0.18 ± 0.02 | 0.92 ± 0.05 | 5.1 |
| | M439C | 0.042 ± 0.015 | 2.3 ± 0.4 | 53 |
| 4-MUXyl | WT | 0.13 ± 0.03 | 3.8 ± 0.3 | 30 |
| | E432C | 1.26 ± 0.21 | 2.8 ± 0.3 | 2.2 |
| | W433C | 0.59 ± 0.19 | 1.5 ± 0.3 | 2.5 |
| | M439C | 0.068 ± 0.007 | 9.3 ± 0.2 | 136 |
| 4-MUGlcA | WT | 1.3 ± 0.4 | 0.81 ± 0.18 | 0.60 |
| | E432C | $NAD^a$ | NAD | NAD |
| | W433C | NAD | NAD | NAD |
| | M439C | 1.4 ± 0.6 | 1.3 ± 0.4 | 0.92 |

It is apparent that the E432C and W433C mutations have a dramatic effect upon activity towards certain substrates. Glc $k_{cat}/K_M$ is reduced 200-fold and 140-fold, and Gal $k_{cat}/K_M$ is reduced 130-fold and 230-fold for E432C and W433C respectively. However, although Man, Xyl activities were also reduced, these reductions were far less marked to $k_{cat}/K_M$ values only 10-16-fold lower than WT for E432C and W433C. Consistent with the prediction that hydrogen bonds to OH-4 (E432C) and OH-3 (W433C) are abolished in these mutants, these $k_{cat}/K_M$ decreases correspond to a loss of affinity of approx. 4.5-10.5 kJ mol$^{-1}$. These reductions in $k_{cat}/K_M$ were largely manifested in reductions in ground state binding with $K_M$ values generally increased up to 37-fold; the greatest $K_M$ increases in both W433C and E432C were observed for Glc, Gal, Fuc. Variations in $k_{cat}$ in the mutants E432C and W433C were less uniform; there were large overall reductions in Gal,Glc turnover ($k_{cat}$ decreased by approx. 5- to 30-fold), whereas $k_{cat}$ for Fuc, Xyl, Man in E432C and W433C are essentially similar to those for SSβG-WT (2-fold increased $k_{cat}$ (Man) for E432C to only 2.9-fold lowered $k_{cat}$ (Xyl) for W433C). This indicates that an additional transition state destabilisation is induced by mutation in E432C and W433C that essentially affects Gal,Glc only.

We were pleased to discover that as a result of the varying alterations in $k_{cat}/K_M$ for different substrates the specificities of E432C and W433C were remarkably more broad than SSβG-WT. For example, the variation of $k_{cat}/K_M$ for Glc:Gal:Xyl:Man moves from a restrictive 100-fold specificity range for WT to a broad 8-fold range for W433C (WT, 100:52:1:2→W433C, 8.1:2.5:1:2).

The M439C mutation has a more subtle effect on specificity than the E432C and W433C mutations. Consistent with the ability of M439 to modulate substrate C-6 substituent specificity suggested by molecular modelling, the level of $k_{cat}/K_M$ alteration caused by mutation differs according to C-6 structure. M439C shows almost identical values to WT for Gal, Glc, Man substrates in which the CH$_2$OH at C-6 is unaltered. However, $k_{cat}/K_M$ for Fuc, which instead bears a CH$_3$ at C-6, is 1.8-fold lower than WT and excitingly, $k_{cat}/K_M$ for Xyl, which bears no C-6 substituent, is 4.7-fold higher than WT. It should also be noted that, the mutation has the effect of increasing $k_{cat}$ for all the substrates, suggesting that a general stabilisation of the transition states is occurring.

It has been proposed previously that in other family 1 glycosidases the position corresponding to E432 in SSβG is responsible for the modulation of carbohydrate substrate O-6 substituent binding and in particular the rejection of negatively charged substituents (Aguilar et al., supra). Contrary to this prediction, the E432C mutant has no detectable activity towards GlcA, which at pH 6.5 bears a negative charge at C-6. In contrast, M439C shows slightly enhanced $k_{cat}/K_M$ values for GlcA (1.5-fold higher than WT), also consistent with modulation of C-6 substituent binding by M439.

Improved Biocatalytic Breadth of W433C

Valuably, SSβG-WT's very high initial activity at 80° C. resulted in enzymes that were still usefully active even after overall reductions in $k_{cat}/K_M$ caused by mutation to E432C and W433C. For example, W433C displays a $k_{cat}/K_M$ towards β-Gal substrates (6.3 s$^{-1}$ mM$^{-1}$) that compares well with the activity of recently described enhanced glycosynthases ($k_{cat}/K_M$ 0.013 s$^{-1}$ mM$^{-1}$) (Mayer et al., supra). This activity coupled with greatly broadened specificity resulted in a synthetic utility for W433C and E432C that was demonstrated by the parallel synthesis of β-glycosides of Glc,Gal,Xyl,Man within in a one pot mixture (Scheme 1).

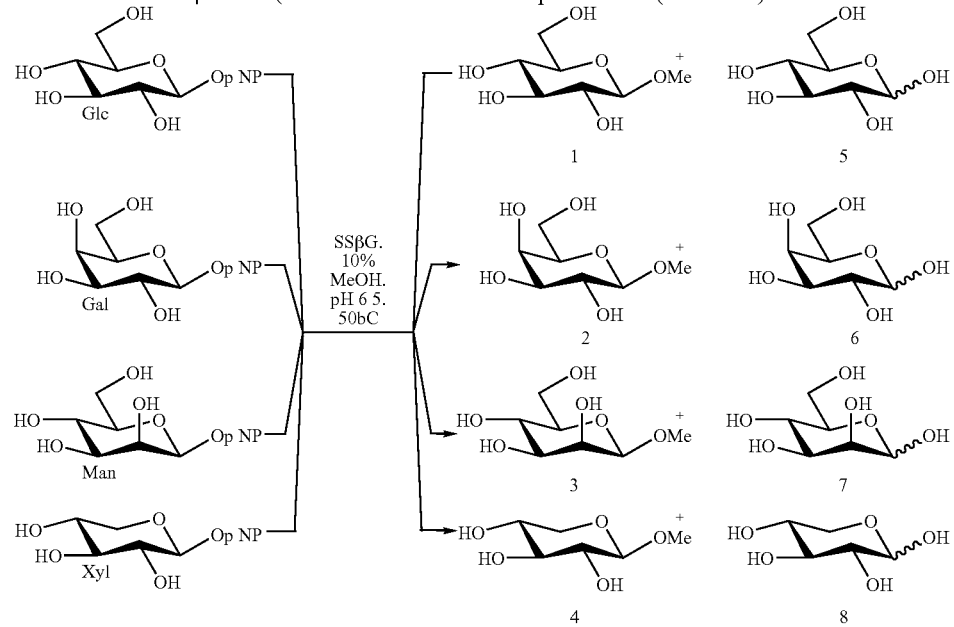

-continued

| SSβG | Time | 1 | 2 | 3 | 4 | 5 | 6 | 7 | 8 |
|---|---|---|---|---|---|---|---|---|---|
| WT | 45 min | 40 | 33 | 2 | 3 | 14 | 8 | - | - |
| WT | 4 h | - | - | 8 | 20 | 33 | 30 | 4 | 5 |
| E432C | 8 h | 22 | 24 | 14 | 17 | 7 | 9 | 3 | 4 |
| W433C | 8 h | 36 | 18 | 8 | 13 | 11 | 6 | 3 | 5 |

Scheme 1: Parallel glycoside syntheses using SSβG-WT, -E432C and -W433C as catalysts. The corresponding yields of products (each compound formed is labelled 1-8) are shown in the table. These show that E432C and W433C mutants of SSβG, in which substrate specificity has been tailored, successfully produced balanced libraries of the four, desired β-glycosides of Glc (1), Gal (2), Man (3) and Xyl (4). Such balanced libraries are not produced by SSβG-WT even under varying reaction times.

SSβG-WT was robust enough to catalyze transglycosylation at 50° C. in 1:9 MeOH:buffer solutions, to form β-glycosides. However, its stringent specificity meant that after short periods (45 min) only glucoside 1 and galactoside 2 were formed and although small amounts of mannoside 3 and xyloside 4 were observed after extended periods (4 h), by this time all initially formed 1 and 2 had been hydrolysed. SSβG-WT is therefore incapable of creating libraries of glycosides in this way. We were therefore delighted to find that both W433C and E432C yielded mixtures of methyl Glc,Gal,Xyl, Man glycosides 1-4. Indeed, the tailoring of E432C's specificity is so successful that it catalyzes the formation of a small library of 1-4 in which each component is present in near equal amount. This balanced and similar yield of each of 14 mirrors the very similar $k_{cat}$ values (2.8-5.4 s$^{-1}$) of E432C for Glc,Gal,Xyl,Man substrates, an observation that is consistent with the high (>$K_M$) concentrations of substrates used in these reactions.

Success was achieved in tailoring the specificity of SSβG to create catalysts of broad synthetic utility. The handful of previous examples of substrate specificity alterations in glycosidases have only involved tailoring towards or away from functional groups such as CH$_2$OH (Zhang et al., supra and Andrews et al., supra) or phosphate (Teaper et al., Supra). Excitingly, our results suggest that tailoring of stereospecificity is also possible. For example, alteration of a single residue W433→C effectively broadened the Gal:Man stereospecificity 25-fold from 29.4:1 in SSβG-WT to 1.2:1 in SSβG-W433C. Similarly, in the M439C mutant the sum of specificity alteration effects, including a 5-fold absolute increase in Xyl activity, causes a 10-fold increase in Xyl over Fuc specificity. The power of these mutant enzymes was further demonstrated by their utility in one-pot parallel syntheses of small arrays of glycosides that could not be accomplished with WT enzyme.

EXAMPLE 2

1. Summary

In recent years, chemists have used enzymes such as glycosidases in glycosynthesis (Crout, D. H. G. and Vic, G., *Curr. Opin. Struct Biol.* 2, 98-111 (1998)), and they are attractive biocatalysts. Research has focussed on site-directed mutagenesis alone as a means of modifying glycosidase activity (Kaper, T., Lebbink, J. H. G., Pouwels, J., Kopp, J., Schulz, G. E., van der Oost, J., and de Vos, W. M., *Biochemistry,* 39, 4963-4970 (2000)), but the construction of mutants is a lengthy process and it is recognised that having a rapid tool for protein modification would be advantageous.

This work, inspired by research conducted on an alkaline protease (Matsumoto, K., Davis, B. G., and Jones, J. B., *Chem. Eur. J.* 8, 4129-4137 (2002)), investigates the combined strategy of site-directed mutagenesis and chemical modification as a means of tailoring the specificity and activity of *Sulfolobus solfataricus* β-glycosidase (SsβG).

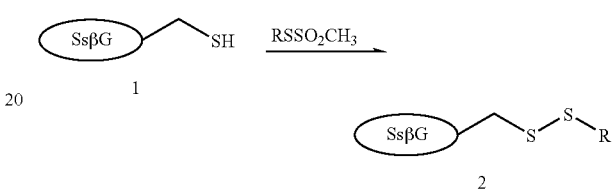

Chemical modification of a cysteine residue in the active site (1) with methanethiosulfonate reagents (3,4) allowed the facile introduction of functional groups (R) to form mutants (2) with modified electrostatic and steric environments within the active site.

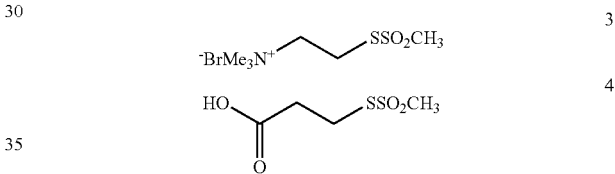

Modelling of the enzyme active site suggested the synthesis of substrates possessing charged groups at the C-6 hydroxyl (5,6) to probe the interaction with charged groups present in the chemically modified mutants.

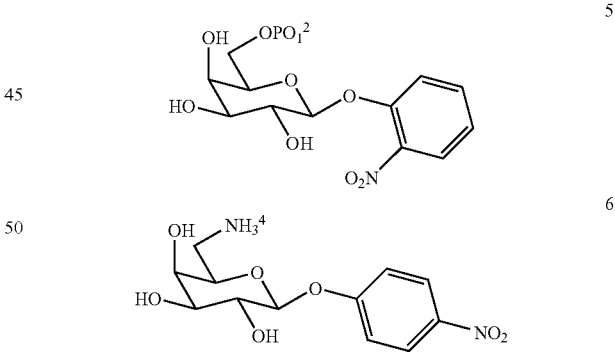

The kinetic activity of the mutant enzymes was assessed using ultra-violet/visible spectroscopy and demonstrated that glycosidase activity can be tailored by the combined strategy of site-directed mutagenesis and chemical modification. Initial results suggest that the steric environment of the active site has a greater effect on enzyme activity and specificity than the electrostatic environment.

2. Results and Discussion

The work falls broadly into three categories—preparation of chemically modified mutants (CMMs) via synthesis of methanethiosulfonate reagents and subsequent chemical modification of C344SM439C, synthesis of substrate molecules and investigation into the kinetics of WT, C344S, C344SM439C and CMMs with various substrates.

2.1 Preparation of Chemically Modified Mutants 2.1.1 Synthesis of Methanethiosulfonate Reagents 2.1.1.1 Synthesis of Sodium Methanethiosulfonate The synthesis of sodium methanethiosulfonate 21, precursor to functionalised MTS reagents, was achieved by refluxing elemental sulphur and methane sulfinic acid sodium salt 20 in anhydrous methanol (D. Gamblin Part II Thesis, University of Oxford). The insertion reaction proceeded smoothly in a yield of 73% (Scheme 1).

Scheme 1

$$CH_3SO_2Na + S \xrightarrow{(i)} CH_3SO_2SNa$$
$$20 \quad\quad\quad\quad\quad\quad 21$$

(i) anhydrous methanol, reflux, 20 min, 73%

2.1.1.2 Synthesis of 2-carboxyethyl Methanethiosulfonate

This synthesis was achieved following the synthetic route to the analogous 4-carboxybutyl methanethiosulfonate (Davis, B. G., Shang, X., DeSantis, G., Bott, R. R., and Jones, J. B., *Bioorg. Med. Chem.* 7, 2293-2301 (1999)). The reaction proceeded smoothly in a yield of 64% (Scheme 2).

Scheme 2

(i) anhydrous DMF, 70° C., 2 h, 64%

2.1.1.3 Synthesis of 2-(trimethylammonium)ethyl Methanethiosulfonate Bromide

Following literature procedure (Davis, B. G., Khumtaveeporn, K., Bott, R. R., and Jones, J. B., *Bioorg. Med. Chem.* 7, 2303-2311 (1999)) the reaction proceeded in a 36% yield (Scheme 3).

Scheme 3

(i) annydrous methanol, reflux, 48 h, 36%

2.1.2 Chemical Modification of C344SM439C 2.1.2.1 Resuspension of C344SM439C

Chemical modification of C344SM439C was initially attempted using the procedure employed in the chemical modification of SBL which has been developed in our group. However, attempts to resuspend the protein in standard modification buffer (70 mM CHES, 5 mM MES, 2 mM $CaCl_2$, pH 9.5) were unsuccessful, resulting in protein precipitation. Subsequent Bradford testing (Bradford, M. M., *Anal. Biochem.* 72, 248-254 (1976)) of the protein left in solution showed low protein concentration.

From previous work conducted in the group it was known that WT SsβG and subsequent mutants resuspend well without precipitation in phosphate buffer and show activity therein. Previous kinetic investigtions carried out within the group on SsβG mutants had been conducted at pH 6.5. However, the modification reaction proceeds faster at higher pH values. The upper pH limit of phosphate buffer is pH 9.0 and so this was an imposed limitation on the ligation conditions. Given these considerations, it was necessary to find a compromise ligation pH value—one which was high enough to encourage rapid modification but which would not be so high as to damage the protein. Accordingly, resuspension of C344SM439C was attempted in phosphate buffer at values of pH 6.24, pp 77.68, 8.32 and 8.86 and Bradford testing conducted on the resulting protein solutions.

TABLE 1

| Resuspension of C344SM439C | |
|---|---|
| pH | Protein concentration/mgmL$^{-1}$ |
| 6.24 | 0.71 |
| 7.68 | 0.94 |
| 8.32 | 0.84 |
| 8.86 | 0.94 |

The Bradford test is only considered accurate to within ~10%, as it relies on the assumption that the test protein will bind to the dye to the same degree as the standard protein, BSA. Table 1 shows the protein concentration determined in each of the resuspension buffers.

2.1.2.2 Chemical Modification Reaction

To investigate the effect of the ligation pH, the first chemical modification experiment to introduce a trimethyl-ammonium group into position 439 in the active site was carried out at both pH 7.68 and pH 8.86 (Scheme 4).

Scheme 4: Chemical modification (i) $MeSO_2SCH_2CH_2NMe_3{}^+Br^-$, ~3h, pH 7.68 or 8.86

The literature method for monitoring the ligation reaction is by use of Ellman's reagent (Fierobe, H.-P., Mirgorodskaya, E., McGuire, K. A., Roepstorff, P., Svensson, B., and Clarke, A. J., *Biochemistry*, 37, 3743-3752 (1998)), which reacts with free thiols to release a yellow chromophore visible to the naked eye (Scheme 5).

Scheme 5: Mechanistic action of Ellman's reagent

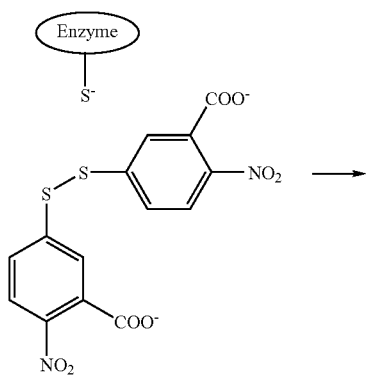

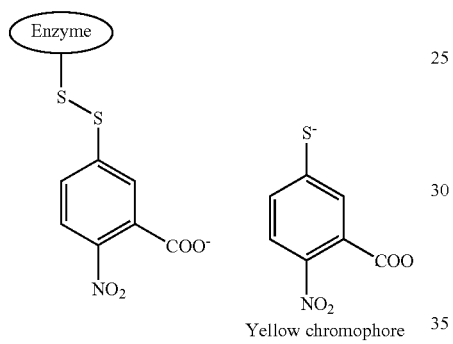

Yellow chromophore each protein solution was removed for testing with Ellman's reagent. No colour change was observed, and so sodium hydroxide was added to the mixture to ensure all free thiols would be deprotonated, still no colour change was observed. Research in the group had shown that by using a solution of Ellman's reagent in ethanol rather than water bad made visualisation easier, however, use of this solution resulted in protein precipitation. Attempts were made to measure absorbance at 412 nm (Fierobe, H.-P., Mirgorodskaya, E., McGuire, K. A., Roepstorff, P., Svensson, B., and Clarke, A. J., *Biochemistry*, 37, 3743-3752 (1998)), but the results showed negligible differences between the blank and protein solutions. It was concluded that the protein thiol concentration used in the modification experiment was too low to enable Ellman's reagent to give a conclusive result.

Given these results it was decided to proceed with the ligation reactions without a monitoring method. The reactions were allowed to run for ~3 h. Purification by dialysis and subsequent concentration of solution afforded the CMM in a 59% and 57% yield of recovered protein for the ligation at pH 7.68 and 8.86 respectively. Mass spectrometry showed complete conversion to one product and no remaining starting material in both cases.

Subsequent reactions to produce two other chemically modified mutants were conducted at pH 7.68 (Scheme 6).

Scheme 6: Chemical modification

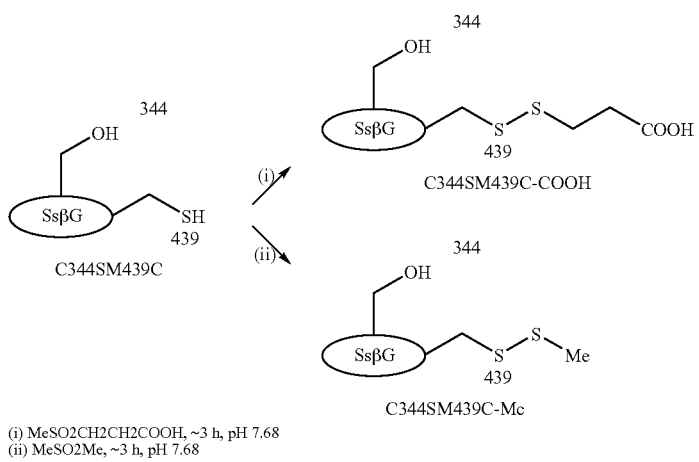

(i) MeSO2CH2CH2COOH, ~3 h, pH 7.68
(ii) MeSO2Me, ~3 h, pH 7.68

Hence initial testing of an aliquot of colourless reaction mixture with Ellman's reagent should form a yellow solution. As the ligation reaction proceeds subsequent testing should result in the formation of a progressively less yellow solution until finally the aliquot of reaction mixture remains colourless on addition of Ellman's when all the free thiols have reacted with the MTS reagent. Attempts were made to follow the reaction by this method. Prior to the reaction an aliquot of After 2½ h the excess MTS reagent was removed by centrifugation in Vivaspin concentrators with 10,000 MWCO, as an alternative to dialysis. This purification method afforded the CMMs in higher yields than those achieved for C344SM439C-NMe$_3^+$. A higher yield of 89% was achieved for C344SM439C-Me and the yield of C344SM439C—COOH was quantitative. Mass spectrometry showed complete conversion to product in both cases. However, initial mass spectra showed high phosphoric acid contamination, which was not removed by drop dialysis. It was believed that phosphoric acid may have been trapped in an enzyme cavity during centrifugation, as unlike dialysis this method of MTS removal does not allow full equilibration between the buffer within the enzyme cavities and the bulk solution. To address this the protein samples were diluted in more buffer and allowed to equilibrate at RT before being prepared for mass spectrometry.

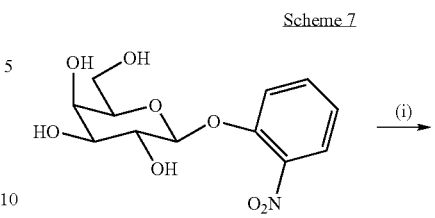

Scheme 7

2.1.2.3 Interpretation of Mass Spectra

All the mass spectra showed the correct mass shift from the reference C344SM439C, to the appropriate CMM (Table 2).

TABLE 2

Mass spectrometry data

| Enzyme | Group introduced | Mass of group | Predicted mass of CMM (based on C344SM439C = 57450) | Found |
|---|---|---|---|---|
| C344SM439C—NMe$_3^+$ | —SCH$_2$CH$_2$NMe$_3^+$ | 119 | 57568 | 57568 |
| C344SM439C—COOH | —SCH$_2$CH$_2$COOH | 105 | 57554 | 57554 |
| C344SM439C—Me | —SMe | 47 | 57496 | 57496 |

It should be noted that the reference mass value of C344SM439C=57450 does not agree with the literature database value of C344SM439C=57504. This may be rationalized in two parts. Firstly, N-terminal sequencing of WT SsβG and a mutant within our group has shown that N-terminal methionine residue cleavage occurs during expression resulting in a mass loss of 131 Da, equal to the cleaved residue. Secondly, the use of phosphate buffer creates phosphate adducts in mass spectrometry (Chowdhury, S. K., Katta, V., Beavis, R. C. and Chait, B. T., *J. Am. Soc. Mass. Spectrom.* 1, 382-388 (1990)). The SsβG protein sample was suspended in phosphate buffer prior to preparation for mass spectrometry. The enzymes were detected as phosphate adducts (phosphate, PO$_3^{2-}$ 79 Da). These two modifications account well for the observed +77 Da mass difference (at ~57500 Da±2 Da is an acceptable margin of error, the mass spectra were refined to 2 Da resolution).

TABLE 3

Mass spectrometry data

| Enzyme | Lit. mass | Lit. mass – Met + PO$_3^{2-}$ | Found | Difference |
|---|---|---|---|---|
| C344SM439C | 57504 | 57452 | 57450 | 2 Da |
| C344SM439C—NMe$_3^+$ | 57622 | 57570 | 57568 | 2 Da |
| C344SM439C—COOH | 57608 | 57556 | 57554 | 2 Da |
| C344SM439C—Me | 57550 | 57498 | 57496 | 2 Da |

2.2 Synthesis of Target Substrates

2.2.1 Synthesis of o-nitrophenyl β-D-galactopyraxnoside-6-phosphate

Treatment of o-nitrophenyl β-D-galactopyranoside with trimethyl phosphate and phosphorous oxychloride as a route to o-nitrophenyl β-D-galactopyranoside-6-phosphate (Scheme 7) has been described by Hengstenberg, W. and Morse, M. L., *Carbohydrate Res.* 10, 463-465 (1969).

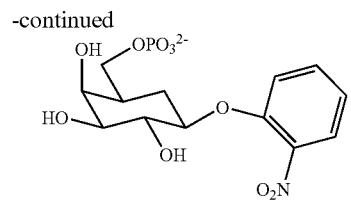

-continued (i) trimethyl phosphate, phosphorous oxychloride, water, 0° C., 3 h, 62%

Neutralization of phosphoric and hydrochloric acids with ammonia solution resulted in the reaction mixture containing inorganic salts in addition to the product, starting material, β-D-galactopyranose and o-nitrophenol resulting from starting material decomposition. The o-nitrophenol was removed by co-evaporation with water until the aqueous solution was colourless. To remove the inorganic salts the residue was then absorbed onto acidified charcoal:celite column and eluted with water. The removal of these salts was monitored by reaction of the eluant with silver nitrate solution (the clear solution becomes turbid in the presence of chloride ions), the assumption being made that chloride and phosphate salts would elute at approximately the same rate. Upon complete removal of these inorganic salts o-nitrophenyl β-D-galacto-pyranoside-6-phosphate, o-nitrophenyl β-D-galactopyra-nosideand β-D-galactopyranose were removed from the column by elution with pyridine solution. The product was isolated as the cyclohexylammoniwn salt in a yield of 62%.

2.2.2 Synthesis of p-nitrophenyl 6-amino-6-deoxy-β-D-galactopyranoside

2.2.2.1 Retrosynthetic Analysis

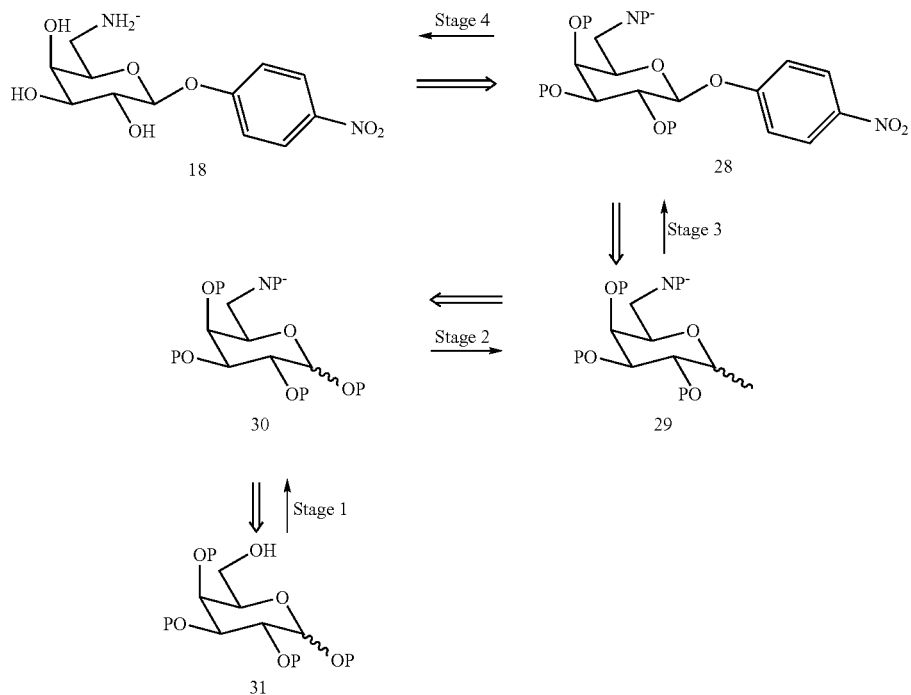

Scheme 8: Retrosynthetic analysis of p-nitrophenyl 6-amino-6-deoxy-b-D-galactopyranoside The synthesis of the target molecule 18 can be separated into four distinct stages. The first stage is to replace the C-6 hydroxyl with a protected nitrogen group (NP') which may be deprotected in later steps to give access to the amine. In order to introduce this regioselectively it is necessary that all other hydroxyl groups are protected (P).

The second stage in the synthesis is to introduce a suitable leaving group (L) at the anomeric position, to then enable stereocontrolled introduction (stage 3) of the chromophore to the anomeric position to give the β-product. In this case, the chromophore selected is p-nitrophenol. Once access to 28 is achieved, the fourth remaining stage is to deprotect both the hydroxyl groups and the nitrogen to yield the target molecule 18.

The nitrogen protecting group selected is an azide and the tetra-protected sugar starting material chosen for this initial step is 1,2:3,4-diisopropylidene-α-D-galactopyranose. This is because it is readily available, and direct access to 6-azido-6-deoxy-1,2,3,4-diisopropylidene-α-D-galactopyranose can be achieved by use of a modified Mitsunobu reaction.

The resulting sugar can then be de-protected with acid and subsequently re-protected with acetyl protecting groups. The strategy behind this change in protection groups is that the presence of acetyl groups will allow neighbouring group participation to be utilized in future steps to control the anomeric stereochemistry upon chromophore addition. Access to 28 may be achieved via an α-bromide or other leaving group L. The atom introduced at the anomeric position of the tetra-acetyl protected sugar may serve as a leaving group in the following step to introduce the chromophoric group. Activation followed by attack by p-nitrophenol should yield exclusively p-nitrophenyl 2,3,4-tri-O-acetyl-6-azido-6-deoxy-β-D-galactopyranoside. This can then be deprotected by base. The remaining azide deprotection step may normally be achieved by either catalytic hydrogenation or a Staudinger reaction. However, in this particular case catalytic hydrogenation is a less viable option owing to the presence of the aromatic ring and nitro group which might also be hydrogenated, hence deprotection of the azide via a Staudinger reaction will yield the target molecule 18.

2.2.2.2 Preparation of 6-azido-6-deoxy-diisopropylidene-α-D-galactopyranose Research conducted by Moris-Varas, F., Qian, X.-H., and Wong, C.-H., *J Am. Chem. Soc.* 118, 7647-7652 (1996) described the use of a modified Mitsunobu reaction as a means of replacing the 6-position hydroxyl group on a protected sugar with an azide group (Scheme 9).

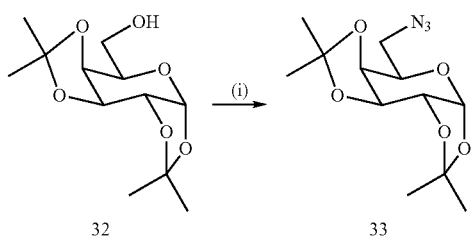

Scheme 9

(i) triphenyl phosphine, disopropylazodicarboxylate, hydrazoic acid, toluene, 97%

Initial attempts at this reaction gave poor yields in the region of 30%, despite t.l.c after 2 h indicating the reaction had seemingly run to completion with formation of one product. However, after basic work up three compounds were visible by t.l.c. Purification by flash column chromatography allowed these to be separated and were shown to be the desired product, starting material and diisopropylazodicarboxylate. In subsequent reactions, a micro-work up was performed on an aliquot of the reaction mixture prior to t.l.c. Consequently, the reaction was shown not to have run to completion after 2 h, and accordingly the reaction time was increased with the yield being optimised at 97% after 67 h.

2.2.2.3 Alternative Route to 6-azido-6-deoxy-diisopropylidexe α-D-galactopyranose Whilst the outcome of the above reaction was investigated an alternative route to 6-azido-6-deoxy-diisopropylidene-D-galactopyranose was also evaluated (Scheme 10) (Han, J. W. and Hayashi, T., *Chem. Lett.* 10, 976-977 (2001)).

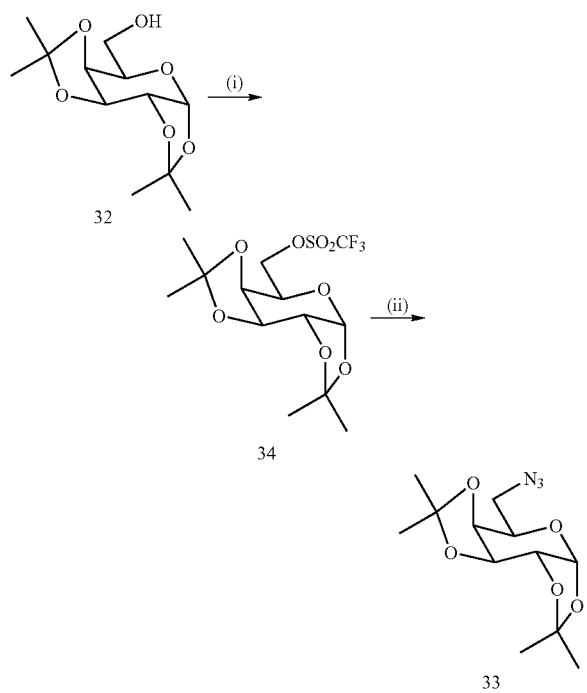

(i) trifluoromethane sulfonic anhydride, pyridine, DCM, 2 h, 42%
(ii) sodium azide, DMF, 23 h, 80%

1,2:3,4-diisopropylidene-α-D-galactopyranose was treated with triflic anhydride and pyridine in DCM to form the primary triflate. Subsequent displacement with sodium azide afforded 6-azido-6-deoxy-diisopropylidene-α-D-galactopyranose in a yield of 32% over 2 steps. Although work on this strategy was discontinued after a 97% yield was achieved via the modified Mitsunobu route, it is possible that this two-step yield can be increased if unstable 1,2:3,4-diisopropylidene-trifluoromethanesulfonate-α-D-galactopyranose is carried forward without purification and reacted immediately with sodium azide.

2.2.2.4 Preparation of 6-azido-6-deoxy-1,2,3,4-tetra-O-acetyl-D-galactopyranose

With 6-azido-6-deoxy-diisopropylidene-D-galactopyranose in hand, exchange of the isopropylidene protecting groups for acetyl protecting groups could take place. The isopropylidene groups were removed by aqueous acetic acid at 70° C. (Scheme 11) (Moris-Varas, F., Qian, X.-H., and Wong, C.-H., *J. Am. Chem. Soc.* 118, 7647-7652 (1996)).

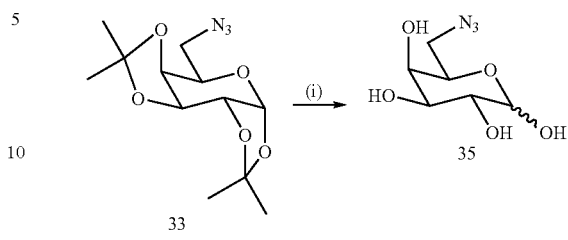

(i) acetic acid (aqueous, 80%), 70° C., 69 h, 63%

The deprotection reaction proceeded smoothly, and in the subsequent reprotection step two methods of acetylation were compared (Scheme 10, Table 4) (Kartha, K. P. R., and Field, R., A., *Tetrahedron*, 53, 11753-11766 (1997)).

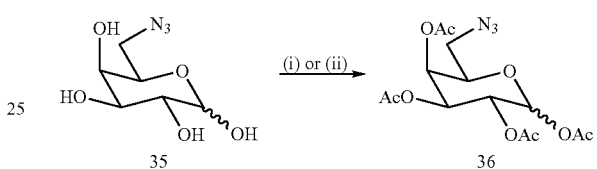

TABLE 4

| Comparison of acetylation methods | | | |
|---|---|---|---|
| Method | Reagents | Reaction time | Yield |
| (i) | acetic anhydride, iodine | 5½ h | 49% |
| (ii) | acetic anhydride, pyridine, 4-(dimethylamino)pyridine | 75 h | 80% |

It was decided to use method (ii) as it gave a higher yield. When the de-protection and re-protection steps were conducted consecutively without purification of 35 the yield over two steps was optimised at 90%.

2.2.2.5 Attachment of p-nitrophenol at the anomeric centre 2.2.2.5.1 Via 2,3,4-tri-O-acetyl-6-azido-6-deoxy-α-D-galactopyranosyl bromide The acetate 30 was treated with hydrogen bromide in acetic acid to afford 29 which was used without further purification (Scheme 13) (Mitchell, M. B., and Whitcomb, W. A. I., *Tetrahedron Lett.* 41, 8829-8834 (2000)).

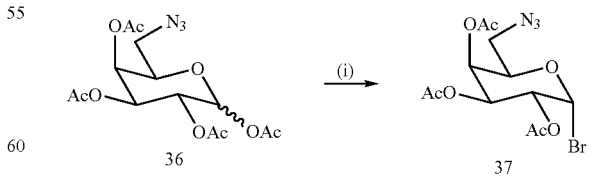

(i) hydrogen bromide (30% in acetic acid), DCM, 0° C.

The bromide 37 was treated with silver triflate and p-nitrophenol in the presence of base (Ottoson, H., *Carbohydrate Res*, 197, 101-107 (1990)) (Scheme 14). However, none of the expected product 38 was formed, instead acetate migration occurred to give 39. Surprisingly, characterization of 39 by m/z was not possible.

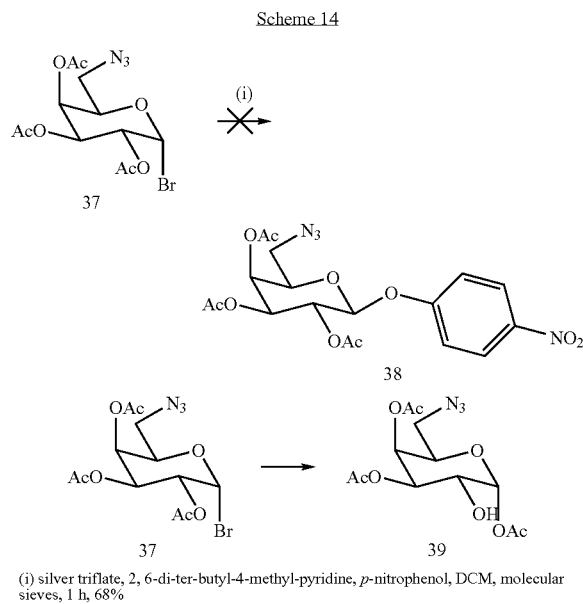

Scheme 14

(i) silver triflate, 2, 6-di-ter-butyl-4-methyl-pyridine, *p*-nitrophenol, DCM, molecular sieves, 1 h, 68%

However other characterization was considered conclusive evidence even in the absence of supportive m/z spectra; nmr spectra indicated three acetyl groups, showed an anomeric proton nmr peak at δ 6.37 ppm, typical of the presence of a deshielded acetyl group at the anomeric position and also indicated $J_{1,2}$=3.2 Hz which is characteristic of the α-anomer. IR showed absorptions characteristic of C=O and O—H bonds.

2.2.2.5.2 Via Direct Displacement of Acetate with p-Nitrophenol

After the above method of formation of 38 via the bromide 37 proved to be unsuccessful, attempts were made to attach p-nitrophenol using the tetraacetate 36 as a glycosyl donor and Lewis acid catalysis in DCM Nishida, Y., Takamori, Y., Matsuda, K., Ohrui, H., Yamada, T., Kobayashi, K., *J. Carb. Chem.* 18, 985-997 (1999)) to form the desired β-anomer (Scheme 15). This reaction unexpectedly gave the α-anomer 40 rather than the β-anomer 38.

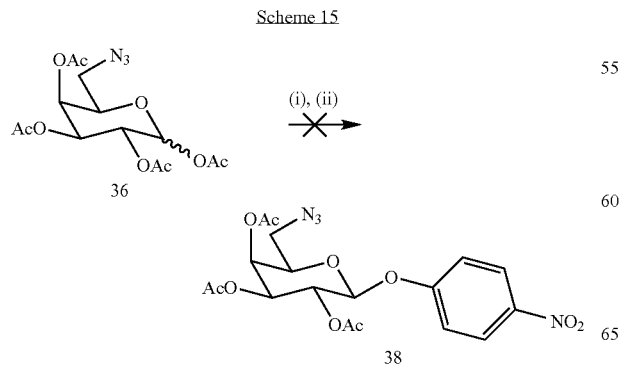

Scheme 15

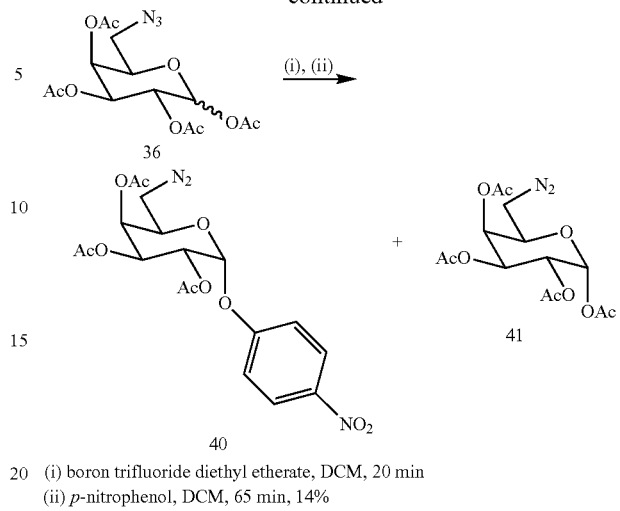

(i) boron trifluoride diethyl etherate, DCM, 20 min
(ii) *p*-nitrophenol, DCM, 65 min, 14%

Scheme 15 shows the most successful reaction conditions. In initial reactions, all the reactants were mixed together from the start. Under these conditions some product 40 was formed but isolation of a pure sample was not achieved. Reaction conditions were varied in order to optimise yield (Scheme 16 below, Table 5).

Scheme 16: Reaction to be optimized

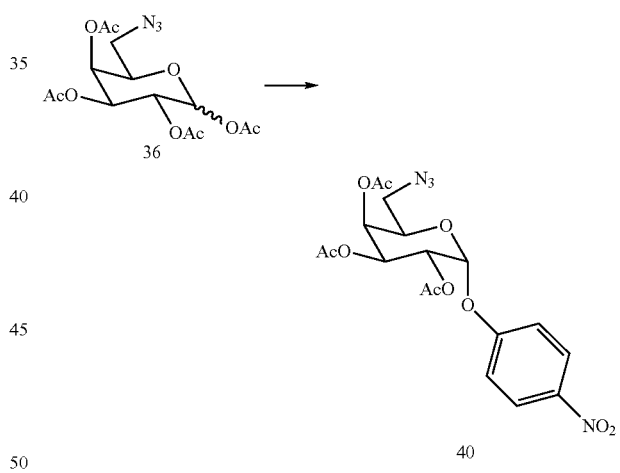

TABLE 5

Reaction conditions for glycosidic bond formation

| Number of eq of BF₃•Et₂O used | Addition method | Reaction temp | Reaction time | Product 40 yield |
|---|---|---|---|---|
| 1 | All reactants together | 0° C. | 1 h | 8% |
| 1 | Premix 36 and BF₃•Et₂O | RT | 1 h 40 min | 10% |
| 1 | All reactants together | RT | 2 h | Some product formation, but heavy pNP contamination |

TABLE 5-continued

Reaction conditions for glycosidic bond formation

| Number of eq of $BF_3 \cdot Et_2O$ used | Addition method | Reaction temp | Reaction time | Product 40 yield |
|---|---|---|---|---|
| 1 | All reactants together | RT | 3 h | none |
| 5 | All reactants together | RT | 50 h | none |
| 5 | Premix 36 and $BF_3 \cdot Et_2O$ | RT | 65 min | 14% |

Monitoring this reaction proved problematic, as the starting material 36 and p-nitrophenol co-ran to some extent in all tested t.l.c. solvent systems p-Nitrophenol has a very similar $R_f$ value to that of the product in addition to that of the starting material, therefore purification by flash column chromatography alone was insufficient, and it was necessary to co-evaporate water from the crude product to reduce the amount of p-nitrophenol present in the mixture and ease the subsequent purification step. Yields of product were low and a large proportion of material recovered after purification was identified as the α-anomer of the starting material, 6-azido-6-deoxy-1,2,3,4-tetra-O-acetyl-α-D-galactopyranose 41. After extended reaction times (>2 h) product 40 was not isolated, however, the column fractions with low $R_f$ values did show characteristic azide absorptions in IR and peaks typical of a galactose derivative in mm spectra. It is suggested that after extended reaction times the Lewis acid may remove the acetyl protecting groups (Askin, D., Angst, C., Danishefsky, S., *J. Org. Chem.* 52, 622-635 (1987)).

It was discovered that for the product 40 $^3J_{1,2}=3.7$ Hz, which in the case of galactose is characteristic of the α-anomer. In order to be certain that the α-anomer 40 had been formed, the coupling constant $^1J_{C-1,H-1}$ was measured. Bock and Pedersen Bock, K and Pedersen, C., *J. Chem. Soc, Perkin Trans.s* 2, 293-297 (1974) have described how $^1J_{C-1,H-1}$ coupling constants of α-glycosides are found to be ~170 Hz, and for β-glycosides ~160 Hz. $^1J_{C-1,H-1}=175$ Hz for the product 40, thus proving the α-anomer had been formed. It was originally expected that this reaction (scheme 13) would form the β-anomer due to neighbouring group participation by the C-2 acetate, and indeed this was the reason for the choice of acetyl protecting groups. The postulated mechanism for the formation of the α-anomer is that an equilibrium is set up (Scheme17); initially the β-anomer is formed due to neighbouring group participation. The Lewis acid then co-ordinates to the phenyl oxygen atom and removes the p-nitrophenyl group with assistance from the ring oxygen lone pair. The p-nitrophenyl then re-attaches to the ring in the α-relative configuration, to form the thermodynamically more stable α-anomer due to the anomeric effect.

Scheme 17: Postulated mechanism for Scheme 16

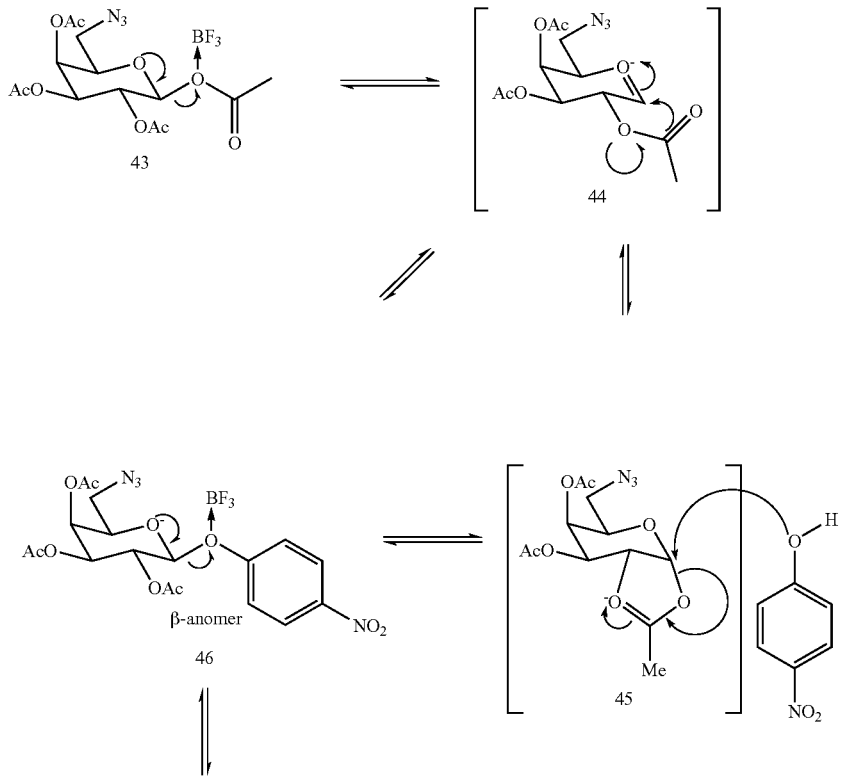

-continued

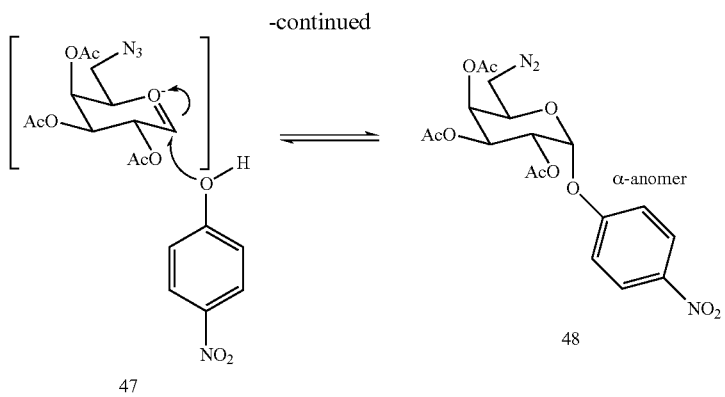

At this point work on this reaction was discontinued as SsβG is β-anomer specific and will not process α-anomers. Unfortunately, time constraints did not allow further investigation into the synthesis of the target molecule 18.

2.3 Investigation of Kinetic Parameters

The kinetic activity of SsδG was assessed using ultraviolet/visible spectroscopy. Cleavage of the glycosidic bond of the nitrophenyl sugar analogue releases a chromophore (Scheme 18), either p-nitrophenol or o-nitrophenol.

Scheme 18: Action of SsbG

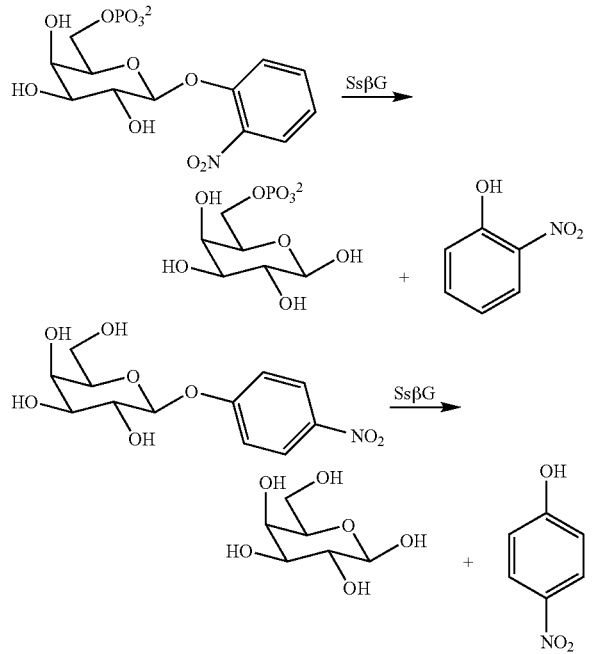

The absorbance of these chromophores at 405 nm was continuously measured at regular time intervals, and the Beer-Lambert Law used to calculate the chromophore concentration at each of these time intervals.

Abs=∈cl

In order to use this equation the extinction coefficient, ∈, of both p-nitrophenol and o-nitrophenol were calculated. Enzyme kinetic parameters were assessed using the initial rates method. The gradient of a plot of chromophore concentration against time gave the initial rate of reaction at a series of substrate concentrations (0.05-10 mM). Kinetic parameters were calculated by regression analysis of the kinetic data on the Michaelis-Menten Model (Fersht, A., *Enzyme Structure and Mechanism*, W.H. Freeman and Company, New York (1985)). The initial rate of reaction was measured. This model is valid when [substrate]>>[enzyme], which are initial rate conditions.

$K_M$ and $v_{max}$ were calculated from non-linear Michaelis-Menten and linear Lineweaver-Burk plots. From these values, $k_{cat}$ and $k_{cat}/K_M$ were calculated and compared.

$K_M=v_{max}/2$, it is the concentration of substrate at which half the active sites are filled. Higher $K_M$ values correspond to weaker binding and lower $K_M$ values correspond to stronger binding $k_{cat}$, the turnover number is the number of substrate molecules which are converted to product when the enzyme is saturated with substrate and v (rate) is maximised. Given both of these considerations, binding and rate, $k_{cat}/K_M$ is typically as a measure of the overall relative activity of the enzyme. To allow comparison of the activity of the enzymes, $\ln(\{k_{cat}/K_M\}\text{mutant}/\{k_{cat}/K_M\}\text{WT})$ was calculated for each enzyme-substrate combination, to give overall activity relative to WT.

2.3.1 Kinetic Investigations with p-nitrophenyl β-D-galactopyranoside (pNPGal)

FIG. 2 shows the average value of $\ln(\{k_{cat}/K_M\}\text{mutant}/\{k_{cat}/K_M\}\text{WT})$ over the three runs performed. Positive values indicate higher overall activity relative to WT enzyme, negative values indicate lower overall activity relative to WT.

TABLE 6

Structure of enzyme side chains at position 439

| Enzyme | Side chain structure |
| --- | --- |
| WT | —CH$_2$CH$_2$SCH$_3$ |
| C344S | —CH$_2$CH$_2$SCH$_3$ |
| C344SM439C | —SH |
| C344SM439C—NMe$_3^+$ | —SSCH$_2$CH$_2$NMe$_3^+$ |
| C344SM439C—COOH | —SSCH$_2$CH$_2$COOH |
| C344SM439C—Me | —SSCH$_3$ |

The two point mutant, C344SM439C, showed highest overall activity of the enzymes screened with pNPGal, even greater than the WT enzyme; $\ln(\{k_{cat}/K_M\}\text{mutant}/(\{k_{cat}/K_M\}\text{W})$ is positive. It shows both stronger binding, average $K_M=376$ μM vs $K_M=459$ μM for WT and a higher average $k_{cat}$, 18890 s$^{-1}$ compared to 11140 s$^{-1}$ for WT (Table 7).

TABLE 7

Kinetic parameters (averaged over 3 runs, except * averaged over 2 runs)

| Enzyme | $K_M$/mM | Standard deviation | $k_{cat}/s^{-1}$ | Standard deviation | $(k_{cat}/K_M)/$ $M^{-1}s^{-1}$ | Standard deviation |
|---|---|---|---|---|---|---|
| WT | 0.459 | $3.92 \times 10^{-2}$ | 5.07 | 0.48 | 11140 | 1780 |
| C344S | 0.475 | $2.52 \times 10^{-2}$ | 4.16 | 0.17 | 8787 | 750 |
| C344SM439C | 0.376 | $1.23 \times 10^{-2}$ | 7.09 | 0.16 | 18890 | 1060 |
| C344SM439C-NMe$_3^+$ | 0.464 | $7.70 \times 10^{-2}$ | 3.48 | 0.22 | 7563 | 706 |
| C344SM439C-COOH* | 0.334 | $2.12 \times 10^{-2}$ | 2.26 | 0.15 | 6826 | 786 |
| C344SM439C-Me | 0.272 | $1.06 \times 10^{-2}$ | 2.29 | 0.07 | 8446 | 86 |

This is further supported by other data generated in the group in which the single point mutant M439C shows higher activity than WT (thanks to Susan Hancock for supplying this data. It is postulated that this is because of the relative steric environments of the active sites. The side chain at position 439 in WT is longer than the side chain in C344SM439C and M439C (Table 6, page 34), the difference of a methionine compared to a cysteine residue, and so there is more space in the active site and less steric hinderance to the incoming substrate.

C344S and the CMMs all show lower overall activity with pNPGal compared to WT. Position 344 is not in or near the active site, however, as the C344S mutant shows lower activity than WT, it may be that the mutation causes some alteration in protein structure which in turn alters the structure of the active site and reduces activity. C344SM439C-Me has the highest overall activity of the CMMs, and also has the shortest side chain, causing less steric hinderance to the incoming substrate. C344SM439C-Me and C344SM439C—COOH exhibit lower $K_M$ values than the WT corresponding to stronger binding, but due to their lower $k_{cat}$ values this results in lower overall activity. C344SM439C-NMe$_3^+$ exhibits weaker bonding with pNPGal than the other CMMs, but its higher $k_{cat}$ value leads to similar overall activity.

Figure 3:
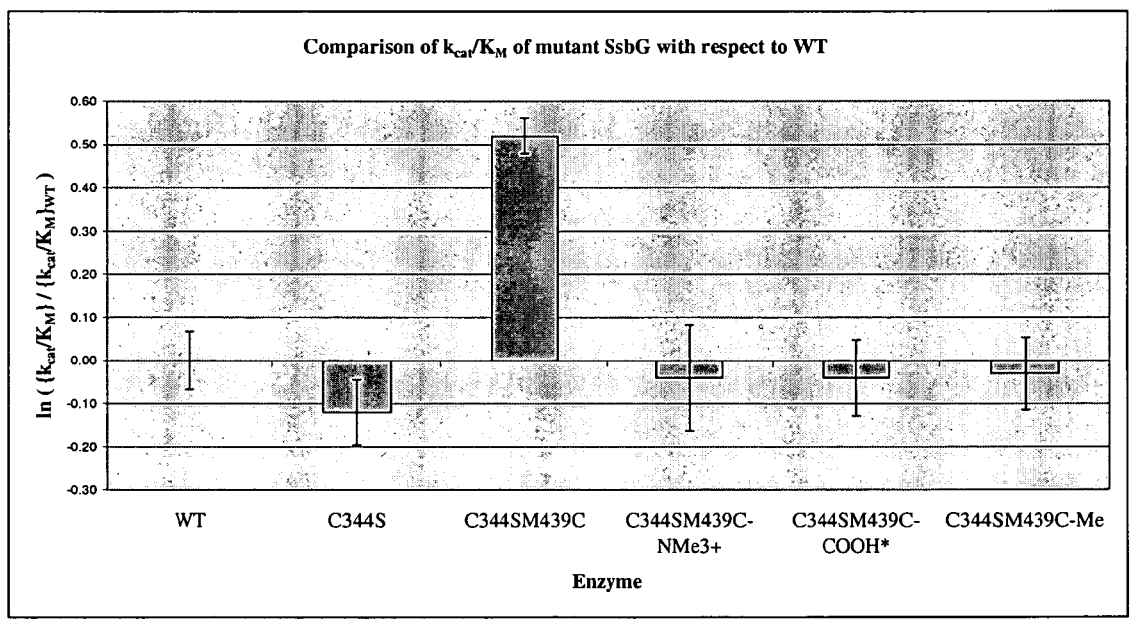
FIG. 3: Overall activity of chemically modified mutant enzymes (CMMs) with oNPGalP6 relative to wild-type (WT) (average over 3 runs, except * average over 2 runs) with standard deviation error bars.

2.3.2 Kinetic Investigations with o-nitrophenyl β-D-galactopyranoside-6-phosphate Having established the kinetic parameters of the six enzymes with pNPGal, the same parameters were calculated for the oNPGalP6 substrate. The results were similar in that C344SM439C showed the highest overall activity (FIG. 3) (for side chain groups see Table 6), and the CMMs on average show slightly lower overall activity compared to WT.

The $K_M$ value (Table 8) for C344SM439C may be explained sterically and electrostatically. The thiol side chain of the cysteine residue in the active site is the smallest of all the enzymes tested, which allows it to best accommodate the bulky phosphate group on the C-6 hydroxyl. Also, hydrogen bonding interactions between the thiol hydrogen and phosphate oxygens may contribute towards increased binding strength.

TABLE 8

Kinetic parameters (averaged over 3 runs, except * averaged over 2 runs)

| Enzyme | $K_M$/mM | Standard deviation | $k_{cat}/s^{-1}$ | Standard deviation | $(k_{cat}/K_M)/$ $M^{-1}s^{-1}$ | Standard deviation |
|---|---|---|---|---|---|---|
| WT | 2.09 | 0.32 | 5.52 | 0.78 | 2652 | 183 |
| C344S | 3.59 | 0.29 | 8.42 | 0.21 | 2357 | 177 |
| C344SM439C | 2.04 | 0.08 | 9.11 | 0.43 | 4473 | 188 |
| C344SM439C-NMe$_3^+$ | 2.45 | 0.32 | 6.21 | 0.49 | 2556 | 319 |
| C344SM439C-COOH* | 3.72 | 0.35 | 9.40 | 0.05 | 2541 | 225 |
| C344SM439C-Me | 4.30 | 0.30 | 11.07 | 0.19 | 2583 | 221 |

All of the CMMs have higher $k_{cat}$ values than WT, but also higher $K_M$ values, corresponding to weaker enzyme-substrate binding. However, there is a notable difference between C344SM439C—COOH and C344SM439C-NMe$_3^+$. The $K_M$ value of C344SM439C—COOH is higher than that of C344SM439C-NMe$_3^+$ indicating weaker binding. It is possible that this is due to electrostatic repulsion between the carboxylic acid group and the phosphate group, whereas the bonding interaction between the negatively charged phosphate group and positively charged trimethyl ammonium group is favourable due to their complementary charges.

2.3.3 Comparison of the Two Data Sets

The $K_M$ values for all the enzymes with the phosphorylated substrate are an order of magnitude higher than with the pNPGal. There are two postulated reasons for the lower binding strength between oNPGalP6 and the enzymes compared to pNPGal. Firstly, the phosphate group on the C-6 hydroxyl is larger than the hydroxyl group present in pNPGal, and so it is probable that the phosphorylated substrate may encounter greater steric repulsion on entering the active site. The second possibility is that it is due to the relative positioning of the aromatic substituent. The nitro group on the aromatic ring is ortho in the case of the phosphorylated substrate, and para in the case of the non-phosphorylated sugar. It may be that the shape of the active site accommodates the para group better than the ortho group, and hence the former binds more strongly.

For each of the enzymes screened, values of $k_{cat}$ are greater with the phosphorylated substrate than with pNPGal, but the higher $K_M$ for oNPGalP6-enzyme binding leads to lower overall activity.

2.3.4 Side-Chains in the Active Site

TABLE 9

Length of side chains at position 439

| Enzyme | Side-chain | Length of side chain/Å |
|---|---|---|
| WT | —$CH_2CH_2SCH_3$ | 7.28 |
| C344S | —$CH_2CH_2SCH_3$ | 7.28 |
| C344SM439C | —SH | 3.08 |
| C344SM439C—$NMe_3+$ | —$SSCH_2CH_2NMe_3^+$ | 11.34 |
| C344SM439C—COOH | —$SSCH_2CH_2COOH$ | 10.96 |
| C344SM439C—Me | —$SSCH_3$ | 6.78 |

Across the six enzymes there are five different side chains present at position 439. Modelling with ChemDraw 3D Pro™ was conducted to elucidate a rough guide to the relative length of these side chains. Each side chain (from the α-carbon) was entered into the programme, its lowest energy configuration obtained by running of MOPAC optimisation and then its bond lengths measured. Obviously, the lowest energy conformation is for the chain 'free in space', not constrained within the environment of a protein active site, in which additional stabilisation/destabilisation forces may affect the exact conformation of the chain. However, treated with appropriate caution, it is believed that this data serves as a rough guide to enable conclusions to be drawn about the effect of the steric bulk of the side chain in the active site.

2.3.5 Summary of Kinetics Results

All the enzymes screened have shown greater overall activity with pNPGal than with oNPGalP6, and WT shows the second highest activity with both pNPGal and oNPGalP6, surpassed only by C344SM439C. The main factor affecting enzyme activity would appear to be the steric environment of the active site, although the phosphorylated substrate did show a slightly stronger binding affinity with the enzyme possessing a complementary positive charge in the active site.

These results are interesting as it appears that the steric environment of the active site has a greater effect on enzyme activity than the electrostatic environment. At the beginning of this project it was postulated that the charged substrates would show highest activity with enzymes possessing a complementary charge in their active site, increasing binding strength and lowering $K_M$, and that this would be the major factor affecting enzyme activity. It was also expected that WT would show highest overall activity with pNPGal. However, C344SM439C, possessing no charge in the active site and the shortest side chain at position 439 (~3 Å), showed the highest activity of all the enzymes with both substrates.

If the steric environment of the active site does not allow the incoming substrate to come within a close enough proximity of any charged groups with which it could have a stabilizing electrostatic interaction, or if any electrostatic interaction causes the positioning of the substrate in the active site to be different to that preferred for optimal performance by the enzyme, then it is possible that no benefit will arise from the modification.

Despite this, these results are encouraging, especially those achieved for the pNPGal substrate, as they demonstrate that the enzyme activity can be tailored (in this specific case, lowered) by the combined strategy of site-directed mutagenesis and chemical modification. Comparison of $K_M$ values for C344SM439C—COOH and C344SM439C-$NMe_3^+$ with oNPGalP6 did show stronger binding between the latter and the substrate, indicating that the substrate specificity had been tailored by chemical modification. Further investigations using pNPGalP6, and MTS reagents with a shorter chain length may yield more definitive results about the interplay of steric and electrostatic factors in affecting the activity of this enzyme, and hence provide an indication of how best to tailor the substrate specificity.

2.4 Conclusions

The two target MTS reagents (15, 16) were synthesised and used in addition to methyl methanethiolsulfonate to chemically modify C344SM439C. These modifications were confirmed by mass spectrometry. Synthesis of the phosphorylated substrate 17 was successful, and this was used in addition to p-nitrophenyl β-D-galactopyranoside 19, to investigate the kinetic activity of SsβG. These kinetic investigations showed that the activity of SsβG can be tailored by the combined approach of site-directed mutagenesis and chemical modification. However, it appears that the steric environment of the active site has a greater effect on enzyme activity and specificity than the electrostatic environment. Complete synthesis of 18 was not achieved, but access was gained to 36 and 37, which may provide the basis of future work to complete the synthesis. Further kinetic investigations with other MTS reagents and substrates may yield more definitive results about the interplay of steric and electrostatic factors involved in modifying the activity of SsβG.

3. Experimental

3.1 General Experimental

3.1.1 General Synthetic Chemistry Experimental

Melting points were recorded on a Kofler hot block and are uncorrected. Proton nuclear magnetic resonance (1H) spectra were recorded on Bruker AC 200 (200 MHz), Bruker DPX 400 (400 MHz), Bruker DQX 400 (400 MHz) or by Dr. B. Odell on Bruker AMX 500 (500 MHz) spectrometers. Carbon nuclear magnetic resonance $^{13}C$) spectra were recorded on a Bruker DQX 400 (100.6 MHz) or by Dr. B. Odell on Bruker AMX 500 (125.7 MHz) spectrometers. Proton spectra were assigned using COSY. Carbon-13 spectra were assigned using HMQC. Multiplicities were assigned using DEPT or APT sequence. All chemical shifts are quoted on the δ-scale in parts per million (ppm) and are referenced to residual solvent frequencies. Infrared spectra were recorded on a Perkin-Elmer 150 Fourier Transform spectrophotometer. Mass spectra were recorded on a Micromass Platform 1 spectrometer, or by Dr. N. Oldham or Mr. R. Proctor on a Walters 2790-Micromass LCT electrospray ionisation mass spectrometer or Micromass AutoSpec-oaTof spectrometer and are reported in Daltons and followed by their percentage abundance in parentheses. Optical rotations were measured on a Perkin-Elmer 241 polarimeter with a path length of 1 dm. Concentrations are given in g/100 ml. Thin layer chromatography (t.l.c.) was performed on Merck aluminium backed plates precoated with silica (0.2 mm, 60 $F_{254}$) or Merck Kieselgel glass-backed sheets pre-coated with silica (0.22-0.25 mm, 60 $F_{254}$). Plates were visualised using i) ultraviolet lamp ($\lambda_{max}$=254 nm), ii) ninhydrin (0.2% in methanol), iii) phosphomolybdic acid (10% in ethanol), iv) methanol:water: sulphuric acid (conc) 45:45:3. Flash column chromatography was carried out on silica gel (Fluka Kieselgel 60 220-440 mesh) (Still, W. C., Kahn, M., and Mitra, A., *J. Org. Chem.* 43, 2923-2925 (1978)). Solvents and reagents were dried and purified before use; dichloromethane was distilled from calcium hydride, all other anhydrous solvents were purchased directly from manufacturer. 'Petrol' refers to the fraction of light petroleum ether boiling in the range 40-60° C.

3.1.2 General Biological Experimental

Sodium phosphate buffer solutions (50 mM) were prepared according to the method described by Gomori using the Henderson-Hasselbalch equation (Sambrook, J., and Russell, D. W., *Molecular Cloning a Laboratory Manual Volume 3*, Cold Spring Harbor Laboratory Press, New York (2001)). Ultra-pure water describes distilled water, de-ionised to 18.2 MΩ resistivity from an Elga Maxima unit coupled to an Elgastat Prima reverse osmosis system. Ammonium acetate buffer describes a 10 mM solution in ultra-pure water pH 6.78. The pH of solutions was measured with a Jenway 3320 pH meter connected to a Gelplas (BDH) electrode. This was calibrated at pH 4.0, 7.0, and 10.0 before use and stored in saturated potassium chloride solution. Centrifugation was performed at room temperature in a MSE Micro Centaur centrifuge at 13,000 r.p.m. Protein mass spectra were recorded on Micromass Platform 2 spectrometer. Absorbance was measured using a Molecular Devices Spectra Max Plus plate reader. Bradford reagent concentrate was purchased from Bio-Rad. Dialysis tubing was purchased from Medicell International Ltd.

3.2 General Biological Procedures

3.2.1 Chemical Modification of C344SM439C

C344 μM439C-NMe$_3^+$

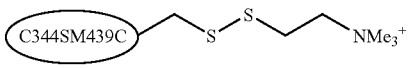

C344SM439C (53.1 mg of a lyophilised purified protein sample) was suspended in phosphate buffer (1 mL, 50 mM, pH 7.68) and agitated on a tube rotator. After 15 min, the solution was filtered (0.2 μm Nalgene syringe filter). The filtrate was analysed for protein concentration using the Bradford test (found 0.94 mgmL$^{-1}$) and a portion of this solution (100 μL) was retained for mass spectrometry analysis. A solution of 2-(trimethylammonium)ethyl methanethiosulfonate bromide 15 (1 mg, 4 μmol) in phosphate buffer (200 μL, 50 mM, pH 7.68) was prepared. A portion of this solution (100 μL) was added to the protein solution, mixed by vortexing (5 s) and then agitated on a tube rotator at room temperature. After 30 min, the remainder of the 2-(trimethylammonium)ethyl methanethiosulfonate bromide solution (100 μL) was added, mixed by vortexing (5 s) and then agitated on a tube rotator. After 105 min, the reaction solution was transferred into dialysis tubing. The reaction mixture was dialysed in phosphate buffer (pH 6.42, 50 mM, 1 L, 2×1 h). The resulting solution (1500 μL) was concentrated in a Vivaspin 0.5 mL concentrator (10,000 MWCO, pre-washed with ultra-pure water (100 μL), and phosphate buffer (100 μL, 50 mM, pH 6.42)) to a volume of 25 μL (concentrator minimum volume). The solution was diluted with phosphate buffer (975 μL, 50 mM, pH 6.24) to afford a solution of C344SM439C-NMe$_3^+$ in phosphate buffer (pH 6.42) (0.55 mgmL$^{-1}$, 59%); m/z (ES+) 57568 (C344SM439C-NMe$_3^+$+covalently bound phosphate, 100%).

C344SM439C-Me and C344SM439C—COOH

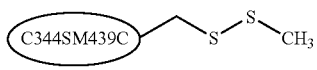

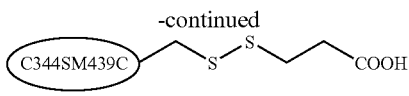

C344SM439C (300 mg of a lyophilised purified protein sample) was resuspended in phosphate buffer (6 mL, 50 mM, pH 7.68) and agitated on a tube rotator. After 15 min, the solution was filtered (0.2 μm Nalgene syringe filter). The resulting solution was analysed for protein concentration using the Bradford test (found 0.80 mgmL$^{-1}$). A solution of MTS reagent (1 mg, 5.4 μM, 2-carboxyethyl methanethiosulfonate 16 or 1 μL, 9.7 μM, methyl methanethiolsulfonate) in phosphate buffer (200 μL, 50 mM, pH 7.68) was prepared. A portion of this solution (100 μL) was added to the protein solution, mixed by vortexing (5 s) and then agitated on a tube rotator at room temperature. After 30 min, the remainder of the MTS solution (100 μL) was added, mixed by vortexing (5 s) and then agitated on a is tube rotator. After 2 h, the reaction mixture was concentrated in a Vivaspin 0.5 mL concentrator (10,000 MWCO, pre-washed with ultra-pure water (100 μL), and phosphate buffer (100 μL, 50 mM, pH 6.49)) to a volume of 25 μL (concentrator minimum volume). The concentrate was washed with phosphate buffer (4×100 μL, 50 mM, pH 6.49) and then diluted with phosphate buffer (975 μL, 50 mM, pH 6.49). An aliquot of this solution (100 μL) was removed and diluted with phosphate buffer (pH 6.5, 50 mM, 1 mL) and agitated on a tube rotator. After 7 h, the solution was concentrated in a Vivaspin 0.5 mL concentrator (10,000 MWCO, pre-washed with ultra-pure water (100 μL), and phosphate buffer (100 μL, 50 mM, pH 6.49)) to a volume of 25 μL (concentrator minimum volume), and then diluted with phosphate buffer (75 μL, 50 μM, pH 6.49) to afford a solution of CMM (100 μL in 50 mM, pH 6.5 phosphate buffer) for mass spectrometry analysis (for preparation see 3.2.2).

C344SM439C—COOH was afforded as a solution in phosphate buffer (50 mM, pH 6.49) (quantitative yield); m/z (ES+) 57554 (C344SM439C—COOH+covalently bound phosphate, 100%). C344SM439C-Me was afforded as a solution in phosphate buffer (pH 6.49) (89%), m/z (ES+) 57496 (C344SM439C-Me+covalently bound phosphate, 100%).

3.2.2 Bradford Test Method

Bovine Serum Albumin (BSA) standards in the range of 0.1-1 mgmL$^{-1}$ were prepared from a 10 mgml$^{-1}$ stock solution. Bradford reagent was prepared by 5-fold dilution of dye concentrate with ultra-pure water and then filtration through filter paper under gravity according to manufacturers protocol. In a 96-well flat bottom microtitre plate, Bradford reagent (200 μL) was added to the sample (4 μL) (either blank, BSA standard or test protein) and manually agitated for 5 min before measurement commenced. Protein samples were diluted to ensure A$_{595}$<1. Measurement of each dilution of the reference protein was conducted in triplicate. Absorbance was measured at 595 nm according to literature protocol (Fierobe, H.-P., Mirgorodskaya, E., McGuire, K. A., Roepstorff, P., Svensson, B., and Clarke, A. J., *Biochemistry*, 37, 3743-3752 (1998)).

3.2.3 Preparation of Protein Samples for Mass Spectrometry

In order to change the buffer, protein solution (100 μL of a ~20 μM solution in phosphate buffer) was concentrated in a Vivaspin 0.5 mL concentrator (10,000 MWCO, pre-washed with ultra-pure water (100 μL), and ammonium acetate (100 μL) to a volume of 25 μL (concentrator minimum volume). The concentrate was washed with ammonium acetate (4×100 μL) and then diluted with ammonium acetate (75 μL). Mass spectrometry was conducted on this solution. In instances where phosphoric acid contamination was evident, the sample was purified further by drop dialysis; protein solution (10 μL of a 20 μM solution in ammonium acetate as prepared above) was mixed with an acidic solution (water, 5% methanol, 3% formic acid, (10 μL)). A Millipore filter (0.025 μm pore size, 25 mm diameter) was floated in a dish of water and the prepared solution dropped onto the centre of the membrane. After 15 min, the drop was removed and diluted with acetonitrile (20 μL). Mass spectrometry was then conducted on this solution.

3.2.4 Calculation of Extinction Coefficient of o-Nitrophenol o-Nitrophenol (14 mg, 0.10 mmol) was dissolved in phosphate buffer (10 mL, 50 mM, pH 6.49) to give a 10 mM solution. From this stock solution a range of concentrations were prepared (12.5, 25.0, 50.0, 75.0, 100, 1000 μM) by serial dilution. An aliquot of each o-nitrophenol solution concentration and a blank sample of phosphate buffer (300 μL, 50 mM, pH 6.49) was dispensed into seven sealed 1.5 mL Eppendorf tubes. The tubes were incubated in a Techni Dri Block at 45° C. Simultaneously a 96-well flat bottom microtitre plate was incubated at 45° C. in a plate reader. After 5 min, 200 μL of each o-nitrophenol solution and the phosphate buffer was dispensed into a well in the microtitre plate. The plate containing the solutions and buffer was then incubated in the plate reader at 45° C. After 5 min the absorbance at 405 nm was measured. A straight line graph of absorption against concentration gave a gradient equal to the extinction coefficient according to Beer-Lambert Law.

3.2.5 Kinetic Assays

Substrate solutions (concentration 10 mM in 50 mM pH 6.5 phosphate buffer) were prepared. Kinetic assays were conducted in a 96-well flat bottom microtitre plate. Eight substrate concentrations were chosen for the assay from the range 0.05 mM to 10 mM (prepared from 10 mM stock solution), based on previous experimental experience of the kinetics of each enzyme (default range 0.05 mM to 2.00 mM)*. The enzyme stock solution (~1 mgmL$^{-1}$) was diluted between 16- and 80-fold depending on the kinetic parameters determined*. The enzyme solution (496 μL) was dispensed into a 1.5 mL sealed Eppendorf tube. Into eight further Eppendorf tubes a portion of each substrate solution (650 μL) was dispensed. The tubes were incubated in a Techni Dri Block at 45° C. Simultaneously a 96-well flat bottom microtitre plate was incubated at 45° C. in a plate reader. After 5 min, substrate (190 μL) was dispensed into the microtitre plate in triplicate and 24 aliquots of the enzyme solution (15 μL) were dispensed into the plate. The plate containing the enzyme and substrate solutions was then incubated in the plate reader at 45° C. to allow equilibration. After 5 min, enzyme solution (10 μL) was added to each well containing substrate solution to initiate the reaction and the data collection commenced. Release of p-nitrophenol/o-nitropbenol was measured by absorbance at 405 μm, with an automix of 3 s before the first read and Is between every subsequent read. The run time chosen was between 6 min and 10 min*, and readings were taken at intervals of between 6 s and 10 s*.

* See Table 10 for specific substrate solutions, enzyme concentrations, run times and intervals used in each experiment.

TABLE 10

Kinetic assay experimental details

| Expt | Enzyme | [Enzyme]/mM | Substrate | [Substrate] Used/mM | Run t/min | Interval/s |
|---|---|---|---|---|---|---|
| 1 | C344S | $3.7 \times 10^{-5}$ | pNPGal | 0.10, 0.25, 0.50, 0.75, 1.00, 1.50, 2.00, 5.00. | 10 | 10 |
| 2 | C344SM439C | $1.9 \times 10^{-5}$ | pNPGal | 0.25, 0.50, 0.75, 1.00, 1.50, 2.00, 5.00, 10.00. | 6 | 6 |
| 3 | C344SM439C-Me | $3.9 \times 10^{-5}$ | pNPGal | 0.10, 0.25, 0.50, 0.75, 1.00, 1.50, 2.00, 5.00. | 10 | 10 |
| 4 | C344SM439C-NMe$_3^+$ | $3.0 \times 10^{-5}$ | pNPGal | 0.10, 0.25, 0.50, 0.75, 1.00, 1.50, 2.00, 5.00. | 10 | 10 |
| 5 | C344SM439C-COOH | $4.6 \times 10^{-5}$ | pNPGal | 0.10, 0.25, 0.50, 0.75, 1.00, 1.50, 2.00, 5.00. | 10 | 10 |
| 6 | WT | $2.3 \times 10^{-5}$ | oNPGalP6 | 0.05, 0.10, 0.2, 0.50, 0.75, 1.00, 1.50, 2.00. | 10 | 10 |
| 7 | C344S | $1.5 \times 10^{-5}$ | oNPGalP6 | 0.05, 0.10, 0.2, 0.50, 0.75, 1.00, 1.50, 2.00. | 10 | 10 |
| 8 | C344SM439C | $1.0 \times 10^{-5}$ | oNPGalP6 | 0.05, 0.10, 0.2, 0.50, 0.75, 1.00, 1.50, 2.00. | 10 | 10 |
| 9 | C344SM439C-Me | $1.9 \times 10^{-5}$ | oNPGalP6 | 0.10, 0.25, 0.50, 0.75, 1.00, 1.50, 2.00, 5.00. | 10 | 10 |
| 10 | C344SM439C-NMe$_3^+$ | $1.5 \times 10^{-5}$ | oNPGalP6 | 0.10, 0.25, 0.50, 0.75, 1.00, 1.50, 2.00, 5.00. | 10 | 10 |
| 11 | C344SM439C-COOH | $4.6 \times 10^{-5}$ | oNPGalP6 | 0.10, 0.25, 0.50, 0.75, 1.00, 1.50, 2.00, 5.00. | 10 | 10 |

3.2.6 Kinetic Assay Data Manipulation

A graph of concentration of the released chromophore (either pNP or oNP) against time was drawn for each concentration using Microsoft Excel. When substrate concentration becomes limiting, the plot fails to produce a straight line. The data up to this point was used to calculate the rate of chromophore release. These gradients were entered into Grafit, which calculated $K_M$ and $v_{max}$ from the Michelis-Menten and Lineweaver-Burk plots. From these $k_{cat}$ and $k_{cat}/K_M$ could be calculated. To compare activities of the different enzymes column charts of $\ln(\{k_{cat}/K_M\}$ mutant/$\{k_{cat}/K_M\}$ WT) were constructed.

3.2.7 Background Substrate Degradation Determination

Substrate (1 mL of a 10 mM solution) was dispensed into a sealed 1.5 mL Eppendorf tube. The tube was incubated in a Techni Dri Block at 45° C. Simultaneously a 96-well flat bottom microtitre plate was incubated at 45° C. in a plate reader. After 5 min, substrate solution (100 µL) was dispensed into a well in the microtitre plate. The plate containing the substrate solution was then incubated in the plate reader at 45° C. After 5 min the absorbance at 405 nm was measured. The solution continued to be incubated in the Techni Dri Block for 70 h, and further measurements were taken at various time intervals. Before each measurement the plate containing substrate solution was incubated in the plate reader at 45° C. for 5 min.

3.3 Procedures

Sodium Methanethiosulfonate 21

A mixture of methane sulfinic acid sodium salt 20 (2.50 g, 24.5 mmol) and sulfur (784 mg, 24.5 mmol) in methanol (150 mL) was heated to reflux under argon. After 20 min, the sulfur had dissolved and the hot solution was filtered. The filtrate was concentrated in vacuo to afford a white solid which was washed with anhydrous ethanol (30 mL) and dried in vacuo to afford sodium methanethiosulfonate 21 (2.40 g, 73%) as a white crystalline solid; m.p. 271-272° C. (ethanol) [Lit. 272-273.5° C.]; $^{21}v_{max}$ (thin film) 1323, 1085 (S—SO$_2$)cm$^{-1}$; $\delta_H$(200 MHz, D$_2$O) 3.26 (3H, s, CH$_3$).

2-Carboxyethyl Methanethiosulfonate 16

A solution of 3-bromopropionic acid 22 (571 mg, 3.73 mmol) and sodium methanethiosulfonate 21 (511 mg, 3.81 mmol) in DMF (5 mL) was stirred under argon at 70° C. After 2 h, t.l.c. (ethyl acetate:methanol, 4:1) indicated the formation of two products (R$_f$ 0.3, 0.6) and the absence of any starting material (R$_f$ 0.2). The reaction mixture was cooled to room temperature, water (10 mL) was added and the resulting mixture extracted with ether (3×20 mL). The organic extracts were combined, washed with brine (30 mL), dried (MgSO$_4$), filtered and concentrated in vacuo. The residue was purified by flash column chromatography (DCM:ether, 3:1 (acetic acid, 0.6%)) to yield 2-carboxyethyl methanethiosulfonate 16 (438 mg, 64%) as a white crystalline solid; m.p. 44-46° C. (ethyl acetate/petrol) [Lit. 44-48° C. m.p., value obtained from Toronto Research Chemicals Inc. website (www.trc-canada.com), nmr spectra assigned using Chemical Concepts SpecInfo]; $v_{max}$ (thin film) 1716 (st, C=O), 1312, 1130 (S—SO$_2$)cm$^{-1}$, $\delta_H$(400 MHz, CDCl$_3$) 2.94 (2H, t, J$_{1,2}$ 6.7Hz, 2 x H-2), 3.36 (3H, s, CH$_3$), 3.38 (2H, t, 2 x H-1); $\delta_C$ (100.6 MHz, CDCl$_3$) δ0.6 (t, C-1), 34.4 (t, C-2), 50.6 (q, CH$_3$), 176.7 (s, C=O); m/z (ES-) 183 (M-H$^+$, 100%). HRMS (ES-) Calcd. For C$_4$H$_7$O$_4$S$_2$ (M-H$^-$) 182.9786.
Found 182.9788).

2-(Trimethylammonium)ethyl Methanethiosulfonate Bromide 15

A solution of sodium methane thiosulfonate 21 (472 mg, 3.52 mmol) and 2-bromoethyltrimethylammoniun bromide 23 (838 mg, 3.39 mmol) in anhydrous methanol (7 mL) was heated to reflux under argon. After 48 h, t.l.c (ethyl acetate: methanol, 4:1) indicated formation of one product (R$_f$ 0.0) along with some remaining starting material (Rr 0.4). The solution was cooled to −78° C., then immediately allowed to warm to −15° C. The white precipitate thus formed was filtered and dried in vacuo to afford 2-(trimethylammonium) ethyl methanethiosulfonate bromide 15 (356 mg, 36%) as a white crystalline solid; m.p. 155.5-156.5° C. (ethanol/ether) [Lit. 157.5-158.5° C. (ethanol)]) Davis, B. G., Khurntaveepom, K., Bott, R. R., and Jones, J. B., *Bioorg. Med. Chem.* 7, 2303-2311 (1999)); $v_{max}$ (thin film) 1317, 1132 (S—SO$_2$) cm$^{-1}$; $\delta_H$ (400 MHz, D$_2$O) 3.09 (9H, s, N(CH$_3$)$_3$), 3.47 (3H, s, CH$_3$SO$_2$), 3.52-3.55 (2H, m, 2 x H-1), 3.64-3.68 (2H, m, 2 x H-2).

6-Azido-6-deoxy-1,2:3,4-diisopropylidene-α-D-galactopyranose 33

Toluene (10 mL) was added to a stirred suspension of sodium azide (2.60 g, 40.0 mmol) in water (2 mL). The reaction mixture was cooled to 5° C. and sulfuric acid (1.0 mL, 20.0 mmol) added dropwise. The reaction mixture was stirred under argon at 5° C. for 40 min. The organic layer was removed by syringe and dried (Na$_2$SO$_4$). The hydrazoic acid thus formed was standardised against potassium hydroxide (0.072 M aqueous solution). Triphenyl phosphine (2.53 g, 9.63 mmol) was dissolved in toluene (20 mL) and diisopropyl azodicarboxylate (1.9 mL, 9.63 mmol) added. The reaction mixture was stirred under argon for 10 min then added to a flask containing a solution of 1,2:3,4-diisopropylidene-α-D-galactopyranose 32 (1.00 g, 3.85 mmol) and hydrazoic acid (11.3 mL of a 0.85 M solution in toluene, 9.63 mmol) in toluene (20 mL). After 67 h t.l.c. (petrol:ethyl acetate, 2:1) indicated the formation of a major product (R$_f$ 0.5) and the absence of starting material (R$_f$ 0.2). The reaction mixture was diluted with ether (50 mL), washed with sodium bicarbonate (3×50 mL of a saturated aqueous solution), dried (MgSO$_4$), filtered and concentrated in vacuo. The residue was purified by flash column chromatography (petrol:ethyl acetate, 2:1) to afford 6-azido-6-deoxy-1,2:3,4-diisopropylidene-α-D-galactopyranose 33 (1.09 g, 97%) as a pale orange oil; [α]$_D^{25}$ −68.7 (c, 0.8 in CHCl$_3$) [Lit. [α]$_D^{21}$ −92.1 (c, 1.48 in CHCl$_3$ containing 0.75% EtOH)] (Szarek, W. A. and Jones, J. K. N., *Can. J. Chem.* 43, 2345-56 (1965))], $v_{max}$ (thin film) 2102 (sh, N$_3$)cm$^{-1}$; $\delta_H$ (400 MHz, CDCl$_3$) 1.34, 1.35, 1.46, 1.55 (12H, 4 x s, 4 x CH$_3$), 3.37 (1H, dd, J$_{5,6}$ 5.4 Hz, J$_{6,6'}$ 12.6 Hz, H-6), 3.52 (1H, dd, J$_{5,6'}$ 7.9 Hz, H-6'), 3.90-3.94 (1H, m, H-5), 4.20 (1H, dd, J$_{3,4}$ 7.9 Hz, J$_{4,5}$ 1.9 Hz, H-4), 4.34 (1H, dd, J$_{1,2}$ 5.1 Hz, J$_{2,3}$ 2.5 Hz, H-2), 4.64 (1H, dd, H-3), 5.55 (11H, d, H-1). Alternative synthesis of 6-azido-6-deoxy-1,2:3,4-diisopropylidene-α-D-galactopyranose 33. A solution of sodium azide (33 mg, 0.51 mmol) in DMF (5 mL) was added to a solution of 1,2:3,4-diisopropylidene-6-trifluoromethanesulfonate-α-D-galactopyranose 34 (96 mg, 0.24 mmol) in DMF (5 mL). The reaction mixture was stirred under argon at room temperature. After 19 h, the reaction mixture was heated to 45° C. After 23 h, t.l.c. (petrol:ethyl acetate, 2:1) showed a single spot since the major product (R$_f$ 0.6) co-ran with the starting material. The DMF was removed in vacuo. The residue was dissolved in DCM (100 mL), neutralised with sodium bicarbonate (100 mL), washed with brine (3×30 mL), dried (MgSO$_4$), filtered and concentrated in vacuo. The residue was purified by flash column chromatography (petrol:ethyl acetate, 2:1) to afford 6-azido-6-deoxy-1, 2:3,4-diisopropylidene-α-D-galactopyranose 33 (70 mg, 80%) as a pale orange oil identical to that previously described.

1,2:3,4-Diisopropylidene-6-trifluoromethane-sulfonate-α-D-galactopyranose 34

1,2:3,4-diisopropylidene-α-D-galactopyranose 32 (1.05 g, 4.04 mmol) was dissolved in dichloromethane (15 mL). Pyridine (470 µl, 5.77 mmol) and trifluoromethane sulfonic anhydride (710 µl, 4.23 mmol) were added. The reaction mixture was stirred under argon. After 2 h, t.l.c. (petrol:ethyl acetate, 2:1) indicated the formation of two products (R$_f$ 0.1, 0.6) and the absence of any starting material ($R_f$ 0.2). The reaction mixture was diluted with dichloromethane (50 mL), washed with sodium bicarbonate (4×30 mL of a saturated aqueous solution), dried ($MgSO_4$), filtered and concentrated in vacuo. The residue was purified by flash column chromatography (petrol:ethyl acetate, 2:1) to afford 1,2:3,4-diisopropylidene-trifluoromethanesulfonate-α-D-galactopyranose 34 (0.66 g, 42%) as a pale pink solid $R_f$ 0.6 (petrol:ethyl acetate, 2:1); m.p. 47.7-48.1° C. (ethanol/ether) [Lit. 48.5-50.0° C. (hexane)] (Barrette, E. P. and Goodman, L., J. Org. Chem. 49, 176-178 (1984))]; $[\alpha]_D^{25}$ −42.6 (c, 0.7 in $CDCl_3$) [Lit. $[\alpha]_D^{27}$ 49.9 (C, 1.48 in $CHCl_3$)]; $\nu_{max}$ (thin film) 1415, 1206 (s, $SO_2$)cm$^{-1}$; $\delta_H$ (400 MHz, $CD_3OD$) 1.33, 1.34, 1.41, 1.50 (12H, 4 x s, 4 x $CH_3$), 4.13-4.16 (1H, m, H-5), 4.29 (1H, dd, $J_{3,4}$ 7.8 Hz, $J_{4,5}$ 2.0 Hz, H-4), 4.41 (1H, dd, $J_{1,2}$ 4.9 Hz, $J_{2,3}$ 2.7 Hz, H-2), 4.57 (1H, dd, $J_{5,6}$ 8.5 Hz, $J_{6,6'}$ 10.8 Hz, H-6), 4.68 (1H, dd, H-3), 4.75 (1H, dd, $J_{5,6'}$ 3.2 Hz, H-6'), 5.51 (1H, d, H-1).

6-Azido-6-deoxy-D-galactopyranose 35

6-azido-6-deoxy-1,2:3,4-diisopropylidene-α-D-galactopyranose 33 (100 mg, 0.35 mmol) was dissolved in acetic acid (5 mL of an 80% by volume aqueous solution). The reaction mixture was stirred at 70° C. After 69 h, t.l.c. (petrol:ethyl acetate, 2:1) indicated the formation of a major product ($R_f$ 0.0) and the absence of any starting material ($R_f$ 0.6). The ethanoic acid was removed in vacuo. The residue was purified by flash column chromatography (ethyl acetate:methanol, 4:1) to afford 6-azido-6-deoxy-D-galactopyranose 35 (α:β, 1:1) (57 mg, 63%) as a white crystalline solid $R_f$ 0.5 (ethyl acetate:methanol, 4:1); m.p. 58.0-60.0 C (ethanol/ether), $[\alpha]_D^{25}$+86.0 (c, 0.5 in $H_2O$); $\nu_{max}$ (thin film) 3310 (br, OH), 2117 (sh, $N_3$)cm$^{-1}$; $\delta_H$ (400 MHz, $CD_3OD$) 3.35-3.41 (3H, m, α-H-6, β-H-3, β-H-6), 3.48-3.58 (4H, m, α-H-3, α-H-6', β-H-2, β-H-6'), 3.70-3.83 (4H, m, α-H-2, α-H-4, β-H-3, β-H-4), 4.09-4.16 (2H, m, α-H-5, β-H-5), 4.48 (1H, d, $J_{\beta1,2}$ 7.4 Hz, β-H-1), 5.18 (1H, d, $J_{\alpha1,2}$ 3.6 Hz, α-H-1).

6-Azido-6-deoxy-1,2,3,4-tetra-O-acetyl-D-galactopyranose 36

4-(Dimethylamino)pyridine (1 mg, 0.01 mmol) and pyridine (4.3 mL, 55 mmol) were added to a stirred suspension of 6-azido-6-deoxy-D-galactopyranose 35 (2.24 g, 10.9 mmol) in acetic anhydride (5.2 mL, 54.65 mmol). The reaction mixture was stirred at RT. After 75 h, t.l.c. (petrol:ethyl acteate, 2:1) indicated the formation of one product ($R_f$ 0.4) and the absence of any starting material ($R_f$ 0.0). The reaction mixture was diluted with DCM (150 mL), neutralised with sodium bicarbonate (3×100 mL of a saturated aqueous solution), washed with brine (100 mL), dried (gSO$_4$), filtered and concentrated in vacuo. The residue was purified by flash column chromatography (petrol:ethyl acetate, 2:1) to afford 6-azido-6-deoxy-1,2,3,4-tetra-O-acetyl-D-galactopyranose 36 (α:β, 0.8:1) (3.26 g, 80%) as a colourless oil, $[\alpha]_D^{25}$+49.5 (c, 0.9 in $CDCl_3$); $\nu_{max}$ (thin film) 2106 (sh, $N_3$), 1748 (St, C=O)cm$^{-1}$; $\delta_H$ (500 MHz, $CDCl_3$) 1.99-2.19 (24H, m, 8 x $CH_3$), 3.46-3.67 (4H, m, α-H-6, α-H06', β-H-6, β-H-6'), 3.82 (1H, at, β-H-5), 4.10-4.14 (2H, m, α-H-5, β-H-4), 5.04 (1H, dd, $J_{\beta2,3}$ 10.2 Hz, $J_{\beta3,4}$ 3.2 Hz, β-H-3), 5.30-5.45 (4H, m, α-H-2, α-H-3, α-H-4, β-H-2), 5.69 (1H, d, $J_{\beta1,2}$ 8.2 Hz, β-H-1), 6.37 (1H, d, $J_{\alpha1,2}$ 3.9 Hz, α-H-1). Alternate synthesis of 6-azido-6-deoxy-1,2,3,4-tetra-O-acetyl-D-galactopyranose 36. A warmed portion of iodine (10 mg, 0.04 mmol) in acetic anhydride (5 ml, 53 mmol) was added to a stirred suspension of 6-azido-6-deoxy-D-galactopyranose 35 (204 mg, 1.0 mmol) in acetic anhydride (5 ml, 53 mmol), and the reaction mixture was cooled in ice. After 5 min, the reaction mixture was allowed to warm to RT. After 5½ h, t.l.c (petrol:ethyl acetate, 2:1) indicated the formation of several products ($R_f$ 0.2-0.4) and the absence of any starting material ($R_f$ 0.0). The reaction mixture was diluted with DCM (50 mL), washed with sodium thiosulfate (50 mL of a 10% aqueous solution), neutralized with sodium bicarbonate (6×100 mL of a saturated aqueous solution), dried ($MgSO_4$), filtered and concentrated in vacuo. The residue was purified by flash column chromatography (petrol:ethyl acetate, 2:1) to afford 6-azido-6-deoxy-1,2,3,4-tetra-O-acetyl-D-galactopyranose 36 (α:β, 1:1) (182 mg, 49%) $R_f$ 0.2 (petrol:ethyl acetate, 2:1) as a colourless oil identical to that previously described. In a subsequent reaction 1,2,3,4-tetra-O-acetyl-α-D-galactopyranose was isolated as a white crystalline solid; m.p. 89.9-90.3° C. (ethanol/ether) [Lit. 90° C. (ethanol) (Jezo, I. and Zemek, J., *Chemicke Zvesti*, 33, 533-541 (1979)]; $[\alpha]_D^{25}$+63.4 (c, 0.4 in $CHCl_3$) [Lit. $[\alpha]_D^{23}$ +97 (c, 1 in $CHCl_3$)]; $\nu_{max}$ (thin film) 2105 (sh, $N_3$), 1642 (st, C=O)cm$^{-1}$; $\delta_H$ (400 MHz, $CDCl_3$) 2.00, 2.01, 2.02, 2.03 (12H, 4 x s, 4 x $CH_3$), 3.28 (1H, dd, $J_{5,6}$ 5.7 Hz, $J_{6,6'}$ 12.8 Hz, H-6), 3.45 (1H, dd, $J_{5,6}$ 7.5 Hz, H-6'), 4.24 (1H, m, H-5), 5.35 (2H, m, H-2, H-3), 5.49 (1H, d, H-4), 6.41 (1H, br, H-1).

2,3,4-Tri-O-acetyl-6-azido-6-deoxy-α-D-galactopyranosyl Bromide 37

Hydrogen bromide (2 mL of a 30% solution in acetic acid) was added to a solution of 6-azido-6-deoxy-1,2,3,4-tetra-O-acetyl-galactopyranose 36 (α:β, 0.8:1) (320 mg, 0.86 mmol) in anhydrous DCM (10 mL). The mixture was stirred under argon at 0° C. After 1¾h, t.l.c. (petrol:ethyl acetate, 2:1) indicated the formation of two products ($R_f$ 0.5, 0.2) with some remaining starting material ($R_f$ 0.3). The reaction mixture was quenched with ice/water (30 mL), diluted with DCM (40 mL), neutralized with sodium bicarbonate (2×40 mL), washed with brine (40 mL), dried ($MgSO_4$), filtered and concentrated in vacuo to yield 350 mg of crude product, which was used without further purification, but a small portion was retained and purified by flash column chromatography (DCM:ether, 60:1) to afford 2,3,4-tri-O-acetyl-6-azido-6-deoxy-α-D-galactopyranosylbromide 37 as a white solid $R_f$ 0.5 (60:1, DCM:ether); m.p. 81.5-82.2C (ether/petrol) [Lit. 82-83° C. (ether/petrol) Jezo, I. and Zemek, J., *Chemicke Zvesti*, 33, 533-541 (1979)]; $[\alpha]_D^{25}$+70.8 (c, 1.7 in $CHCl_3$) [Lit. $[\alpha]_D^{22}$ +133.8 (c, 1 in $CHCl_3$)], $\nu_{max}$ (thin film) 2107 (sh, $N_3$), 1750 (st, C=O)cm$^{-1}$; $\delta_H$ (400 MHz, $CDCl_3$) 2.03, 2.12, 2.18 (9H, 3 x s, 3 x $CH_3$), 3.30-3.40 (2H, m, H-6, H-6'), 4.47 (1H, t, H-5), 5.04 (1H, dd, $J_{1,2}$ 4.0, $J_{2,3}$ 10.7, H-2), 5.43 (1H, dd, $J_{3,4}$ 3.2, H-3), 5.69 (1H, m, H-4), 6.69 (1H, d, H-1).

1,3,4-Tri-O-acetyl-6-azido-6-deoxy-2-hydroxy-α-D-galactopyranose 39

2,3,4-tri-O-acetyl-6-azido-6-deoxy-α-D-galactopyranosylbromide 37 (100 mg, 0.25 mmol) and p-nitrophenol (37 mg, 0.27 mmol) were dissolved in DCM. This solution was added to a stirred suspension of 2,6-di-tert-butyl-4-methylpyridine (37 mg, 0.18 mmol), silver triflate (87 mg, 0.30 mmol) and molecular sieves (3 Å) in DCM (7 ml). The reaction mixture was stirred under argon. After 1 h, t.l.c. (petrol:ethyl acetate, 2:1) indicated complete consumption of starting material ($R_f$ 0.4). The reaction mixture was filtered through celite, concentrated in vacuo and co-evaporated with water. The residue was purified by flash column chromatography (DCM:ether, 30:1) to afford 1,3,4-tri-O-acetyl-6- azido-6-deoxy-2-hydroxy-α-b-galactopyranose 39 (55 mg, 65%) as a colourless oil ($R_f$ 0.5); partial data $[\alpha]_D^{25}$ +68.7 (c, 0.2 in CHCl$_3$); $\nu_{max}$ (thin film) 3432 (br, OH), 2101 (sh, N$_3$) 1644 (st, C=O)cm$^{-1}$; $\delta_H$ (400 MHz, CDCl$_3$) 2.02, 2.03, 2.17, 2.18 (12H, 4 x s, 4 x CH$_3$), 3.28 (1H, dd, $J_{5,6}$ 7.8 Hz, $J_{6,6'}$ 10.3Hz, H-6), 3.35 (1H, dd, $J_{5,6'}$ 6.2 Hz, H-6'), 4.31 (1H, m, H-5), 5.32 (1H, dd, $J_{2,3}$ 3.2 Hz, $J_{2,3}$ 11.0 Hz, H-2), 5.37 (1H, dd, $J_{3,4}$ 3.1 Hz, H-3), 5.69-5.70 (1H, m, H-4), 6.37 (1H, d, H-1); $\delta_C$ (100.6 MHz, CDCl$_3$) 20.5, 20.6, 20.9 (3 x q, 3 x CH$_3$), 27.4 (t, C-6), 66.2 (d, C-2), 67.5 (d, C-3), 67.7 (d, C-4), 71.2 (d, C-5), 89.6 (d, C-1), 168.9, 169.9, 170.1 (3 x s, 3 x C=O).

p-Nitrophenyl 2,3,4-tri-O-acetyl-6-azido-6-deoxy-α-D-galactopyranoside 40

Boron trifluoride diethyl etherate (80 μl, 0.70 mmol) was added to a stirred solution of 6-azido-6-deoxy-1,2,3,4-tetra-O-acetyl-D-galactopyranose 36 (α:β, 1:1) (52 mg, 0.139 mmol) in DCM (5 mL). The solution was stirred under argon at RT. After 20 min a solution of p-nitrophenol (19 mg, 0.14 mmol) in DCM (5 mL) was added to the reaction mixture and stirring under argon maintained. After 65 min, t.l.c. (DCM: ether, 60:1) indicated formation of two products ($R_f$ 0.1, 0.4) with some remaining starting material ($R_f$ 0.3). The DCM was removed in vacuo. The residue was diluted with chloroform (30 mL), washed with brine (3×30 mL), dried (MgSO$_4$), filtered and concentrated in vacuo. The residue was purified by flash column chromatography (DCM:ether, 60:1) to afford p-nitrophenyl 2,3,4-tri-β-acetyl-6-azido-6-deoxy-α-D-galactopyranoside 40 (9.7 mg, 14%) as a colourless oil; partial data $[\alpha]_D^{25}$ +18.3 (c, 0.5 in CHCl$_3$); $\nu_{max}$ (thin film) 3430 (br, OH), 2101 (sh, N$_3$), 1637 (st, C=O)cm$^{-1}$; $\delta_H$ (500 Mz, CDCl$_3$) 2.05, 2.09, 2.21 (9H, 3 x s, 3 x CH$_3$), 3.13 (1H, dd, $J_{5,6}$ 4.2 Hz, $J_{6,6'}$ 13.1 Hz, H-6), 3.46 (1H, dd, $J_{5,6'}$ 8.2 Hz, H-6'), 4.18 (1H, dd, H-5), 5.34 (1H, dd, $J_{2,3}$ 3.7 Hz, $J_{2,3}$ 10.9 Hz, H-2), 5.49 (1H, d, $J_{3,4}$ 3.0 Hz, H-4), 5.57 (1H, dd, H-3), 5.94 (1H, d, H-1) 7.21 (2H, J=9.3 Hz, 2 x C$\underline{H}$CHCNO$_2$), 8.26 (2H, 2 x C$\underline{H}$CNO$_2$); 5c (125.7 MHz, CDCl$_3$) 19.9, 20.0, 21.0 (3 x q, 3 x CH$_3$), 51.9 (t, C-6), 53.3 (d, C-2), 66.6 (d, C-3), 67.6 (d, C-4), 69.0 (d, C-5), 95.2 (d, C-1), 115.6, 115.7, 125.3 (3 x s, 3 x C=O), 116.9, 117.0 (2 x d, $\underline{C}$HCHCNO$_2$), 126.5, 126.6 (2 x d, $\underline{C}$HCNO$_2$), 140.8 (s, CNO$_2$), 167.2, 169.9, 170.2, 171.8 (4 x s, 3 x C=O, 1x $\underline{C}$CHCHCNO$_2$); m/z (CI+) 470 (M+NH$_4^+$, 10%).

o-Nitrophenyl β-D-galactopyranoside-6-phosphate 17 o-Nitrophenyl β-D-galactopyranoside 27 (903 mg, 3.0 mmol) was added to a mixture of trimethyl phosphate (7.5 mL, 64.8 mmol), water (0.05 mL, 3.0 mmol) and phosphorous oxychloride (0.84 mL, 9.0 mmol) at 0° C. The reaction mixture was stirred and after 2 h a change was observed from a white, cloudy suspension to a clear, yellow solution. After 3 h, t.l.c. (ethyl acetate:methanol, 4:1) indicated the formation of one product ($R_f$ 0.2) and the absence of any starting material ($R_f$ 0.3) Crushed ice (20 mL) was added and the reaction mixture neutralised with ammonia (5 mL of a 33% aqueous solution). The white crystalline solid thus formed was separated from the clear yellow solution by filtration, the filtrate concentrated in vacuo and co-evaporated with water (6×10 mL) to afford a white, crystalline solid. The residue was purified by flash column chromatography as follows; charcoal (10 g) and celite (10 g) were mixed together with hydrochloric acid (10 mL of a 1 M aqueous solution) and packed into a column. The white solid was dissolved in water (5 mL) and loaded onto the column. The column was eluted with water. Aliquots (1 mL) of each fraction were removed and tested for the presence of chloride ions by observing turbidity on addition of silver nitrate (1 mL of a 1 M aqueous solution). After elution with 1.75 L of water the presence of chloride ions were no longer detected. Further elution (water:pyridine, 2:1) yielded o-nitrophenyl β-D-galactopyranoside 6-phosphate 17 (701 mg, 62%) as a pale, yellow crystalline solid; m.p. 181.0-183.1° C. (ethanol/ether) [Lit. 180° C. (ethanol/ether)];[27] $[\alpha]_D^{25}$-31.1 (c, 0.2 in H$_2$O) [Lit. $[\alpha]_D^{20}$-40 (c, 2 in H$_2$O)];[27] $\nu_{max}$ (KBr) 3400 br, OH) 1527, 1355 (sh, C—NO$_2$), 1250 (sh, P=O)cm$^{-1}$, $\delta_H$ (400 MHz, D$_2$O) 1.17-1.29 (2H, m, 2 x C$\underline{H}$NH$_3$), 1.52-1.57 (2H, d, J=12.6 Hz, 2 x C$\underline{H}$CHCHCNH$_3$), 1.68-1.73 (4H, m, 4 x C$\underline{H}$CHCNH$_3$), 1.87 (4H, br, 4 x C$\underline{H}$CNH$_3$), 3.04 (2H, br, 2 x NH), 3.65-3.70 (2H, m, H-6, H-6'), 3.74-3.86 (3H, m, H-3, H-4, H-5), 3.91-3.92 (1H, m, H-1), 7.13-7.18 (1H, m, C$\underline{H}$CHCNO$_2$), 7.33-7.42 (1H, m, C$\underline{H}$CHCHCNO$_2$), 7.56-7.61 (H, m, C$\underline{H}$CHCHCNO$_2$), 7.83-7.86 (1H, m, C$\underline{H}$CNO$_2$).

All applications, including U.S. Appln. No. 60/416,263, and publications are incorporated by reference herein.

---

The invention claimed is:

1. A modified polypeptide having β-glycosidase activity, said polypeptide comprising an amino acid sequence selected from:
   (a) the amino acid sequence of SEQ ID NO:2 mutated at an amino acid residue or residues selected from the group consisting of W433, E432 and M439 and combinations thereof;
   (b) the amino acid sequence of a family 1 glycosyl hydrolase mutated at an amino acid residue or residues corresponding to an amino acid residue or residues selected from the group consisting of W433, E432 and M439 of SEQ ID NO:2 and combinations thereof; and
   (c) a variant of (a) having β-glycosidase activity and mutated at an amino acid residue or residues corresponding to an amino acid residue or residues selected from the group consisting of W433, E432 and M439 of SEQ ID NO:2 and combinations thereof, wherein said variant has at least 95% identity to SEQ ID NO:2 over the entire length of the sequence.

2. The polypeptide according to claim 1 in which the mutation is selected to broaden the substrate specificity of the polypeptide compared to a polypeptide not so modified.

3. The polypeptide according to claim 1, wherein the mutation is an amino acid substitution.

4. The polypeptide according to claim 1 in which the polypeptide comprises:
   (i) SEQ ID NO:2 having one or more of W433, E 432 and M439 substituted by cysteine, valine or alanine; or
   (ii) the amino acid sequence as defined in (b) or (c) having one or more of the amino acid residues corresponding to W433, E432 and M439 of SEQ ID NO:2 substituted by cysteine, valine or alanine.

5. The polypeptide according to claim 1, wherein the variant (c) has at least 99% identity to SEQ ID NO:2 over the entire length of the sequence.

6. The polypeptide according to claim 1, said polypeptide comprising the amino acid sequence of a family 1 glycosyl hydrolase mutated at an amino acid residue or residues corresponding to an amino acid residue or residues selected from the group consisting of W433, E432 and M439 of SEQ ID NO:2 and combinations thereof.

7. The polypeptide according to claim 6, wherein each of said mutation(s) consists of substitution of the amino acid residue by an amino acid residue selected from the group consisting of cysteine, valine or alanine.

8. The polypeptide according to claim 1 having β-glycosidase activity, and comprising an amino acid sequence having at least 95% identity to SEQ ID NO:2 over the entire length of the sequence and mutated at an amino acid residue or residues corresponding to an amino acid residue or residues selected from the group consisting of W433, E432 and M439 of SEQ ID NO:2 and combinations thereof.

9. A modified polypeptide having β-glycosidase activity, said polypeptide comprising an amino acid sequence selected from:
   (a) the amino acid sequence of SEQ ID NO:2 mutated at an amino acid residue or residues selected from the group consisting of W433, E432 and M439 and combinations thereof, wherein each of said mutated amino acid residue(s) is substituted with a cysteine residue;
   (b) the amino acid sequence of a family 1 glycosyl hydrolase mutated in an amino acid residue corresponding to at least one of W433, E432 and M439 of SEQ ID NO:2 and combinations thereof, wherein each of the mutated amino acid residue(s) is substituted by a cysteine residue; and
   (c) a variant of (a) having β-glycosidase activity and mutated at an amino acid residue or residues corresponding to an amino acid residue or residues selected from the group consisting of W433, E432 and M439 of SEQ ID NO:2 and combinations thereof, wherein each of the mutated amino acid residue(s) is substituted by a cysteine residue and wherein said variant has at least 95% identity to SEQ ID NO:2 over the entire length of the sequence.

10. The polypeptide according to claim 9, wherein the cysteine residue introduced by the mutation is chemically modified.

11. The polypeptide according to claim 10, wherein the cysteine residue is modified so as to comprise a positively-charged group.

12. The polypeptide according to claim 11, wherein the positively-charged group is of formulas —(CH)n-N$^+$(R)$_3$, wherein n is a positive integer from 1 to 4 and each R, which may be the same or different, is H or a $C_1$-$C_4$ alkyl group.

13. The polypeptide according to claim 12, wherein the positively charged group is —$CH_2CH_2N^+(CH_3)_3$.

14. The polypeptide according to claim 10, wherein the cysteine residue is modified so as to comprise a negatively-charged group.

15. The polypeptide according to claim 14, wherein the negatively-charged group is of formula —$(CH_2)$n-$SO_3^-$ or —$(CH_2)$n-$COO^-$, wherein n is a positive integer from 1 to 4.

16. The polypeptide according to claim 15, wherein the negatively-charged group is of formula —$(CH_2)$n-$SO_3^-$.

17. The polypeptide according to claim 10, wherein the cysteine residue is modified so as to comprise an uncharged group.

18. The polypeptide according to claim 17, wherein the uncharged group is a $C_1$-$C_4$ alkyl group.

19. The polypeptide according to claim 18, wherein the uncharged group is methyl.

20. The polypeptide according to claim 10, wherein the family 1 glycosyl hydrolase is *Sulfolobus solfataricus* β-glycosidase.

21. The polypeptide according to claim 9 having β-glycosidase activity, and comprising an amino acid sequence having at least 95% identity to SEQ ID NO:2 over the entire length of the sequence and mutated at an amino acid residue or residues corresponding to an amino acid residue or residues selected from the group consisting of W433, E432 and M439 of SEQ ID NO:2 and combinations thereof, wherein each of the mutated amino acid residue(s) is substituted by a cysteine residue.

22. A method for hydrolysing a β-glycoside, which method comprises contacting a glycoside substrate with a modified polypeptide having β-glycosidase activity, said polypeptide comprising an amino acid sequence selected from:
   (a) the amino acid sequence of SEQ ID NO:2 mutated at an amino acid residue or residues selected from the group consisting of W433, E432 and M439 and combinations thereof;
   (b) the amino acid sequence of a family 1 glycosyl hydrolase mutated at an amino acid residue or residues corresponding to an amino acid residue or residues selected from the group consisting of W433, E432 and M439 of SEQ ID NO:2 and combinations thereof; and
   (c) a variant of (a) having β-glycosidase activity and mutated at an amino acid residue or residues corresponding to an amino acid residue or residues selected from the group consisting of W433, E432 and M439 of SEQ ID NO:2 and combinations thereof, wherein said variant has at least 95% identity to SEQ ID NO:2 over the entire length of the sequence.

23. The method according to claim 22, wherein the glycoside substrate is selected from the group consisting of a glucoside, a galactoside, a fucoside, a xyloside, a mannoside, and a glucuronide.

24. The method according to claim 22, wherein the polypeptide is contacted with a sample containing at least two different glycosides.

25. The method according to claim 22, wherein said polypeptide has β-glycosidase activity, and wherein said polypeptide comprises an amino acid sequence having at least 95% identity to SEQ ID NO:2 over the entire length of the sequence and mutated at an amino acid residue or residues corresponding to an amino acid residue or residues selected from the group consisting of W433, E432 and M439 of SEQ ID NO:2 and combinations thereof.

26. A method for hydrolysing a β-glycoside, which method comprises contacting a glycoside substrate with a modified polypeptide having β-glycosidase activity, said polypeptide comprising an amino acid sequence selected from:
   (a) the amino acid sequence of SEQ ID NO:2 mutated at an amino acid residue or residues selected from the group consisting of W433C, E432C and M439C and combinations thereof, wherein each of said mutated amino acid residue(s) is substituted with a cysteine residue;

(b) the amino acid sequence of a family 1 glycosyl hydrolase mutated at an amino acid residue or residues corresponding to an amino acid residue or residues selected from the group consisting of W433, E432 and M439 of SEQ ID NO:2 and combinations thereof, wherein each of the mutated amino acid residue(s) is substituted by a cysteine residue; and (c) a variant of (a) having β-glycosidase activity and mutated at an amino acid residue or residues corresponding to an amino acid residue or residues selected from the group consisting of W433, E432 and M439 of SEQ ID NO:2 and combinations thereof, wherein each of the mutated amino acid residue(s) is substituted by a cysteine residue, and wherein said variant has at least 95% identity to SEQ ID NO:2 over the entire length of the sequence;

wherein the cysteine residue(s) introduced by the mutation of (a), (b) or (c) is chemically modified.

27. The method according to claim 26, wherein the glycoside substrate is selected from the group consisting of a glucoside, a galactoside, a fucoside, a xyloside, a mannoside, and a glucuronide.

28. The method according to claim 26, wherein the polypeptide is contacted with a sample containing at least two different glycosides.

29. The method according to claim 26, wherein said polypeptide has β-glycosidase activity, and wherein said polypeptide comprises an amino acid sequence having at least 95% identity to SEQ ID NO:2 over the entire length of the sequence and mutated at an amino acid residue or residues corresponding to an amino acid residue or residues selected from the group consisting of W433, E432 and M439 of SEQ ID NO:2 and combinations thereof, wherein each of the mutated amino acid residue(s) is substituted by a cysteine residue.

* * * * *

SEQUENCE LISTING

```
<160> NUMBER OF SEQ ID NOS: 23

<210> SEQ ID NO 1
<211> LENGTH: 2346
<212> TYPE: DNA
<213> ORGANISM: Sulfolobus solfataricus
<220> FEATURE:
<221> NAME/KEY: CDS
<222> LOCATION: (229)..(1698)
<223> OTHER INFORMATION:

<400> SEQUENCE: 1
aaggagaaac ttggcagttt ataacttgac agtaggttgt ggagtgatga ctggatcaat     60
actaggagga gtagcatata attacgttac acaattttat aacccaatat attcaataga    120
ccttatgctt atcctatcct ctattctaag attctcggta tctcccctat tcttgaccat    180
```

```
aaaagatact cgctcaaagc ttaaataata ttaatcataa ataaagtc atg tac tca      237
                                                     Met Tyr Ser
                                                       1 ttt cca aat agc ttt agg ttt ggt tgg tcc cag gcc gga ttt caa tca      285
Phe Pro Asn Ser Phe Arg Phe Gly Trp Ser Gln Ala Gly Phe Gln Ser
  5              10                  15 gaa atg gga aca cca ggg tca gaa gat cca aat act gac tgg tat aaa      333
Glu Met Gly Thr Pro Gly Ser Glu Asp Pro Asn Thr Asp Trp Tyr Lys
 20              25                  30                  35 tgg gtt cat gat cca gaa aac atg gca gcg gga tta gta agt gga gat      381
Trp Val His Asp Pro Glu Asn Met Ala Ala Gly Leu Val Ser Gly Asp
             40                  45                  50 cta cca gaa aat ggg cca ggc tac tgg gga aac tat aag aca ttt cac      429
Leu Pro Glu Asn Gly Pro Gly Tyr Trp Gly Asn Tyr Lys Thr Phe His
             55                  60                  65 gat aat gca caa aaa atg gga tta aaa ata gct aga cta aat gtg gaa      477
Asp Asn Ala Gln Lys Met Gly Leu Lys Ile Ala Arg Leu Asn Val Glu
         70                  75                  80 tgg tct agg ata ttt cct aat cca tta cca agg cca caa aac ttt gat      525
Trp Ser Arg Ile Phe Pro Asn Pro Leu Pro Arg Pro Gln Asn Phe Asp
 85                  90                  95 gaa tca aaa caa gat gtg aca gag gtt gag ata aac gaa aac gag tta      573
Glu Ser Lys Gln Asp Val Thr Glu Val Glu Ile Asn Glu Asn Glu Leu
100                 105                 110                 115 aag aga ctt gac gag tac gct aat aaa gac gca tta aac cat tac agg      621
Lys Arg Leu Asp Glu Tyr Ala Asn Lys Asp Ala Leu Asn His Tyr Arg
                120                 125                 130 gaa ata ttc aag gat ctt aaa agt aga gga ctt tac ttt ata cta aac      669
Glu Ile Phe Lys Asp Leu Lys Ser Arg Gly Leu Tyr Phe Ile Leu Asn
             135                 140                 145 atg tat cat tgg cca tta cct cta tgg tta cac gac cca ata aga gta      717
Met Tyr His Trp Pro Leu Pro Leu Trp Leu His Asp Pro Ile Arg Val
             150                 155                 160 aga aga gga gat ttt act gga cca agt ggt tgg cta agt act aga aca      765
Arg Arg Gly Asp Phe Thr Gly Pro Ser Gly Trp Leu Ser Thr Arg Thr
165                 170                 175 gtt tac gaa ttc gct aga ttc tca gct tat ata gct tgg aaa ttc gat      813
Val Tyr Glu Phe Ala Arg Phe Ser Ala Tyr Ile Ala Trp Lys Phe Asp
180                 185                 190                 195 gat cta gtg gat gag tac tca aca atg aat gaa cct aac gtt gtt gga      861
Asp Leu Val Asp Glu Tyr Ser Thr Met Asn Glu Pro Asn Val Val Gly
                200                 205                 210 ggt tta gga tac gtt ggt gtt aag tcc ggt ttt ccc cca gga tac cta      909
Gly Leu Gly Tyr Val Gly Val Lys Ser Gly Phe Pro Pro Gly Tyr Leu
             215                 220                 225 agc ttt gaa ctt tcc cgt agg cat atg tat aac atc att caa gct cac      957
Ser Phe Glu Leu Ser Arg Arg His Met Tyr Asn Ile Ile Gln Ala His
             230                 235                 240 gca aga gcg tat gat ggg ata aag agt gtt tct aaa aaa cca gtt gga     1005
Ala Arg Ala Tyr Asp Gly Ile Lys Ser Val Ser Lys Lys Pro Val Gly
             245                 250                 255 att att tac gct aat agc tca ttc cag ccg tta acg gat aaa gat atg     1053
Ile Ile Tyr Ala Asn Ser Ser Phe Gln Pro Leu Thr Asp Lys Asp Met
260                 265                 270                 275 gaa gcg gta gag atg gct gaa aat gat aat aga tgg tgg ttc ttt gat     1101
Glu Ala Val Glu Met Ala Glu Asn Asp Asn Arg Trp Trp Phe Phe Asp
                280                 285                 290 gct ata ata aga ggt gag atc acc aga gga aac gag aag att gta aga     1149
Ala Ile Ile Arg Gly Glu Ile Thr Arg Gly Asn Glu Lys Ile Val Arg
             295                 300                 305
```

```
gat gac cta aag ggt aga ttg gat tgg att gga gtt aat tat tac act      1197
Asp Asp Leu Lys Gly Arg Leu Asp Trp Ile Gly Val Asn Tyr Tyr Thr
            310                 315                 320 agg act gtt gtg aag agg act gaa aag gga tac gtt agc tta gga ggt      1245
Arg Thr Val Val Lys Arg Thr Glu Lys Gly Tyr Val Ser Leu Gly Gly
325                 330                 335 tac ggt cac gga tgt gag agg aat tct gta agt tta gcg gga tta cca      1293
Tyr Gly His Gly Cys Glu Arg Asn Ser Val Ser Leu Ala Gly Leu Pro
340                 345                 350                 355 acc agc gac ttc ggc tgg gag ttc ttc cca gaa ggt tta tat gac gtt      1341
Thr Ser Asp Phe Gly Trp Glu Phe Phe Pro Glu Gly Leu Tyr Asp Val
            360                 365                 370 ttg acg aaa tac tgg aat aga tat cat ctc tat atg tac gtt act gaa      1389
Leu Thr Lys Tyr Trp Asn Arg Tyr His Leu Tyr Met Tyr Val Thr Glu
            375                 380                 385 aat ggt att gcg gat gat gcc gat tat caa agg ccc tat tat tta gta      1437
Asn Gly Ile Ala Asp Asp Ala Asp Tyr Gln Arg Pro Tyr Tyr Leu Val
            390                 395                 400 tct cac gtt tat caa gtt cat aga gca ata aat agt ggt gca gat gtt      1485
Ser His Val Tyr Gln Val His Arg Ala Ile Asn Ser Gly Ala Asp Val
405                 410                 415 aga ggg tat tta cat tgg tct cta gct gat aat tac gaa tgg gct tca      1533
Arg Gly Tyr Leu His Trp Ser Leu Ala Asp Asn Tyr Glu Trp Ala Ser
420                 425                 430                 435 gga ttc tct atg agg ttt ggt ctg tta aag gtc gat tac aac act aag      1581
Gly Phe Ser Met Arg Phe Gly Leu Leu Lys Val Asp Tyr Asn Thr Lys
                440                 445                 450 aga cta tac tgg aga ccc tca gca cta gta tat agg gaa atc gcc aca      1629
Arg Leu Tyr Trp Arg Pro Ser Ala Leu Val Tyr Arg Glu Ile Ala Thr
            455                 460                 465 aat ggc gca ata act gat gaa ata gag cac tta aat agc gta cct cca      1677
Asn Gly Ala Ile Thr Asp Glu Ile Glu His Leu Asn Ser Val Pro Pro
            470                 475                 480 gta aag cca tta agg cac taa actttctcaa gtctcactat accaaatgag         1728
Val Lys Pro Leu Arg His
    485 tttttcttta atcttattct aatctcattt tcattagatt gcaatacttt cataccttct    1788 atattattta ttttgtacct tttgggatct acacttaatg ttagcctaat tggaaagtca    1848 tttagattta atactgttac cagtccatcc cttttaatta ttaatgaaaa taagaaggga    1908 taagtagcga tagcccttat tccgatatgg tctccaacaa tatcccttat tatctgcctt    1968 gcaacactag ggtagaactc tgaaatcaga tatggtaggt aagttgtaag tgataggacg    2028 taaactttag agttagagta agtgttctga aagactactg ggtgcaattc gacaccgtta    2088 taggcgtaaa ggattggcgt agctccgttt aatgaaaata taggtcctac agggaaattg    2148 gcttgcctct tgtaatatga ccaatagaac gttttcccat ccctggttaa cgcattgaca    2208 ctaacactat cgtaaatcaa gttaccgaca ccaagaattt tcagtgcagt atccccccaag   2268 acttcaataa gcttttagc tgcacttgct gtaaacatta agttaactcc cctattaagt    2328 aaatccacaa tatctaga                                                 2346

<210> SEQ ID NO 2
<211> LENGTH: 489
<212> TYPE: PRT
<213> ORGANISM: Sulfolobus solfataricus

<400> SEQUENCE: 2
```

-continued

```
Met Tyr Ser Phe Pro Asn Ser Phe Arg Phe Gly Trp Ser Gln Ala Gly
1               5                   10                  15

Phe Gln Ser Glu Met Gly Thr Pro Gly Ser Glu Asp Pro Asn Thr Asp
            20                  25                  30

Trp Tyr Lys Trp Val His Asp Pro Glu Asn Met Ala Ala Gly Leu Val
        35                  40                  45

Ser Gly Asp Leu Pro Glu Asn Gly Pro Gly Tyr Trp Gly Asn Tyr Lys
    50                  55                  60

Thr Phe His Asp Asn Ala Gln Lys Met Gly Leu Lys Ile Ala Arg Leu
65                  70                  75                  80

Asn Val Glu Trp Ser Arg Ile Phe Pro Asn Pro Leu Pro Arg Pro Gln
                85                  90                  95

Asn Phe Asp Glu Ser Lys Gln Asp Val Thr Glu Val Glu Ile Asn Glu
            100                 105                 110

Asn Glu Leu Lys Arg Leu Asp Glu Tyr Ala Asn Lys Asp Ala Leu Asn
        115                 120                 125

His Tyr Arg Glu Ile Phe Lys Asp Leu Lys Ser Arg Gly Leu Tyr Phe
    130                 135                 140

Ile Leu Asn Met Tyr His Trp Pro Leu Pro Leu Trp Leu His Asp Pro
145                 150                 155                 160

Ile Arg Val Arg Arg Gly Asp Phe Thr Gly Pro Ser Gly Trp Leu Ser
                165                 170                 175

Thr Arg Thr Val Tyr Glu Phe Ala Arg Phe Ser Ala Tyr Ile Ala Trp
            180                 185                 190

Lys Phe Asp Asp Leu Val Asp Glu Tyr Ser Thr Met Asn Glu Pro Asn
        195                 200                 205

Val Val Gly Gly Leu Gly Tyr Val Gly Val Lys Ser Gly Phe Pro Pro
    210                 215                 220

Gly Tyr Leu Ser Phe Glu Leu Ser Arg Arg His Met Tyr Asn Ile Ile
225                 230                 235                 240

Gln Ala His Ala Arg Ala Tyr Asp Gly Ile Lys Ser Val Ser Lys Lys
                245                 250                 255

Pro Val Gly Ile Ile Tyr Ala Asn Ser Ser Phe Gln Pro Leu Thr Asp
            260                 265                 270

Lys Asp Met Glu Ala Val Glu Met Ala Glu Asn Asp Asn Arg Trp Trp
        275                 280                 285

Phe Phe Asp Ala Ile Ile Arg Gly Glu Ile Thr Arg Gly Asn Glu Lys
    290                 295                 300

Ile Val Arg Asp Asp Leu Lys Gly Arg Leu Asp Trp Ile Gly Val Asn
305                 310                 315                 320

Tyr Tyr Thr Arg Thr Val Lys Arg Thr Glu Lys Gly Tyr Val Ser
                325                 330                 335

Leu Gly Gly Tyr Gly His Gly Cys Glu Arg Asn Ser Val Ser Leu Ala
            340                 345                 350

Gly Leu Pro Thr Ser Asp Phe Gly Trp Glu Phe Phe Pro Glu Gly Leu
        355                 360                 365

Tyr Asp Val Leu Thr Lys Tyr Trp Asn Arg Tyr His Leu Tyr Met Tyr
    370                 375                 380

Val Thr Glu Asn Gly Ile Ala Asp Asp Ala Asp Tyr Gln Arg Pro Tyr
385                 390                 395                 400

Tyr Leu Val Ser His Val Tyr Gln Val His Arg Ala Ile Asn Ser Gly
                405                 410                 415

Ala Asp Val Arg Gly Tyr Leu His Trp Ser Leu Ala Asp Asn Tyr Glu
```

```
                       420                 425                 430
Trp Ala Ser Gly Phe Ser Met Arg Phe Gly Leu Leu Lys Val Asp Tyr
            435                 440                 445

Asn Thr Lys Arg Leu Tyr Trp Arg Pro Ser Ala Leu Val Tyr Arg Glu
        450                 455                 460

Ile Ala Thr Asn Gly Ala Ile Thr Asp Glu Ile Glu His Leu Asn Ser
465                 470                 475                 480

Val Pro Pro Val Lys Pro Leu Arg His
                485

<210> SEQ ID NO 3
<211> LENGTH: 25
<212> TYPE: PRT
<213> ORGANISM: Sulfolobus shibatae

<400> SEQUENCE: 3

Trp Ser Leu Ala Asp Asn Tyr Glu Trp Ala Ser Gly Phe Ser Met Arg
1               5                   10                  15

Phe Gly Leu Leu Lys Val Asp Tyr Asn
            20                  25

<210> SEQ ID NO 4
<211> LENGTH: 25
<212> TYPE: PRT
<213> ORGANISM: Sulfolobus acidocaldarius

<400> SEQUENCE: 4

Trp Ser Leu Ala Asp Asn Tyr Glu Trp Ser Ser Gly Phe Ser Met Arg
1               5                   10                  15

Phe Gly Leu Leu Lys Val Asp Tyr Leu
            20                  25

<210> SEQ ID NO 5
<211> LENGTH: 25
<212> TYPE: PRT
<213> ORGANISM: Thermoplasma volcanium

<400> SEQUENCE: 5

Trp Ser Leu Ala Asp Asn Tyr Glu Trp Ala Ser Gly Phe Ser Met Arg
1               5                   10                  15

Phe Gly Leu Leu Lys Val Asp Tyr Asn
            20                  25

<210> SEQ ID NO 6
<211> LENGTH: 25
<212> TYPE: PRT
<213> ORGANISM: Pyrococcus furiosus

<400> SEQUENCE: 6

Trp Ser Leu Thr Asp Asn Tyr Glu Trp Ala Gln Gly Phe Arg Met Arg
1               5                   10                  15

Phe Gly Leu Val Tyr Val Asp Phe Glu
            20                  25

<210> SEQ ID NO 7
<211> LENGTH: 25
<212> TYPE: PRT
<213> ORGANISM: Agrobacterium tumefaciens

<400> SEQUENCE: 7

Trp Ser Leu Met Asp Asn Phe Glu Trp Ala Glu Gly Tyr Arg Met Arg
```

```
                1               5                  10                 15
Phe Gly Leu Val His Val Asp Tyr Glu
            20                  25

<210> SEQ ID NO 8
<211> LENGTH: 25
<212> TYPE: PRT
<213> ORGANISM: Bacillus circulans

<400> SEQUENCE: 8

Trp Ser Leu Met Asp Asn Phe Glu Trp Ala Glu Gly Tyr Gly Met Arg
1               5                  10                 15

Phe Gly Leu Val His Val Asp Tyr Asp
            20                  25

<210> SEQ ID NO 9
<211> LENGTH: 25
<212> TYPE: PRT
<213> ORGANISM: Agrobacterium sp. (strain ATCC 21400)

<400> SEQUENCE: 9

Trp Ser Leu Met Asp Asn Phe Glu Trp Ala Glu Gly Tyr Arg Met Arg
1               5                  10                 15

Phe Gly Leu Val His Val Asp Tyr Gln
            20                  25

<210> SEQ ID NO 10
<211> LENGTH: 25
<212> TYPE: PRT
<213> ORGANISM: Rhizobium meliloti

<400> SEQUENCE: 10

Trp Ser Leu Met Asp Asn Phe Glu Trp Ala Glu Gly Tyr Arg Met Arg
1               5                  10                 15

Phe Gly Ile Val His Val Asp Tyr Glu
            20                  25

<210> SEQ ID NO 11
<211> LENGTH: 25
<212> TYPE: PRT
<213> ORGANISM: Bacillus halodurans

<400> SEQUENCE: 11

Trp Ser Leu Leu Asp Asn Phe Glu Trp Ala Glu Gly Tyr Ser Met Arg
1               5                  10                 15

Phe Gly Ile Val His Val Asn Tyr Arg
            20                  25

<210> SEQ ID NO 12
<211> LENGTH: 25
<212> TYPE: PRT
<213> ORGANISM: Paenibacillus polymyxa

<400> SEQUENCE: 12

Trp Ser Leu Leu Asp Asn Phe Glu Trp Ala Glu Gly Tyr Asn Met Arg
1               5                  10                 15

Phe Gly Met Ile His Val Asp Phe Arg
            20                  25

<210> SEQ ID NO 13
<211> LENGTH: 25
<212> TYPE: PRT
```

<213> ORGANISM: Pyrococcus woesi

<400> SEQUENCE: 13

Trp Ser Leu Ala Asp Asn Tyr Glu Trp Ala Ser Gly Phe Ser Met Arg
1               5                   10                  15

Phe Gly Leu Leu His Val Asp Tyr Asn
            20                  25

<210> SEQ ID NO 14
<211> LENGTH: 25
<212> TYPE: PRT
<213> ORGANISM: Dalbergia cochinchinensis

<400> SEQUENCE: 14

Trp Ser Leu Leu Asp Asn Phe Glu Trp Ala Glu Gly Tyr Thr Ser Arg
1               5                   10                  15

Phe Gly Leu Tyr Phe Val Asn Tyr Thr
            20                  25

<210> SEQ ID NO 15
<211> LENGTH: 25
<212> TYPE: PRT
<213> ORGANISM: Costus specious

<400> SEQUENCE: 15

Trp Ala Leu Thr Asp Asn Phe Glu Trp Asp Lys Gly Tyr Thr Glu Arg
1               5                   10                  15

Phe Gly Leu Ile Tyr Ile Asp Tyr Asp
            20                  25

<210> SEQ ID NO 16
<211> LENGTH: 25
<212> TYPE: PRT
<213> ORGANISM: Homo sapiens

<400> SEQUENCE: 16

Arg Ser Leu Ile Asp Gly Phe Glu Gly Pro Ser Gly Tyr Ser Gln Arg
1               5                   10                  15

Phe Gly Leu His His Val Asn Phe Ser
            20                  25

<210> SEQ ID NO 17
<211> LENGTH: 25
<212> TYPE: PRT
<213> ORGANISM: Sinapis alba

<400> SEQUENCE: 17

Trp Ala Leu Gly Asp Asn Tyr Glu Phe Cys Lys Gly Phe Thr Val Arg
1               5                   10                  15

Phe Gly Leu Ser Tyr Val Asn Trp Asp
            20                  25

<210> SEQ ID NO 18
<211> LENGTH: 25
<212> TYPE: PRT
<213> ORGANISM: Staphylococcus aureus

<400> SEQUENCE: 18

Trp Ser Leu Met Asp Val Phe Ser Trp Ser Asn Gly Tyr Glu Lys Arg
1               5                   10                  15

Tyr Gly Leu Phe Tyr Val Asp Phe Glu
            20                  25

```
<210> SEQ ID NO 19
<211> LENGTH: 36
<212> TYPE: DNA
<213> ORGANISM: Artificial sequence
<220> FEATURE:
<223> OTHER INFORMATION: Oligonucleotide primer

<400> SEQUENCE: 19
ccatgggaca ccaccaccac caccaccact cattac                                 36

<210> SEQ ID NO 20
<211> LENGTH: 36
<212> TYPE: DNA
<213> ORGANISM: Artificial sequence
<220> FEATURE:
<223> OTHER INFORMATION: Oligonucleotide primer

<400> SEQUENCE: 20
ctcgagttag tgcctttatg gctttactgg aggtac                                 36

<210> SEQ ID NO 21
<211> LENGTH: 35
<212> TYPE: DNA
<213> ORGANISM: Artificial sequence
<220> FEATURE:
<223> OTHER INFORMATION: Oligonucleotide primer

<400> SEQUENCE: 21
tctagctgat aattactgtt gggcttcagg attct                                  35

<210> SEQ ID NO 22
<211> LENGTH: 35
<212> TYPE: DNA
<213> ORGANISM: Artificial sequence
<220> FEATURE:
<223> OTHER INFORMATION: Oligonucleotide primer

<400> SEQUENCE: 22
ctagctgata attacgaatg tgcttcagga ttctc                                  35

<210> SEQ ID NO 23
<211> LENGTH: 30
<212> TYPE: DNA
<213> ORGANISM: Artificial sequence
<220> FEATURE:
<223> OTHER INFORMATION: Oligonucleotide primer

<400> SEQUENCE: 23
gcttcaggat tctcttgtag gtttggtctg                                        30
```